(12) United States Patent
Commercon et al.

(10) Patent No.: US 9,056,914 B2
(45) Date of Patent: Jun. 16, 2015

(54) ANTICANCER DERIVATIVES, PREPARATION THEREOF AND THERAPEUTIC USE THEREOF

(71) Applicant: SANOFI, Paris (FR)

(72) Inventors: Alain Commercon, Paris (FR); Laurence Gauzy-Lazo, Paris (FR); Philippe Hubert, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/750,691

(22) Filed: Jan. 25, 2013

(65) Prior Publication Data

US 2013/0137659 A1    May 30, 2013

Related U.S. Application Data

(63) Continuation of application No. PCT/IB2011/053310, filed on Jul. 25, 2011.

(30) Foreign Application Priority Data

Jul. 26, 2010 (FR) .................................. 10 56103

(51) Int. Cl.
| | |
|---|---|
| C07D 487/04 | (2006.01) |
| C07K 16/40 | (2006.01) |
| A61K 31/5513 | (2006.01) |
| A61K 47/48 | (2006.01) |
| C07D 207/20 | (2006.01) |
| C07D 243/14 | (2006.01) |
| C07D 519/00 | (2006.01) |
| C07K 16/28 | (2006.01) |

(52) U.S. Cl.
CPC ............. *C07K 16/40* (2013.01); *A61K 31/5513* (2013.01); *A61K 47/48215* (2013.01); *C07D 207/20* (2013.01); *C07D 243/14* (2013.01); *C07D 487/04* (2013.01); *C07D 519/00* (2013.01); *C07K 16/2866* (2013.01)

(58) Field of Classification Search
CPC .................................................. C07D 487/04
USPC ......................................... 540/496; 514/220
See application file for complete search history.

(56) References Cited

U.S. PATENT DOCUMENTS

| 5,208,020 A | 5/1993 | Chari et al. |
| 8,314,244 B2 | 11/2012 | Bigot |

FOREIGN PATENT DOCUMENTS

| EP | 0306943 | 3/1989 |
| EP | 1813614 | 8/2007 |
| FR | 1516743 | 2/1968 |
| WO | 90/06774 | 6/1990 |
| WO | 00/12507 | 3/2000 |
| WO | 00/12508 | 3/2000 |
| WO | 2004/016801 | 2/2004 |
| WO | 2004/043344 | 5/2004 |
| WO | 2004/103272 | 12/2004 |
| WO | 2005/009369 | 2/2005 |
| WO | 2005/040170 | 5/2005 |
| WO | 2005/077090 | 8/2005 |
| WO | 2005/085259 | 9/2005 |
| WO | 2005/085260 | 9/2005 |
| WO | 2006/061258 | 6/2006 |
| WO | 2006/069246 | 6/2006 |
| WO | 2007/085930 | 8/2007 |
| WO | 2007/093873 | 8/2007 |
| WO | 2007/102069 | 9/2007 |
| WO | 2007/144709 | 12/2007 |
| WO | 2008/010101 | 1/2008 |
| WO | 2008/047242 | 4/2008 |
| WO | 2009/016516 | 2/2009 |
| WO | 2009/026274 | 2/2009 |
| WO | 2009/134976 | 11/2009 |
| WO | 2009/134977 | 11/2009 |

(Continued)

OTHER PUBLICATIONS

Abdel-Magid et al., "Reductive Amination of Aldehydes and Ketones with Sodium Triacetoxyborohydride. Studies on Direct and Indirect Reductive Amination Procedures," J. Org. Chem. vol. 61, pp. 3849-3862 (1996).

Anderson et al., "N,N'-Carbonyldiimidazole, a new reagent for peptide synthesis," J. Am. Chem. Soc., vol. 80, No. 16, p. 4423 (1958).

Ben-Aroya et al., "Synthesis and structural characterization of 3-O-ethylene glycol functionalized cellulose derivatives," Carbohydrate Polymers, 76, pp. 60-67 (2009).

Burns et al., "Selective Reduction of Disulfides by Tris(2-carboxyethyl)phosphine," J. Org. Chem., 56(8), pp. 2648-2650 (1991).

(Continued)

*Primary Examiner* — Bruck Kifle
(74) *Attorney, Agent, or Firm* — Sandra A. Brockman-Lee

(57) ABSTRACT

Provided herein are compounds of formula (I):

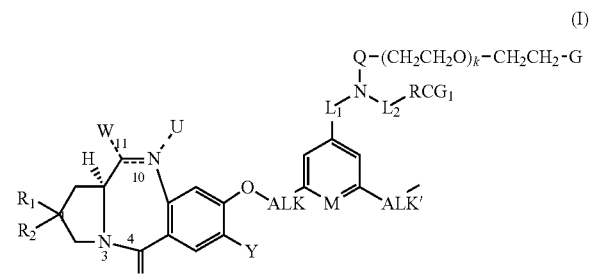

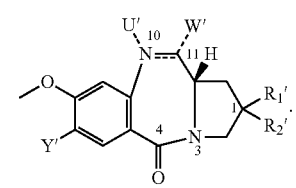

21 Claims, 6 Drawing Sheets

(56) References Cited

FOREIGN PATENT DOCUMENTS

| | | |
|---|---|---|
| WO | 2010/076474 | 7/2010 |
| WO | 2011/039721 | 4/2011 |

OTHER PUBLICATIONS

Carlsson et al., "Protein thiolation and reversible protein-protein conjugation. N-Succinimidyl 3-(2-pyridyldithio) propionate, a new heterobifunctional reagent," Biochem. J., 173, pp. 723-737 (1978).

Carter et al., "Antibody-drug conjugates for cancer therapy," Cancer J., vol. 14, No. 3, pp. 154-169 (2008).

Chari, "Targeted cancer therapy: conferring specificity to cytotoxic drugs," Acc. Chem. Res., vol. 41, No. 1, pp. 98-107 (2008).

Chessa et al., "Synthesis of poly(pyridylthioether) dendrimers incorporating a Fe2(CO)6 cluster core," Tetrahedron, vol. 61, No. 7, pp. 1755-1763 (2005).

Chin et al., "Addition of p-Azido-L-phenylalanine to the Genetic Code of *Escherichia coli*," J. Am. Chem. Soc., vol. 124, pp. 9026-9027 (2002).

Cromwell et al., "Protein Aggregation and Bioprocessing," AAPS Journal, vol. 8, No. 3, pp. E572-E579 (2006).

Degraaf et al., "Nonnatural Amino Acids for Site-Specific Protein Conjugation," Bioconjugate Chem., vol. 20, No. 7 pp. 1281-1295 (2009).

Farmer et al., "Synthesis and DNA Corsslinking Ability of a Dimeric Anthramycin Analog," Tetrahedron Letters, vol. 29, No. 40, pp. 5105-5108 (1988).

Garnett, "Targeted drug conjugates: principles and progress," Advanced Drug Delivery Reviews, 53, pp. 171-216 (2001).

Huskens et al., "The addition of hydroxyl compounds to unsaturated carboxylic acids homogeneously catalysed by lanthanide(III)," Tetrahedron, vol. 49. No. 15, pp. 3149-3164 (1993).

International Search Report as issued in PCT/IB2011/053310, mailed on Sep. 30, 2011.

Junutula et al., "Site-specific conjugation of a cytotoxic drug to an antibody improves the therapeutic index," Nature Biotechnology, 26(8), pp. 925-932 (2008).

Kumar et al., "Design, synthesis and in vitro cytotoxic studies of novel bis-pyrrolo[2,1][1,4] benzodiazepine-pyrrole and imidazole polyamide conjugates," Eur. J. Med. Chem., vol. 40, pp. 641-654 (2005).

Litzen et al., "Separation and Quantitation of Monoclonal Antibody Aggregates by Asymmetrical Flow Field-Flow Fractionation and Comparison to Gel Permeation Chromatography," Analytical Biochemistry, vol. 212, No. 2, pp. 469-480 (1993).

Luening et al., "Concave Pyridines and 1,10-Phenanthrolines with sulfonamide bridgeheads. Increased Basicity by 4-Diethylamino Substitution of the Pyridine Unit," Liebigs Ann. Chem., 10, pp. 987-988 (1991).

Marquis et al., "Photoresponsive Supramolecular Systems: Synthesis and Photophysical and Photochemical Study of Bis-(9,10-anthracenediyl)coronands AAOnOn," J. Org. Chem., 60(24), pp. 7984-7996 (1995).

Miller et al., "Abstract B126: Potent antigen-specific anti-tumor activity observed with antibody-drug conjugates (ADCs) made using a new class of DNA-crosslinking agents," Mol. Cancer Ther., vol. 8 (12 Suppl.), Meeting Abstract B126 (2009).

Miller et al., "Amphiphilic Conjugates of Human Brain Natriuretic Peptide Designed for Oral Delivery: In Vitro Activity Screening," Bioconjugate Chem., 17, pp. 267-274 (2006).

Monneret et al., "Ciblage de molecules antitumorales par les anticorps monoclonaux," Bulletin du Cancer, 87(11), pp. 829-838 (2000).

Mori et al., "Total Syntheses of Prothracarcin and Tomaymycin by use of Palladium Catalyzed Carbonylation," Tetrahedron, 42(14), pp. 3793-3806 (1986).

Paul et al., "N,N'-Carbonyldiimidazole, a new peptide forming reagent," J. Am. Chem. Soc., vol. 82, No. 17, pp. 4596-4600 (1960).

Ricart et al., "Technology Insight: cytotocix drug immunoconjugates for cancer therapy," Nature Clinical Practice Oncology, 4(4), pp. 245-255 (2007).

Skerlj et al., "Facile synthesis of a selectively protected briazamacrocycle," Tetrahedron Letters, vol. 43, pp. 7569-7571 (2002).

Tozuka et al., "Studies on Tomaymycin, II Total Syntheses of the Antitumor Antibiotics, E- and Z-Tomaymycins," J. Antibiotics, XXXVI(3), pp. 276-282 (1983).

Wang et al., "Fractionation of monoclonal antibody aggregates using membrane chromatography," J. Membrane Sci., 318, pp. 311-316 (2008).

Monneret et al., "Ciblage de molecules antitumorales par les anticorps monoclonaux," Bulletin du Cancer, 87(11), pp. 829-838 (2000)—English language machine translation of the Summary.

ANTICANCER DERIVATIVES, PREPARATION THEREOF AND THERAPEUTIC USE THEREOF

The present invention relates to conjugates of pyrrolo[1,4] benzodiazepine (PBD) dimers, to compositions containing them and to their therapeutic use, especially as anticancer agents. The invention also relates to the process for preparing the conjugates and to their use as anticancer agents, and also to the dimers themselves.

BACKGROUND

Pyrrolo[1,4]benzodiazepine dimers are anticancer agents that act by covalently binding to cellular DNA. These derivatives have been described in patent applications WO 00/12508 and WO 2005/085260 and also in the following publications: *Eur. J. Med. Chem.* 2005, 40, 641-654; *Tetrahedron Letters* 1988, 29(40), 5105-5108.

Conjugates chemistry has been known for many years and has been applied to several families of cytotoxic agents, for instance maytansinoids (WO 04103272), taxanes (WO 06061258), leptomycins (WO 07144709), CC-1065 and analogues thereof (WO 2007102069); with regard to conjugates, see also Monneret C. et al., *Bulletin du Cancer* 2000, 87(11), 829-38; Ricart A. D. et al., *Nature Clinical Practice Oncology* 2007, 4, 245-255; Singh R. and Rickson H. K., *Therapeutic Antibodies: Methods and Protocols*, 2009, 525, 445-467.

Conjugates of pyrrolo[1,4]benzodiazepine dimers have been described in patent applications WO 07085930 and WO 2009/016516. The dimers used have the formulae:

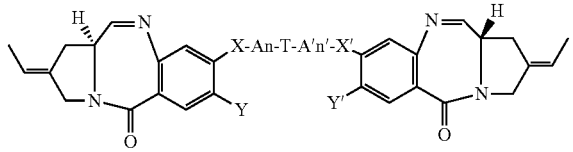

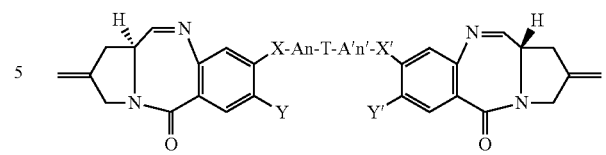

in which T may represent an aryl or heteroaryl group substituted with $-G-D-(Z)_p-SZ_a$ or $-G-D-(Z)_p-C(=O)Z_bR_b$. G represents a single or double bond or alternatively —O—, —S— or —NR—. D represents a single bond or one of the following groups: -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F— for which E and F are chosen from —(OCH$_2$CH$_2$)$_i$alkyl(OCH$_2$CH$_2$)$_j$—, -alkyl(OCH$_2$CH$_2$)$_i$-alkyl, —(OCH$_2$CH$_2$)$_i$—, —(OCH$_2$CH$_2$)$_i$cycloalkyl(OCH$_2$CH$_2$)$_j$—, —(OCH$_2$CH$_2$)$_i$heterocyclyl-(OCH$_2$CH$_2$)$_j$—, —(OCH$_2$CH$_2$)$_i$aryl(OCH$_2$CH$_2$)$_j$—, —(OCH$_2$CH$_2$)$_i$ heteroaryl(OCH$_2$CH$_2$)$_j$—, -alkyl-(OCH$_2$CH$_2$)$_i$alkyl(OCH$_2$CH$_2$)$_j$—, -alkyl-(OCH$_2$CH$_2$)$_i$—, -alkyl-(OCH$_2$CH$_2$)$_i$cycloalkyl-(OCH$_2$CH$_2$)$_j$—, -alkyl (OCH$_2$CH$_2$)$_i$heterocyclyl(OCH$_2$CH$_2$)$_j$—, -alkyl-(OCH$_2$CH$_2$)$_i$aryl-(OCH$_2$CH$_2$)$_j$—, -alkyl(OCH$_2$CH$_2$)$_i$heteroaryl(OCH$_2$CH$_2$)$_j$—, -cycloalkyl-alkyl-, -alkyl-cycloalkyl-, -heterocyclyl-alkyl-, -alkyl-heterocyclyl-, -alkyl-aryl-, -aryl-alkyl-, -alkyl-heteroaryl-, -heteroaryl-alkyl-. i and j represent integers ranging from 0 to 2000. Z represents an alkyl group and p is an integer equal to 0 or 1. In these compounds, the R of the group NR does not comprise a PEG chain.

Immunogen described in November 2009 at the EORTC Congress (Abstract B-126) the following conjugate:

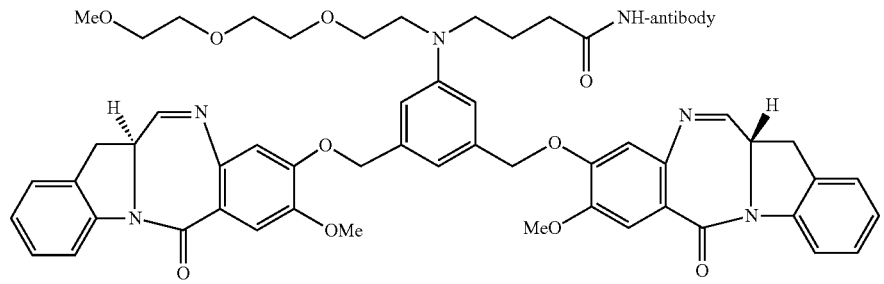

which is distinguished by the nature of the linker and of the cytotoxic compound. This compound was redescribed at the Sixth Annual PEGS Congress in Boston which took place on 17 to 21 May 2010, and also the following precursors:

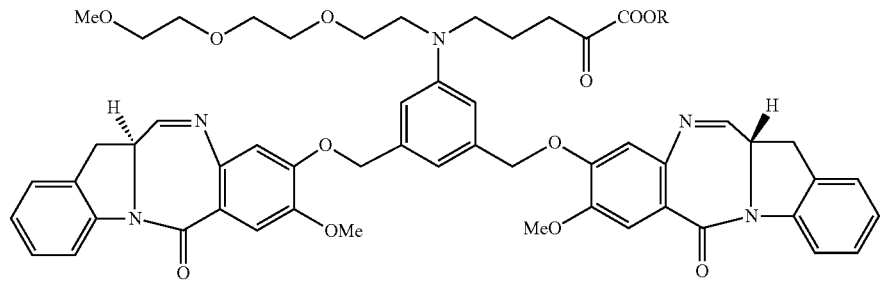

with R=N-succinimidyl or methyl

The following dimers are especially described, respectively, in WO 07085930 and WO 2009/016516:

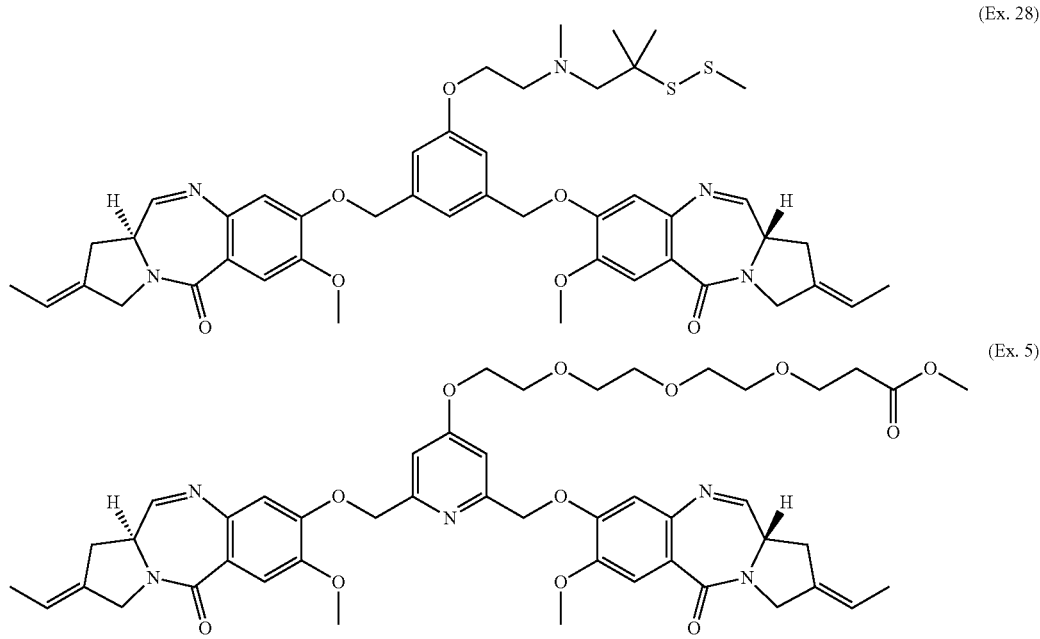

(Ex. 28)

(Ex. 5)

These three applications do not describe or suggest the novel linkers of the invention, which comprise one or two pegylated chains.

SUMMARY

The technical problem that the present invention intends to solve is that of proposing novel conjugates of pyrrolo[1,4] benzodiazepine dimers.

DEFINITIONS

The following definitions apply:
conjugate: a cell binding agent to which is covalently attached at least one molecule of a cytotoxic compound;
cell binding agent: a molecule that has affinity for a biological target: it may be, for example, a ligand, a protein, an antibody, more particularly a monoclonal antibody, a protein or antibody fragment, a peptide, an oligonucleotide or an oligosaccharide. The binding agent has the function of directing the biologically active compound as a cytotoxic agent to the biological target;
biological target: an antigen (or group of antigens) preferentially located at the surface of cancer cells or stromal cells associated with this tumour; these antigens possibly being, for example, a growth factor receptor, a mutated "tumour suppressant" gene or oncogene product, an angiogenesis-related molecule, an adhesion molecule;
linker: a set of atoms for covalently attaching a cytotoxic compound to the binding agent;
alkyl group: a saturated aliphatic hydrocarbon-based group obtained by removing a hydrogen atom from an alkane. The alkyl group may be linear or branched. Examples that may be mentioned include methyl, ethyl, propyl, isopropyl, butyl, isobutyl, tert-butyl, pentyl, 2,2-dimethylpropyl, hexyl;

cycloalkyl group: a cyclic alkyl group comprising between 3 and 8 carbon atoms engaged in the ring structure.
Examples that may be mentioned include cyclopropyl, cyclobutyl, cyclopentyl and cyclohexyl groups;
aryl group: a monocyclic or bicyclic aromatic group not containing any heteroatoms. It is more particularly a phenyl or naphthyl group;
heteroaryl group: a monocyclic or bicyclic aromatic group comprising at least one heteroatom (O, S, N) engaged in the ring and connected to the carbon atoms forming the ring. It is more particularly a pyridyl, pyrrolyl, thienyl, furyl, pyrimidinyl or triazolyl group;
heterocycloalkyl group: a cycloalkyl group comprising at least one heteroatom (O, S, N) engaged in the ring and connected to the carbon atoms forming the ring. It is more particularly a piperazino, N-methylpiperazino, morpholino, piperidino or pyrrolidino group;
alkoxy group: a group —O-alkyl, in which the alkyl group is as defined above;
alkanoyloxy group: a group —O—CO-alkyl, in which the alkyl group is as defined above;
alkylene group: a saturated divalent group of empirical formula —$C_mH_{2m}$—, obtained by removing two hydrogen atoms from an alkane. Examples that may be mentioned include methylene (—$CH_2$—), ethylene (—$CH_2CH_2$—), propylene (—$CH_2CH_2CH_2$—), butylene (—$CH_2CH_2CH_2CH_2$—), isobutylene

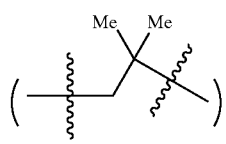

and hexylene (—$CH_2CH_2CH_2CH_2CH_2CH$—) groups. The alkylene group may more particularly be of formula —$(CH_2)_m$—, m representing an integer;

in the ranges of values, the limits are included (e.g. a range of the type "i ranging from 1 to 6" includes the limits 1 and 6. Furthermore, the range also describes all points in the range; thus, "i ranging from 1 to 6" describes the values 1, 2, 3, 4, 5 and 6.

ABBREVIATIONS USED

EtOAc: ethyl acetate; ALK: alkylene group; $(C_x-C_y)$ALK: group $(C_x-C_y)$alkylene; TLC: thin-layer chromatography; MSC: methanesulfonyl chloride; DBU: 1,8-diazabicyclo [5.4.0]undec-7-ene; DCC: N,N'-dicyclohexylcarbodiimide; DCM: dichloromethane; DEAD: diethyl azodicarboxylate; DIC: N,N'-diisopropylcarbodiimide; DIPEA: N,N-diisopropylethylamine; DMA: dimethylacetamide; DMAP: 4-dimethylaminopyridine; DME: dimethoxyethane; DMF: dimethylformamide; DMSO: dimethyl sulfoxide; $e_{WL\ nm}$: molar extinction coefficient at the wavelength WL; EEDQ: 2-ethoxy-1-ethoxycarbonyl-1,2-dihydroquinoline; EDCI: N-(3-dimethylaminopropyl)-N'-ethylcarbodiimide; EDTA: ethylenediaminetetraacetic acid; Fmoc: fluorenylmethoxycarbonyl; Hal: halogen atom; HOBt: 1-hydroxybenzotriazole; HEPES: 4-(2-hydroxyethyl)-1-piperazineethanesulfonic acid; WL: wavelength; Me: methyl; NHS: N-hydroxysuccinimide; NMP: N-methylpyrrolidinone; RP: reduced pressure; Rf: retention factor; SEC: steric exclusion chromatography; RT: room temperature; TBDMS: tert-butyldimethylsilyl; TEA: triethylamine; TFA: trifluoroacetic acid; TIPS: triisopropylsilyl; THF: tetrahydrofuran; $t_R$: retention time.

DETAILED DESCRIPTION

Figure 1:
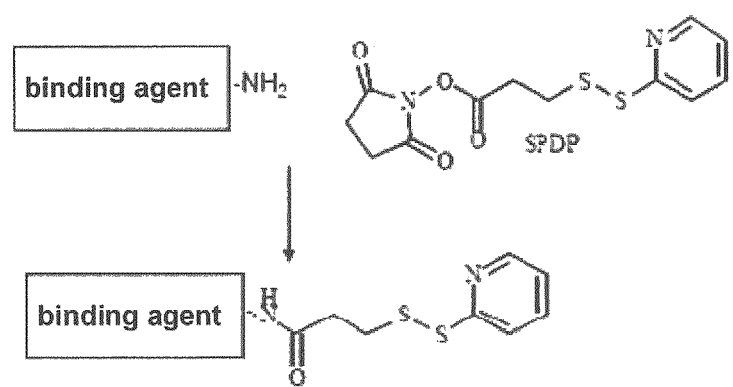
FIG. 1 shows modification of the binding agent by SPDP.

The invention relates to compounds of formula (I):

in which:
═══ represents a single bond or a double bond, with the condition that
if ═══ represents a single bond, then:
U and/or U', which may be identical or different, represent, independently of each other, H;
W and/or W', which may be identical or different, represent, independently of each other: OH, —OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —SO$_3^-$, —NR-SOOR', —NRR', a cyclic amine such that N10 and C11 are included in a ring, —NROR', —NRCOR', —N$_3$, —CN, Hal, a trialkylphosphonium or triarylphosphonium group;
if ═══ represents a double bond, then:
U and U' are absent;
W and/or W', which may be identical or different, represent, independently of each other, H;
$R_1$, $R_2$, $R_1'$, $R_2'$, which may be identical or different, represent, independently of each other: H, Hal or a group $(C_1-C_6)$alkyl optionally substituted with one or more substituents chosen from: Hal, CN, NRR', CF$_3$, OR, an aryl or heteroaryl group, S(O)$_q$R with q=0, 1 or 2;
or alternatively
$R_1$ and $R_2$ and/or $R_1'$ and $R_2'$ together form, respectively, a double bond =CH$_2$ or =CH—CH$_3$;
Y and Y', which may be identical or different, represent, independently of each other, H or —OR;
M represents CH or N;
ALK and ALK' denote a group $(C_1-C_6)$alkylene;
R and R' represent, independently of each other, H or a group $(C_1-C_6)$alkyl or aryl optionally substituted with one or more substituents chosen from: Hal, CN, NRR', CF$_3$, OR, an aryl or heteroaryl group;
$L_1$ represents:
a single bond;
or
the group —(OCH$_2$CH$_2$)$_i$—, attached to the phenyl or pyridyl ring via the oxygen atom, i representing an integer ranging from 2 to 40, preferably from 2 to 10, preferably equal to 3;
or
the group -D-(C$_1$-C$_6$)ALK- attached to the phenyl or pyridyl ring via D, in which D represents —O—, —NH— or —N(C$_1$-C$_4$)alkyl-;

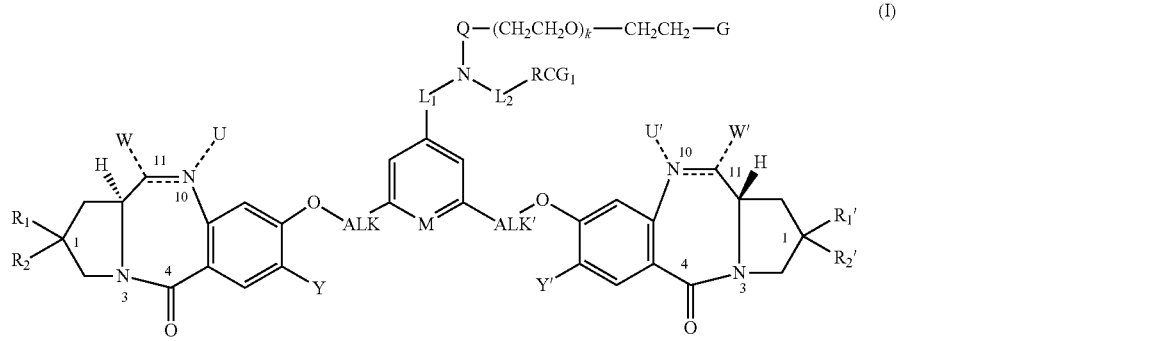

$L_2$ represents:
- a group —$(C_1-C_6)$ALK-;
or
- the group —$(CH_2CH_2O)_j$—$CH_2CH_2$—, j representing an integer ranging from 1 to 40, preferably from 1 to 10, preferably equal to 2 or 3;
or
- a group —$(CH_2CH_2O)_j$—$CH_2CH_2NR''$—$(C_1-C_6)$ ALK-, attached to the nitrogen atom via the unit —$(CH_2CH_2O)$—, j representing an integer ranging from 1 to 40, preferably from 1 to 10, preferably equal to 2 or 3, and R" representing H or a group $(C_1-C_4)$ alkyl;

Q represents a single bond or the group C(=O);

k represents an integer ranging from 0 to 40, preferably from 1 to 40, rather from 1 to 10;

G represents a group —OR or —NRR', R and R' being as defined previously or being such that they form, with the nitrogen atom to which they are attached, a group $(C_4-C_{10})$heterocycloalkyl which may comprise in the ring another heteroatom chosen from N, O and S and which may be optionally substituted with at least one substituent chosen from a group $(C_1-C_4)$alkyl, a halogen atom and a hydroxyl group;

RCG1 represents the group —$SZ_a$ or —$C(=O)$—$Z_bR_b$:

$Z_a$ represents Ac, $R_a$ or $SR_a$, $R_a$ represents H, or a group $(C_1-C_6)$alkyl, $(C_3-C_8)$cycloalkyl, aryl, heteroaryl or $(C_4-C_{10})$heterocycloalkyl optionally substituted with one or more substituents chosen from: Hal, CN, NRR', $CF_3$, OR, $NO_2$, an aryl or heteroaryl group;

$Z_b$ represents a single bond, —O— or —NH— and $R_b$ representing H or a group $(C_1-C_6)$alkyl, $(C_3-C_8)$cycloalkyl, aryl, heteroaryl or $(C_4-C_{10})$heterocycloalkyl or alternatively $Z_b$ represents a single bond and $R_b$ represents Hal;

with the condition that if $L_1$ represents a single bond, then RCG1 represents —$SZ_a$.

More particularly, compounds of formula (IA) or (IB) are provided:

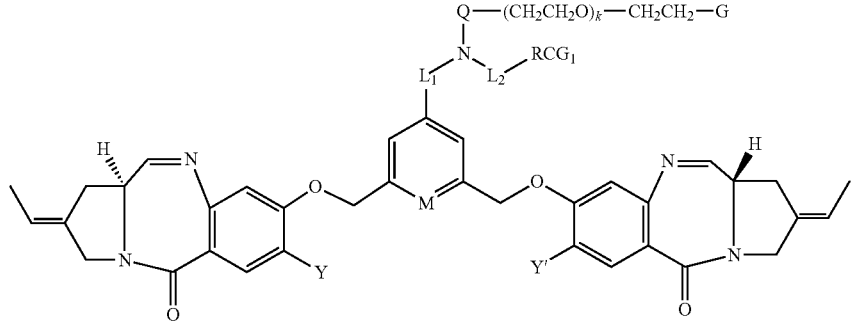

(IA)

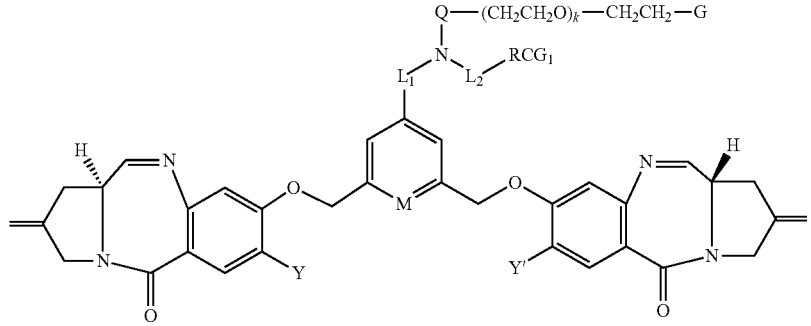

(IB)

The invention also relates to the process for preparing a conjugate, which consists in: (i) placing in contact and leaving to react an aqueous solution, optionally buffered, of the binding agent, optionally modified with a modifying agent, and a solution of a compound of formula (I), (ii) and then in optionally separating the conjugate formed in step (i) from the compound of formula (I) and/or the unreacted binding agent and/or the aggregates that may possibly have formed. The chemical group RCG1 of the compound of formula (I) must be reactive towards the chemical groups RCG2 present on the binding agent, especially towards the amino groups present on the antibodies, the said chemical groups RCG2 having been introduced, where appropriate, by the modifying agent so as to attach the compound of formula (I) to the binding agent by formation of a covalent bond.

The invention also relates to a conjugate and to a conjugate solution that may be obtained via the process described above.

The invention also relates to the use of a derivative of formula (I) for the preparation of a binding agent to which is covalently attached in the para position of M the dimer of formula:

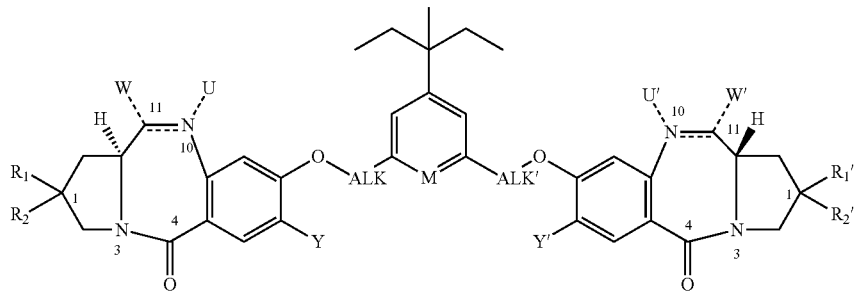

The compound, the conjugate and the conjugate solution may be used as anticancer agents.

The invention also relates to the compound of formula $P_2$:

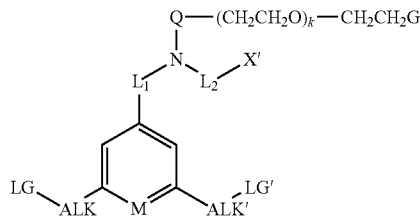

in which $L_1$, $L_2$, Q, k, ALK, ALK' and G are as defined previously; LG and LG' represent a leaving group and X' represents RCG1.

The invention also relates to a binding agent to which has been covalently attached in the para position of M the dimer of formula:

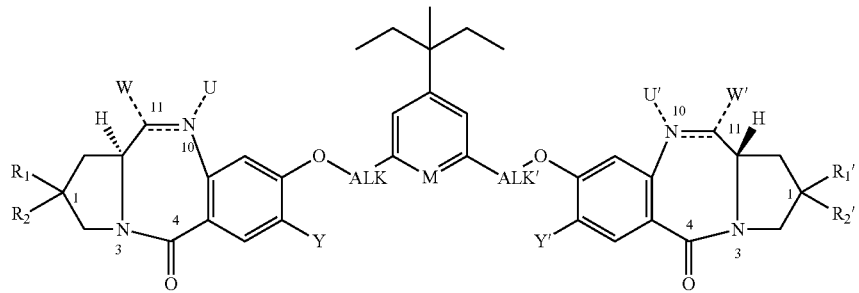

after reaction of a compound of the invention with the binding agent.

The invention relates to compounds of formula (I):

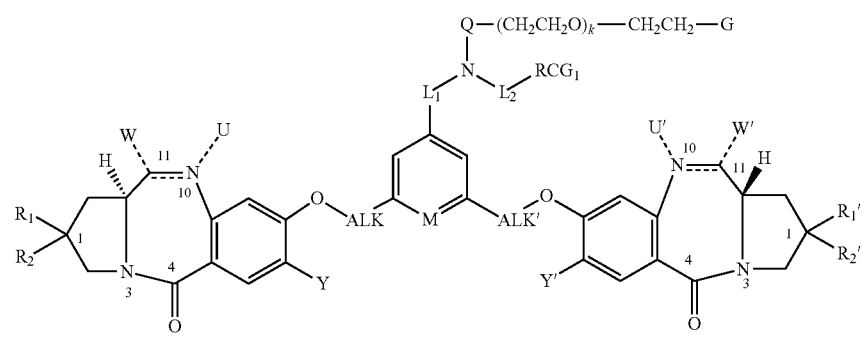

in which:
=== represents a single bond or a double bond, with the condition that
if === represents a single bond, then:
U and/or U', which may be identical or different, represent, independently of each other, H;
W and/or W', which may be identical or different, represent, independently of each other: OH, —OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —SO$_3^-$, —NRSOOR', —NRR', a cyclic amine such that N10 and C11 are included in a ring, —NROR', —NRCOR', —N$_3$, —CN, Hal, a trialkylphosphonium or triarylphosphonium group;
if === represents a double bond, then:
U and U' are absent;
W and/or W', which may be identical or different, represent, independently of each other, H;
$R_1$, $R_2$, $R_1'$, $R_2'$, which may be identical or different, represent, independently of each other: H, Hal or a group ($C_1$-$C_6$)alkyl optionally substituted with one or more substituents chosen from: Hal, CN, NRR', CF$_3$, OR, an aryl or heteroaryl group, S(O)$_q$R with q=0, 1 or 2;
or alternatively
$R_1$ and $R_2$ and/or $R_1'$ and $R_2'$ together form, respectively, a double bond =CH$_2$ or =CH—CH$_3$;
Y and Y', which may be identical or different, represent, independently of each other, H or —OR;
M represents CH or N;
ALK and ALK' denote a group ($C_1$-$C_6$)alkylene;
R and R' represent, independently of each other, H or a group ($C_1$-$C_6$)alkyl or aryl optionally substituted with one or more substituents chosen from: Hal, CN, NRR', CF$_3$, OR, an aryl or heteroaryl group;
$L_1$ represents:
a single bond;
or
the group —(OCH$_2$CH$_2$)$_i$—, attached to the phenyl or pyridyl ring via the oxygen atom, i representing an integer ranging from 2 to 40, preferably from 2 to 10, preferably equal to 3;
or
the group -D-($C_1$-$C_6$)ALK- attached to the phenyl or pyridyl ring via D, in which D represents —O—, —NH— or —N($C_1$-$C_4$)alkyl-;
$L_2$ represents:
a group —($C_1$-$C_6$)ALK-;
or
the group —(CH$_2$CH$_2$O)$_j$—CH$_2$CH$_2$—, j representing an integer ranging from 1 to 40, preferably from 1 to 10, preferably equal to 2 or 3;
or
a group —(CH$_2$CH$_2$O)$_j$—CH$_2$CH$_2$NR"—($C_1$-$C_6$) ALK-, attached to the nitrogen atom via the unit —(CH$_2$CH$_2$O)—, j representing an integer ranging from 1 to 40, preferably from 1 to 10, preferably equal to 2 or 3, and R" representing H or a group ($C_1$-$C_4$) alkyl;
Q represents a single bond or the group C(=O);
k represents an integer ranging from 0 to 40, preferably from 1 to 40, rather from 1 to 10;
G represents a group —OR or —NRR', R and R' being as defined previously or being such that they form, with the nitrogen atom to which they are attached, a group ($C_4$-$C_{10}$)heterocycloalkyl which may comprise in the ring another heteroatom chosen from N, O and S and which may be optionally substituted with at least one substituent chosen from a group ($C_1$-$C_4$)alkyl, a halogen atom and a hydroxyl group;
RCG1 represents the group —SZ$_a$ or —C(=O)—Z$_b$R$_b$:
Z$_a$ represents Ac, R$_a$ or SR$_a$,
R$_a$ represents H, or a group ($C_1$-$C_6$)alkyl, ($C_3$-$C_8$)cycloalkyl, aryl, heteroaryl or ($C_4$-$C_{10}$)heterocycloalkyl optionally substituted with one or more substituents chosen from: Hal, CN, NRR', CF$_3$, OR, NO$_2$, an aryl or heteroaryl group;
Z$_b$ represents a single bond, —O— or —NH— and R$_b$ representing H or a group ($C_1$-$C_6$)alkyl, ($C_3$-$C_8$)cycloalkyl, aryl, heteroaryl or ($C_4$-$C_{10}$)heterocycloalkyl or alternatively Z$_b$ represents a single bond and R$_b$ represents Hal;
with the condition that if $L_1$ represents a single bond, then RCG1 represents —SZ$_a$.
The compounds of formula (I) may thus exist in the form:

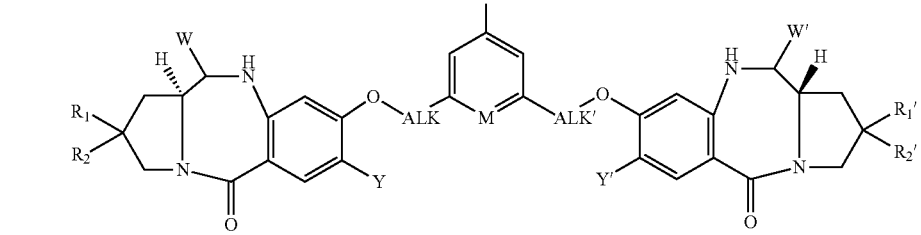

The invention also relates to compounds of formula (I'):

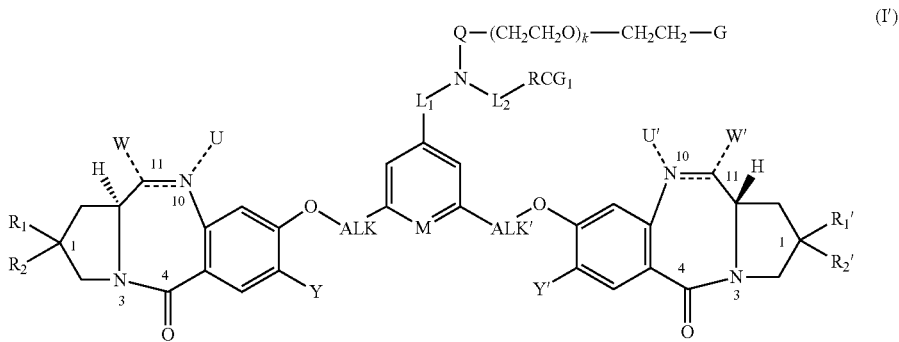

in which:
- === represents a single bond or a double bond, with the condition that if === represents a single bond, then:
  - ---- represents a single bond;
  - U and/or U', which may be identical or different, represent, independently of each other, H;
  - W and/or W', which may be identical or different, represent, independently of each other: OH, —OR, —OCOR, —COOR, —OCOOR, —OCONRR', a cyclic carbamate such that N10 and O11 are included in a ring, —NRCONRR', —OCSNHR, a cyclic thiocarbamate such that N10 and O11 are included in a ring, —SH, —SR, —SOR, —SOOR, —SO$_3^{-1}$, —NRSOOR', —NRR', a cyclic amine such that N10 and C11 are included in a ring, —NROR', —NRCOR', —N$_3$, —CN, Hal, a trialkylphosphonium or triarylphosphonium group;
- $R_1$, $R_2$, $R_1'$, $R_2'$, which may be identical or different, represent, independently of each other: H, Hal or a group ($C_1$-$C_6$)alkyl optionally substituted with one or more substituents chosen from: Hal, CN, NRR', CF$_3$, OR, an aryl or heteroaryl group, S(O)$_q$R with q=0, 1 or 2;
- or alternatively
- $R_1$ and $R_2$ and/or $R_1'$ and $R_2'$ together form, respectively, a double bond =CH$_2$ or =CH—CH$_3$;
- Y and Y', which may be identical or different, represent, independently of each other, H or —OR;
- M represents CH or N;
- ALK and ALK' denote a group ($C_1$-$C_6$)alkylene;
- R and R' represent, independently of each other, H or a group ($C_1$-$C_6$)alkyl or aryl optionally substituted with one or more substituents chosen from: Hal, CN, NRR', CF$_3$, OR, an aryl or heteroaryl group;
- $L_1$ represents:
  - a single bond;
  - or
  - the group —(OCH$_2$CH$_2$)$_i$—, attached to the phenyl or pyridyl ring via the oxygen atom, i representing an integer ranging from 2 to 40, preferably from 2 to 10;
  - or
  - the group -D-($C_1$-$C_6$)ALK- attached to the phenyl or pyridyl ring via D, in which D represents —O—, —NH— or —N($C_1$-$C_4$)alkyl-;
- $L_2$ represents:
  - a group —($C_1$-$C_6$)ALK-;
  - or
  - the group —(CH$_2$CH$_2$O)$_j$—CH$_2$CH$_2$—, j representing an integer ranging from 1 to 40, preferably from 1 to 10;
  - or
  - a group —(CH$_2$CH$_2$O)$_j$—CH$_2$CH$_2$NR"—($C_1$-$C_6$)ALK-, attached to the nitrogen atom via the unit —(CH$_2$CH$_2$O)—, j representing an integer ranging from 1 to 40, preferably from 1 to 10, and R" representing H or a group ($C_1$-$C_4$)alkyl;
- Q represents a single bond or the group C(=O);
- k represents an integer ranging from 0 to 40, preferably from 1 to 40, rather from 1 to 10;
- G represents a group —OR or —NRR', R and R' being as defined previously or being such that they form, with the nitrogen atom to which they are attached, a group ($C_4$-$C_{10}$)heterocycloalkyl which may comprise in the ring another heteroatom chosen from N, O and S and which may be optionally substituted with at least one substituent chosen from a group ($C_1$-$C_4$)alkyl, a halogen atom and a hydroxyl group;
- RCG1 represents the group —SZ$_a$ or —C(=O)—Z$_b$R$_b$;
- Z$_a$ represents Ac, R$_a$ or SR$_a$;
- R$_a$ represents H, or a group ($C_1$-$C_6$)alkyl, ($C_3$-$C_6$)cycloalkyl, aryl, heteroaryl or ($C_4$-$C_{10}$)heterocycloalkyl optionally substituted with one or more substituents chosen from: Hal, CN, NRR', CF$_3$, OR, NO$_2$, an aryl or heteroaryl group;
- Z$_b$ represents a single bond, —O— or —NH— and R$_b$ representing H or a group ($C_1$-$C_6$)alkyl, ($C_3$-$C_8$)cycloalkyl, aryl, heteroaryl or ($C_4$-$C_{10}$)heterocycloalkyl or alternatively Z$_b$ represents a single bond and R$_b$ represents Hal;

with the condition that if $L_1$ represents a single bond, then RCG1 represents —SZ$_a$.

The term L denotes the linker defined by

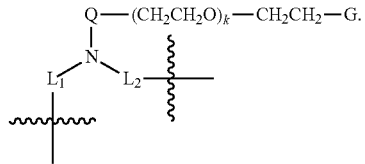

More particularly, if $L_1$ represents a single bond, $L_2$ represents —(CH$_2$CH$_2$O)$_j$—CH$_2$CH$_2$— or —(CH$_2$CH$_2$O)$_j$—CH$_2$CH$_2$NR"—($C_1$-$C_6$)ALK- and/or k≠2.

More particularly, when M represents N, -D-($C_1$-$C_6$)ALK- rather represents —O—($C_1$-$C_6$)ALK-.

More particularly, the two groups ALK and ALK' attached to the phenyl or pyridyl nucleus both denote a methylene group.

More particularly, D represents —O—, —NH— or —NMe-.

In formulae (I) and (I') above, each alkylene group (thus, for example, the two groups ALK and ALK') attached to the phenyl or pyridyl nucleus may be identical or different; according to another example, the group ALK of -D-($C_1$-$C_6$) ALK- may be identical to or different from the group ALK attached to the phenyl or pyridyl nucleus. ALK may be chosen, for example, from one of the following: —$CH_2$—, —$CH_2CH_2$—, $CH_2CMe_2$-, —$CH_2CH_2CH_2$—.

Y and Y' more particularly represent a group ($C_1$-$C_4$) alkoxy, especially the methoxy group.

R and R' may more particularly represent, independently of each other, H or a group ($C_1$-$C_6$)alkyl.

According to one particular embodiment, U=U' and/or W=W' and/or $R_1$=$R_1$' and/or $R_2$=$R_2$' and/or Y=Y' and/or both the groups ALK and ALK' attached to the phenyl or pyridyl nucleus are identical (symmetrical dimer, which is easier to prepare).

More particularly, W and W' are identical or different and represent OH, OMe, OEt, $NHCONH_2$, SMe.

R" may represent H or a group ($C_1$-$C_4$)alkyl, especially Me.

M more particularly represents a nitrogen atom (N).

ring another heteroatom chosen from N, O and S and which may be optionally substituted with at least one substituent chosen from a group ($C_1$-$C_4$)alkyl, a halogen atom and a hydroxyl group. The heterocycloalkyl group may be chosen especially from piperazino, N-methylpiperazino, morpholino, piperidino and pyrrolidino.

k represents an integer ranging from 0 to 40. k may take the value 0 (no PEG chain ending with G attached to the nitrogen atom). Among the compounds of the invention, a distinction may be made for those comprising a PEG chain ending with G attached to the nitrogen atom and k ranges from 1 to 40, rather from 1 to 10, rather from 1 to 5. A distinction may also be made for those comprising at least one PEG chain, i.e. those for which k ranges from 1 to 40, preferably from 1 to 10, rather from 1 to 5, and/or $L_1$=—(O$CH_2CH_2$)$_i$— and/or $L_2$=—(C$H_2CH_2$O)$_j$—$CH_2CH_2$— or alternatively —(C$H_2CH_2$O)$_j$ $CH_2CH_2$NR"—($C_1$-$C_6$)ALK-.

The compounds of formulae (I) and (I'), including those given as examples, may exist in the form of bases or of addition salts with pharmaceutically acceptable acids, and also in the form of hydrates or solvates of these bases or of these salts.

More particularly, a distinction is made for those of formula (IA) or (IB):

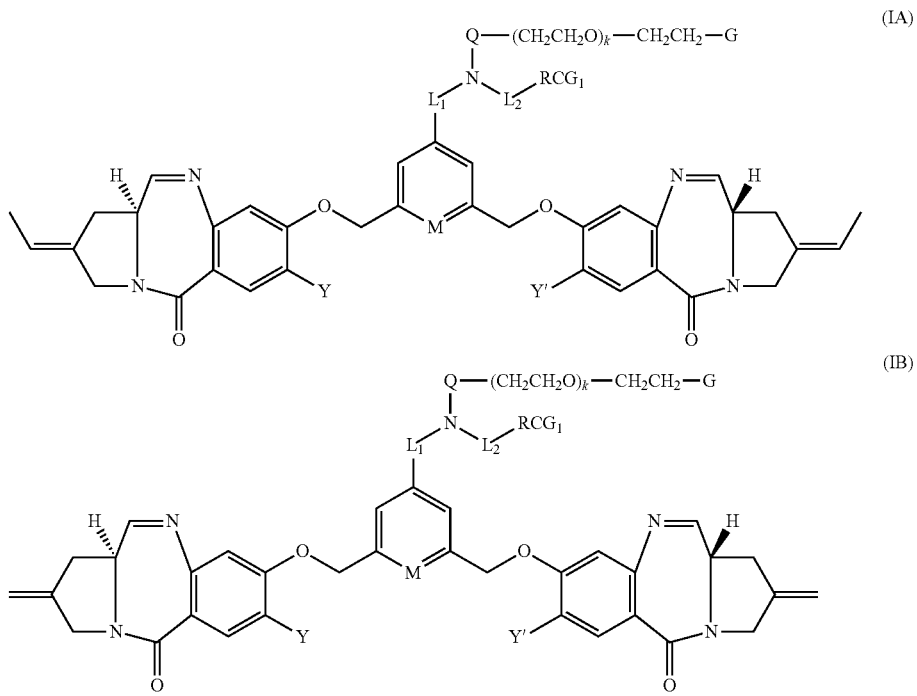

More particularly, $R_1$ and $R_2$ and/or $R_1$' and $R_2$' together form, respectively, a double bond =$CH_2$ or =CH—$CH_3$, more specifically =CH—$CH_3$.

G may represent a group —OR, more particularly a group —OH or —O($C_1$-$C_6$)alkyl, especially —OMe. G may also represent a group —NRR' in which R and R' represent, independently of each other, H or a group ($C_1$-$C_6$)alkyl. More particularly, G may thus represent a group —$NH_2$, —NH($C_1$-$C_6$)alkyl or —N($C_1$-$C_6$)alkyl$_2$, especially —N($CH_3$)$_2$. G may also represent a group —NRR' in which R and R' form, together with the nitrogen atom to which they are attached, a group ($C_4$-$C_{10}$)heterocycloalkyl which may comprise in the Furthermore, the following are distinguished:
a first subgroup of compounds for which $L_1$=-D-($C_1$-$C_6$)ALK- and $L_2$=—($C_1$-$C_6$)ALK-;
a second subgroup of compounds for which $L_1$=—(O$CH_2CH_2$)$_i$— and $L_2$=—($C_1$-$C_6$)ALK-;
a third subgroup of compounds for which $L_1$=single bond and $L_2$=—(C$H_2CH_2$O)$_j$—$CH_2CH_2$NR"—($C_1$-$C_6$)ALK-;
a fourth subgroup of compounds for which $L_1$=-D-($C_1$-$C_6$)ALK-, and $L_2$=—(C$H_2CH_2$O)$_j$—$CH_2CH_2$NR"—($C_1$-$C_6$)ALK-;

a fifth subgroup of compounds for which $L_1$=-D-($C_1$-$C_6$)ALK- and $L_2$=—(CH$_2$CH$_2$O)$_j$—CH$_2$CH$_2$—

The following groups of compounds may also be distinguished:

- $L_1$=-D-($C_1$-$C_6$)ALK-, $L_2$=—($C_1$-$C_6$)ALK-, Q=single bond, k=1-10, G=OR, RCG1=—$SZ_a$;
- $L_1$=-D-($C_1$-$C_6$)ALK-, $L_2$=—($C_1$-$C_6$)ALK-, Q=CO, k=1-10, G=OR, RCG1=—$SZ_a$;
- $L_1$=—(OCH$_2$CH$_2$)$_i$—, $L_2$=—($C_1$-$C_6$)ALK-, Q=single bond, k=1-10, G=OR, RCG1=—$SZ_a$;
- $L_1$=—(OCH$_2$CH$_2$)$_i$—, $L_2$=—($C_1$-$C_6$)ALK-, Q=CO, k=1-10, G=OR, RCG1=—$SZ_a$;
- $L_1$=-D-($C_1$-$C_6$)ALK-, $L_2$=—($C_1$-$C_6$)ALK-, Q=single bond, k=1-10, G=NRR', RCG1=—$SZ_a$;
- $L_1$=-D-($C_1$-$C_6$)ALK-, $L_2$=—($C_1$-$C_6$)ALK-, Q=CO, k=1-10, G=NRR', RCG1=—$SZ_a$;
- $L_1$=single bond, $L_2$=—(CH$_2$CH$_2$O)$_j$—CH$_2$CH$_2$NR"—($C_1$-$C_6$)ALK-, Q=single bond, k=1-10, G=OR, RCG1=—$SZ_a$;
- $L_1$=single bond, $L_2$=—(CH$_2$CH$_2$O)$_j$—CH$_2$CH$_2$NR"—($C_1$-$C_6$)ALK-, Q=CO, k=1-10, G=OR, RCG1=—$SZ_a$;
- $L_1$=single bond, $L_2$=—(CH$_2$CH$_2$O)$_j$—CH$_2$CH$_2$NR"—($C_1$-$C_6$)ALK-, Q=single bond, k=0-10, G=NRR', RCG1=—$SZ_a$;
- $L_1$=single bond, $L_2$=—(CH$_2$CH$_2$O)$_j$—CH$_2$CH$_2$NR"—($C_1$-$C_6$)ALK-, Q=CO, k=0-10, G=NRR', RCG1=—$SZ_a$;
- $L_1$=-D-($C_1$-$C_6$)ALK-, $L_2$=—(CH$_2$CH$_2$O)$_j$—CH$_2$CH$_2$NR"—($C_1$-$C_6$)ALK-, Q=single bond, k=0-10, G=NRR', RCG1=—$SZ_a$;
- $L_1$=-D-($C_1$-$C_6$)ALK-, $L_2$=—(CH$_2$CH$_2$O)—CH$_2$CH$_2$NR"—($C_1$-$C_6$)ALK-, Q=CO, k=0-10, G=NRR', RCG1=—$SZ_a$;
- $L_1$=-D-($C_1$-$C_6$)ALK-, $L_2$=—(CH$_2$CH$_2$O)$_j$—CH$_2$CH$_2$NR"—($C_1$-$C_6$)ALK-, Q=single bond, k=1-10, G=OR, RCG1=—$SZ_a$;
- $L_1$=-D-($C_1$-$C_6$)ALK-, $L_2$=—(CH$_2$CH$_2$O)$_j$—CH$_2$CH$_2$NR"—($C_1$-$C_6$)ALK-, Q=CO, k=1-10, G=OR, RCG1=—$SZ_a$;
- $L_1$=-D-($C_1$-$C_6$)ALK-, $L_2$=—($C_1$-$C_6$)ALK-, Q=single bond, k=1-10, G=OR, RCG1=—C(=O)$Z_b R_b$;
- $L_1$=-D-($C_1$-$C_6$)ALK-, $L_2$=—($C_1$-$C_6$)ALK-, Q=CO, k=1-10, G=OR, RCG1=—C(=O)$Z_b R_b$;
- $L_1$=-D-($C_1$-$C_6$)ALK-, $L_2$=—($C_1$-$C_6$)ALK-, Q=single bond, k=1-10, G=NRR', RCG1=—C(=O)$Z_b R_b$;
- $L_1$=-D-($C_1$-$C_6$)ALK-, $L_2$=—($C_1$-$C_6$)ALK-, Q=CO, k=1-10, G=NRR', RCG1=—C(=O)$Z_b R_b$;
- $L_1$=—(OCH$_2$CH$_2$)$_i$—, $L_2$=—($C_1$-$C_6$)ALK-, Q=single bond, k=1-10, G=OR, RCG1=—C(=O)$Z_b R_b$;
- $L_1$=—(OCH$_2$CH$_2$)$_i$—, $L_2$=—($C_1$-$C_6$)ALK-, Q=CO, k=1-10, G=OR, RCG1=—C(=O)$Z_b R_b$;
- $L_1$=—(OCH$_2$CH$_2$)$_i$—, $L_2$=—($C_1$-$C_6$)ALK-, Q=single bond, k=1-10, G=NRR', RCG1=—C(=O)$Z_b R_b$;
- $L_1$=—(OCH$_2$CH$_2$)$_i$—, $L_2$=—($C_1$-$C_6$)ALK-, Q=CO, k=1-10, G=NRR', RCG1=—C(=O)$Z_b R_b$;
- $L_1$=-D-($C_1$-$C_6$)ALK-, $L_2$=—(CH$_2$CH$_2$O)$_j$—CH$_2$CH$_2$—, Q=single bond, k=1-10, G=OR, RCG1=—C(=O)$Z_b R_b$;
- $L_1$=-D-($C_1$-$C_6$)ALK-, $L_2$=—(CH$_2$CH$_2$O)$_j$—CH$_2$CH$_2$—, Q=CO, k=1-10, G=OR, RCG1=—C(=O)$Z_b R_b$;
- $L_1$=-D-($C_1$-$C_6$)ALK-, $L_2$=—(CH$_2$CH$_2$O)—CH$_2$CH$_2$—, Q=single bond, k=0-10, G=NRR', RCG1=—C(=O)$Z_b R_b$;
- $L_1$=-D-($C_1$-$C_6$)ALK-, $L_2$=—(CH$_2$CH$_2$O)—CH$_2$CH$_2$—, Q=CO, k=0-10, G=NRR', RCG1=—C(=O)$Z_b R_b$.

In the groups of compounds defined above:
i more particularly represents an integer ranging from 2 to 10, especially an integer equal to 3;
j more particularly represents an integer ranging from 1 to 10, especially an integer equal to 2 or 3;
k more particularly represents an integer equal to 0, or ranging from 1 to 5.

Table I describes particular linkers L and also examples of compounds corresponding thereto. Each compound of this table may exist in the form with M=CH (benzene) or alternatively M=N (pyridine). The compounds with M=N are more water-soluble. In this table, the examples are given in a form (IA) but may also exist in a form (IB). L, $L_1$, $L_2$, k and G may be chosen from those described in Table I or among the examples.

TABLE I

| L₁ | L₂ | Q | G | Compound of formula (IA) | n° |
|---|---|---|---|---|---|
| —D—ALK— | ALK | — | OR | (structure) | 1 |
| —D—ALK— | ALK | CO | OR | (structure) | 2 |

TABLE I-continued

| L₁ | L₂ | Q | G | Compound of formula (IA) | n° |
|---|---|---|---|---|---|
| —D—ALK— | ALK | — | OR | | 3 |
| —D—ALK— | ALK | CO | OR | | 4 |
| —(OCH₂CH₂)ₜ— | ALK | — | OR | | 5 |

TABLE I-continued

| L₁ | L₂ | Q | G | Compound of formula (IA) | n° |
|---|---|---|---|---|---|
| —(OCH₂CH₂)ᵣ— | ALK | CO | OR | | 6 |
| —D—ALK— | ALK | | NRR' | | 7 |
| —D—ALK— | ALK | CO | NRR' | | 8 |

TABLE I-continued

| L1 | L2 | Q | G | Compound of formula (IA) | n° |
|---|---|---|---|---|---|
| —D—ALK— | ALK | — | OR | (structure) | 9 |
| —D—ALK— | ALK | CO | OR | (structure) | 10 |
| single bond | —(CH$_2$CH$_2$O)$_j$—CH$_2$CH$_2$NR''—ALK— | — | OR | (structure) | 11 |

TABLE I-continued

Compound of formula (IA)

| L1 | L2 | Q | G | n° |
|---|---|---|---|---|
| single bond | —(CH₂CH₂O)ⱼ—CH₂CH₂NR"—ALK— | CO | OR | 12 |
| —D—ALK— | —(CH₂CH₂O)ⱼ—CH₂CH₂NR"—ALK— | — | OR | 13 |
| —D—ALK— | —(CH₂CH₂O)ⱼ—CH₂CH₂NR"—ALK— | CO | OR | 14 |

TABLE I-continued

| L₁ | L₂ | Q | G | Compound of formula (IA) | n° |
|---|---|---|---|---|---|
| single bond | —(CH₂CH₂O)ⱼ—CH₂CH₂NR″—ALK— | — | NRR' | | 15 |
| single bond | —(CH₂CH₂O)ⱼ—CH₂CH₂NR″—ALK— | CO | NRR' | | 16 |
| —D—ALK— | —(CH₂CH₂O)ⱼ—CH₂CH₂NR″—ALK— | — | NRR' | | 17 |

TABLE I-continued
| L1 | L2 | Q | G | Compound of formula (IA) | n° |
|---|---|---|---|---|---|
| —D—ALK— | —(CH$_2$CH$_2$O)$_j$—CH$_2$CH$_2$NR''—ALK— | CO | NRR' | 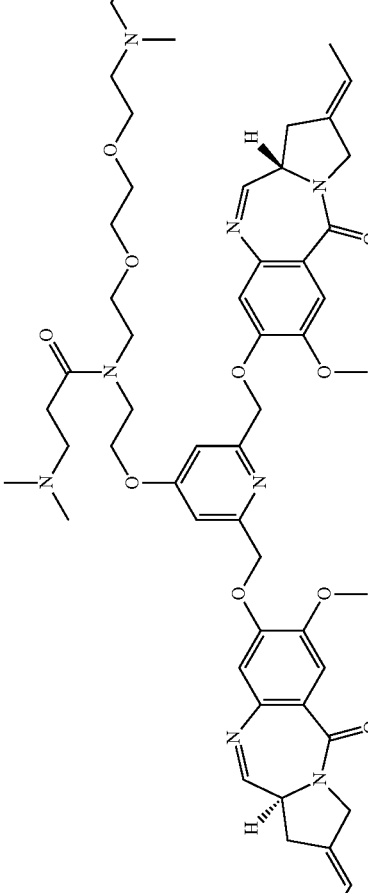 | 18 |
| —D—ALK— | ALK | — | NRR' | 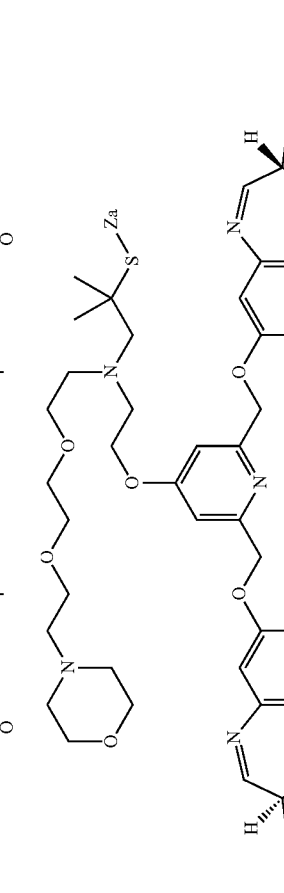 | 19 |

TABLE I-continued

| L₁ | L₂ | Q | G | Compound of formula (IA) | n° |
|---|---|---|---|---|---|
| —D—ALK— | ALK | — | OR | (structure) | 20 |
| —D—ALK— | ALK | — | OR | (structure) | 21 |
| —D—ALK— | ALK | CO | OR | (structure) | 22 |

TABLE I-continued

| L1 | L2 | Q | G | Compound of formula (IA) | n° |
|---|---|---|---|---|---|
| —D—ALK— | ALK | CO | OR | | 23 |
| —D—ALK— | ALK | — | OR | | 24 |
| —D—ALK— | ALK | CO | OR | | 25 |

TABLE I-continued

| L₁ | L₂ | Q | G | Compound of formula (IA) | n° |
|---|---|---|---|---|---|
| —(OCH₂CH₂)ₜ— | ALK | — | OR | | 26 |
| —(OCH₂CH₂)ₜ— | ALK | CO | OR | | 27 |
| —D—ALK— | ALK | — | NRR' | | 28 |

TABLE I-continued

| L₁ | L₂ | Q | G | Compound of formula (IA) | n° |
|---|---|---|---|---|---|
| —D—ALK— | ALK | CO | NRR' | | 29 |
| —D—ALK— | ALK | — | OR | | 30 |
| —D—ALK— | ALK | CO | OR | | 31 |

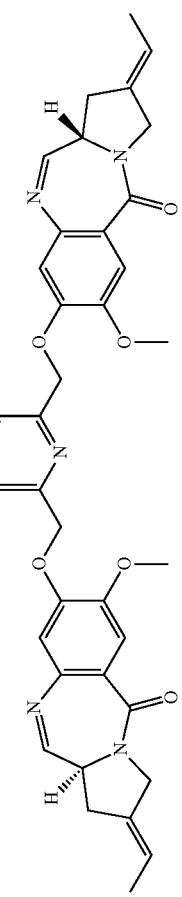

TABLE I-continued

| L₁ | L₂ | Q | G | Compound of formula (IA) | n° |
|---|---|---|---|---|---|
| —D—ALK— | —(CH₂CH₂O)ⱼ—CH₂CH₂— | — | NRR' | | 34 |
| —D—ALK— | —(CH₂CH₂O)ⱼ—CH₂CH₂— | CO | NRR' | | 35 |

TABLE I-continued
| L1 | L2 | Q | G | Compound of formula (IA) | n° |
|---|---|---|---|---|---|
| —D—ALK— | ALK | CO | NRR' | 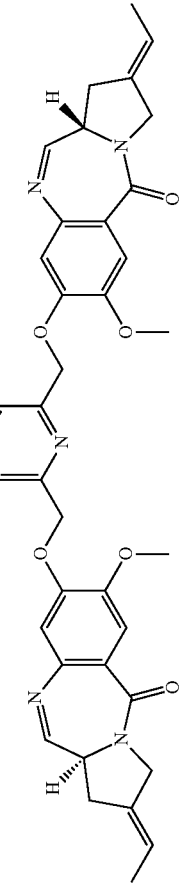 | 36 |

The compounds described comprise a reactive chemical group (RCG1) that is reactive towards a reactive chemical group (RCG2) present on the binding agent. The reaction between RCG1 and RCG2 brings about the attachment of the compound of formula (I) to the binding agent by formation of a covalent bond. Thus, the compounds of formula (I) can be conjugated to a binding agent.

RCG1 represents:

(i) the reactive group —$SZ_a$ for which $Z_a$ represents H or the group —$SR_a$ and $R_a$ representing a group ($C_1$-$C_6$)alkyl, ($C_3$-$C_7$)Cycloalkyl, aryl, heteroaryl or ($C_4$-$C_{10}$)heterocycloalkyl;

(ii) the reactive group —C(=O)—$Z_bR_b$ for which $Z_b$ represents a single bond, —O— or —NH—, more particularly —O—, and $R_b$ representing H or a group ($C_1$-$C_6$)alkyl, ($C_3$-$C_7$)cycloalkyl, aryl, heteroaryl or ($C_4$-$C_{10}$)heterocycloalkyl.

More particularly, —$SZ_a$ may represent —SH or —SS($C_1$-$C_6$)alkyl, especially —SSMe, or —SS-heteroaryl, especially

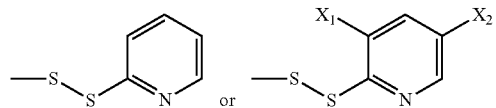

($X_1$ and $X_2$ being defined hereinbelow). More particularly, —$SZ_a$ may represent —SH or —SS($C_1$-$C_6$)alkyl, especially —SSMe.

More particularly, —$Z_bR_b$ may represent —OH (acid function), —O($C_1$-$C_6$)alkyl, especially —$OCH_3$, —$OCH_2CH_3$, —$OCH_2CH=CH_2$ (ester function) or alternatively —$Z_bR_b$ may represent

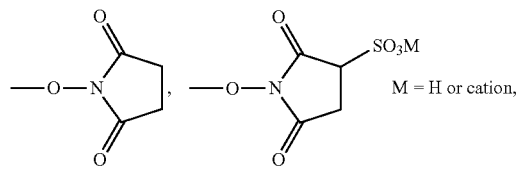

M = H or cation,

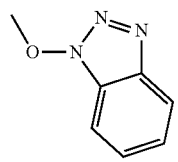

or the group

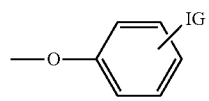

in which IG represents at least one electroinductive group such as —$NO_2$ or -Hal, especially —F. It may be, for example, one of the following groups:

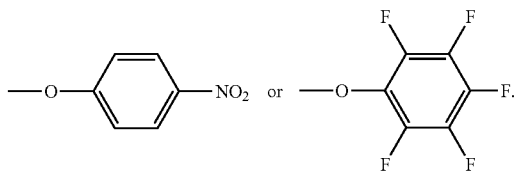

Another type of group —C(=O)$Z_bR_b$ is the following:

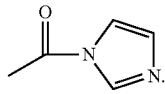

The reactive groups —SH and

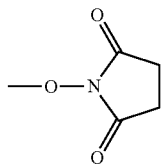

show good reactivity.

More particularly, —$Z_bR_b$ may represent —OH (acid function), —O($C_1$-$C_6$)alkyl, especially —$OCH_3$, —$OCH_2CH_3$, or alternatively —$Z_bR_b$ may represent

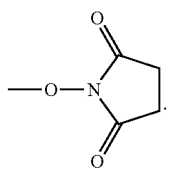

More particularly, RCG1 may be chosen from one of those described in the examples.

As examples of RCG2, mention may be made of the ε-amino groups of lysines borne by the side chains of lysine residues that are present at the surface of an antibody, the saccharide groups of the hinge region or the thiols of cysteines by reduction of intra-chain disulfide bonds (Garnett M. C. et al., *Advanced Drug Delivery Reviews* 2001, 53, 171-216). More recently, other approaches have been considered, such as the introduction of cysteines by mutation (Junutula J. R. et al., *Nature Biotechnology* 2008, 26, 925-932; WO 09026274) or the introduction of unnatural amino acids allowing other types of chemistry (de Graaf A. J. et al., *Bioconjugate Chem.* 2009, Publication Date (Web): Feb. 3, 2009 (Review); DOI: 10.1021/bc800294a; WO 2006/069246 and according to Chin J. W. et al., *JACS* 2002, 124, 9026-9027 (ReCode® technology)). These modes of attachment used with antibodies are applicable to all the known targeting agents as a function of their structure.

It is also possible to chemically modify the targeting agent so as to introduce novel reactive chemical groups RCG2. Thus, it is well known to those skilled in the art how to modify an antibody using a modifying agent (see especially WO 2005/077090 page 14). The modification makes it possible to improve the conjugation reaction and to use a wider variety of groups RCG1.

Modifying Agents for Introducing Disulfide Groups

The modifying agent may be an activated ester NHS of formula

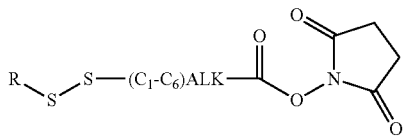

in which R represents a group ($C_1$-$C_6$)alkyl, aryl, heteroaryl, ($C_3$-$C_7$)cycloalkyl, ($C_4$-$C_{10}$)heterocycloalkyl; for example, it is possible to use N-pyridyldithiopropionate (SPDP) or N-succinimidyl pyridyldithiobutyrate (SPDB or the N-hydroxysuccinimidyl ester of 4-(2-pyridyldithio)butanoic acid) so as to introduce dithiopyridyl reactive groups RCG2 (see Bourdon M. A. et al., *Biochem. J.* 1978, 173, 723-737; U.S. Pat. No. 5,208,020) which can then react with a reactive chemical group RCG1 of the type —SH present on the linker of the pyrrolo[1,4]benzodiazepine dimer so as to form a new —S—S— bond (see Ex. 1) for a conjugate bearing a disulfide bond. The N-hydroxysuccinimide group preferentially reacts on the amino groups present on the antibody so as to form amide bonds. Another example of a modifying agent is described in WO 2004/016801 of formula

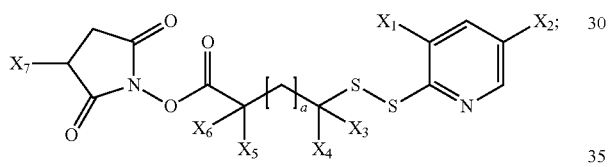

for example, it is possible to use N-succinimidyl 4-(5-nitro-2-pyridyldithio)pentanoate (SNPP), or a pegylated analogue of formula

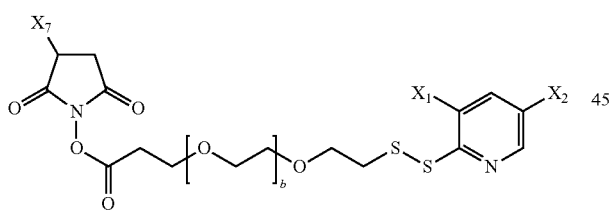

described in WO 2009/134976 or a sulfonic analogue of formula

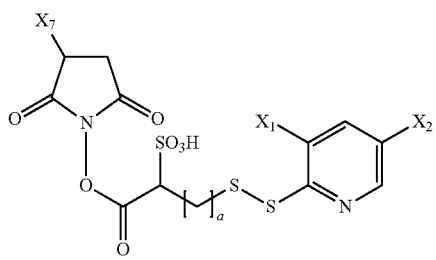

described in WO 2009/134977, in which formulae:

$X_3$, $X_4$, $X_5$, $X_6$ represent H or a group ($C_1$-$C_6$)alkyl, $X_1$ and $X_2$ represent —H, —CONX$_8$X$_9$, —NO$_2$, $X_8$ and $X_9$ representing H or a group ($C_1$-$C_6$)alkyl, $X_7$ represents —SO$_3^-$M$^+$ or H or alternatively a quaternary ammonium group;

a denotes an integer ranging from 0 to 4 and b denotes an integer ranging from 0 to 2000, preferably between 1 and 200; a and b may take all the values between, respectively, 0 and 4 or between 0 and 2000.

Preferably, among the compounds of formula

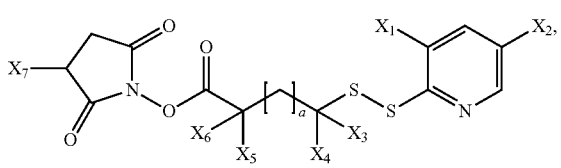

a=1, $X_3$=Me and $X_2$=NO$_2$ and $X_1$=$X_4$=$X_5$=$X_6$=$X_7$=H).

Modifying Agents for Introducing Maleimido Groups

Another modifying agent may be an activated ester NHS of formula

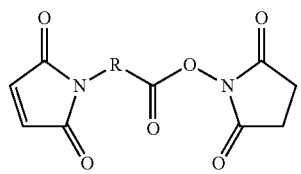

in which R represents a group —(CH$_2$)$_n$—, —(CH$_2$)$_n$-cyclohexyl-, -cyclohexyl-(CH$_2$)$_n$— and n represents an integer ranging from 1 to 10; for example, it is possible to use succinimidyl-4-(N-maleimidomethyl)cyclohexane-1-carboxylate (SMCC) (according to EP 0306943), or a sulfo-SMCC (sulfosuccinimidyl 4-(N-maleimidomethyl)cyclohexane-1-carboxylate). Other examples that may be mentioned include:

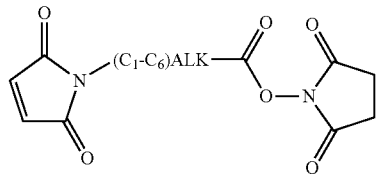

such as N-succinimidyl 3-maleimidopropanoate;

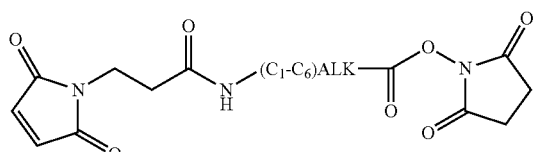

for instance N-succinimidyl 6-(3-maleimidopropionamido)hexanoate;

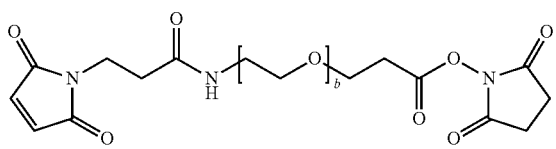

b being an integer between 0 and 2000, preferably between 1 and 200 (b may take all the values between 0 and 2000), for instance N-succinimidyl 3-(2-{2-[3-maleimidopropionylamino]-ethoxy}ethoxy)propanoate or SM(PEG)$_2$;

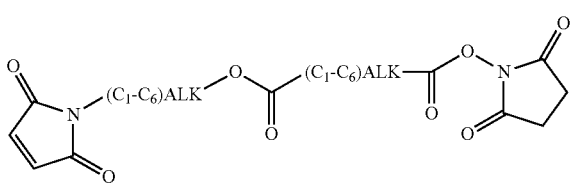

for instance maleimidoethyl N-succinimidyl succinate;

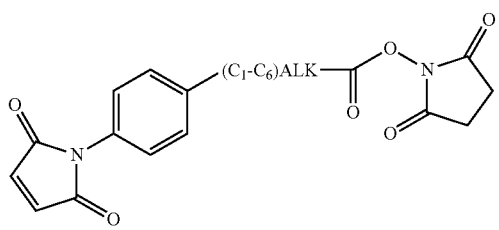

for instance N-succinimidyl 4-(4-maleimidophenyl)butanoate or

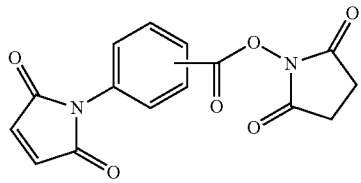

for instance N-succinimidyl 3-maleimidobenzoate.

Modifying Agents for Introducing Thiol Groups

Another example of a modifying agent described in WO 90/06774 has the formula

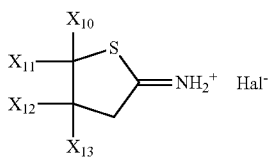

in which:
Hal represents a halogen atom;
$X_{10}$ represents a halogen atom or the group $COOX_{14}$, nitro, unsubstituted or halogenated ($C_1$-$C_8$)alkyl, unsubstituted or halogenated ($C_1$-$C_8$)alkoxy, unsubstituted or halogenated ($C_2$-$C_8$)alkenyl, unsubstituted or halogenated ($C_2$-$C_8$) alkynyl, unsubstituted ($C_3$-$C_8$)cycloalkyl, aryl which is unsubstituted or substituted with one to three substituents selected from amino, a halogen atom, an unsubstituted or halogenated group ($C_1$-$C_8$)alkyl, or an unsubstituted or halogenated ($C_1$-$C_8$)alkoxy;

each of the groups $X_{11}$, $X_{12}$, $X_{13}$ independently represents a hydrogen atom or alternatively may represent $X_{10}$;
or $X_{10}$ and $X_{11}$ together form a ($C_2$-$C_5$)alkylene ring, which is unsubstituted or substituted with one to five groups ($C_1$-$C_4$) alkyl;
or $X_{10}$ or $X_{11}$ form, together with $X_{12}$, a ($C_1$-$C_5$)alkylene ring, which is unsubstituted or substituted with one to five groups ($C_1$-$C_4$) alkyl;
and $X_{14}$ is —H or a group ($C_1$-$C_8$)alkyl;
or $X_{10}$=$X_{11}$=$X_{12}$=$X_{13}$=H.

Preferably, Hal represents a chlorine or bromine atom.
Possibilities for $X_{10}$-$X_{13}$ will be found in the table below:

| $X_{10}$ | $X_{11}$ | $X_{12}$ | $X_{13}$ | Hal |
|---|---|---|---|---|
| Me | H | H | H | Cl |
| Ph | H | H | H | Cl |
| t-Bu | H | H | H | Cl |
| Me | Me | H | H | Cl |
| (—CH$_2$(CH$_2$)$_3$CH$_2$—) | | H | H | Cl |
| H | (—CH$_2$(CH$_2$)$_3$CH$_2$—) | | H | Cl |
| Et | H | H | H | Br |
| Et | Me | H | H | Cl |
| —CH—CH$_2$—CH— | H | H | H | Cl |
| Me | H | Me | H | Cl |
| H | H | Me | Me | Cl |
| Ph | Me | H | H | Cl |
| 4-ClPh | H | H | H | Cl |
| 3-furanyl | H | H | H | Cl |
| i-Pr | H | H | H | Cl |
| Me | Me | Me | Me | Cl |
| C$_6$H$_{11}$ | H | H | H | Cl |
| CH$_2$Br | H | H | H | Cl |
| CF$_3$ | H | H | H | Cl |
| CH=CH$_2$ | H | H | H | Cl |
| 2-NH$_2$Ph | H | H | H | Cl |

An example of a preferred iminothiolane is the following:

D

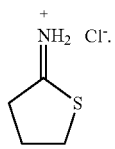

Modifying Agents for Introducing Haloacetamido Groups

Another example of a modifying agent is succinimidyl-4-(N-iodoacetyl)aminobenzoate (SIAB)

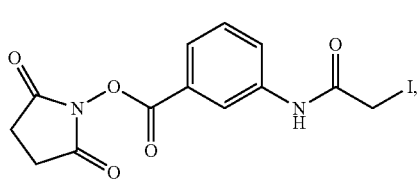 [SMILES: O=C(CI)Nc1cccc(C(=O)ON2C(=O)CCC2=O)c1]

or similar compounds, including succinimidyl-N-iodoacetate (SIA)

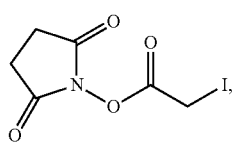 [SMILES: O=C(CI)ON1C(=O)CCC1=O]

succinimidyl-N-bromoacetate (SBA), or succinimidyl-3-(N-bromoacetamido)propionate (SBAP) or a similar pegylated compound described in WO 2009/134976

Figure 2:
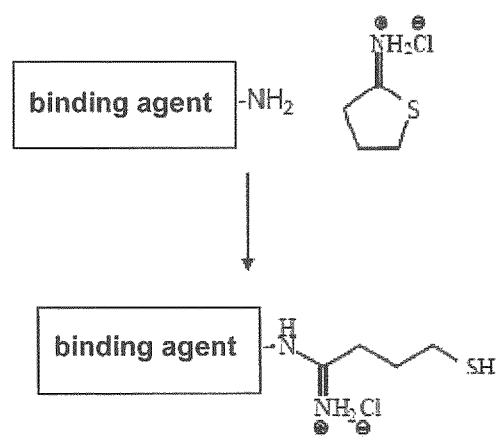
FIG. 2 shows modification of the binding agent by an iminothiolane.
Figure 3:
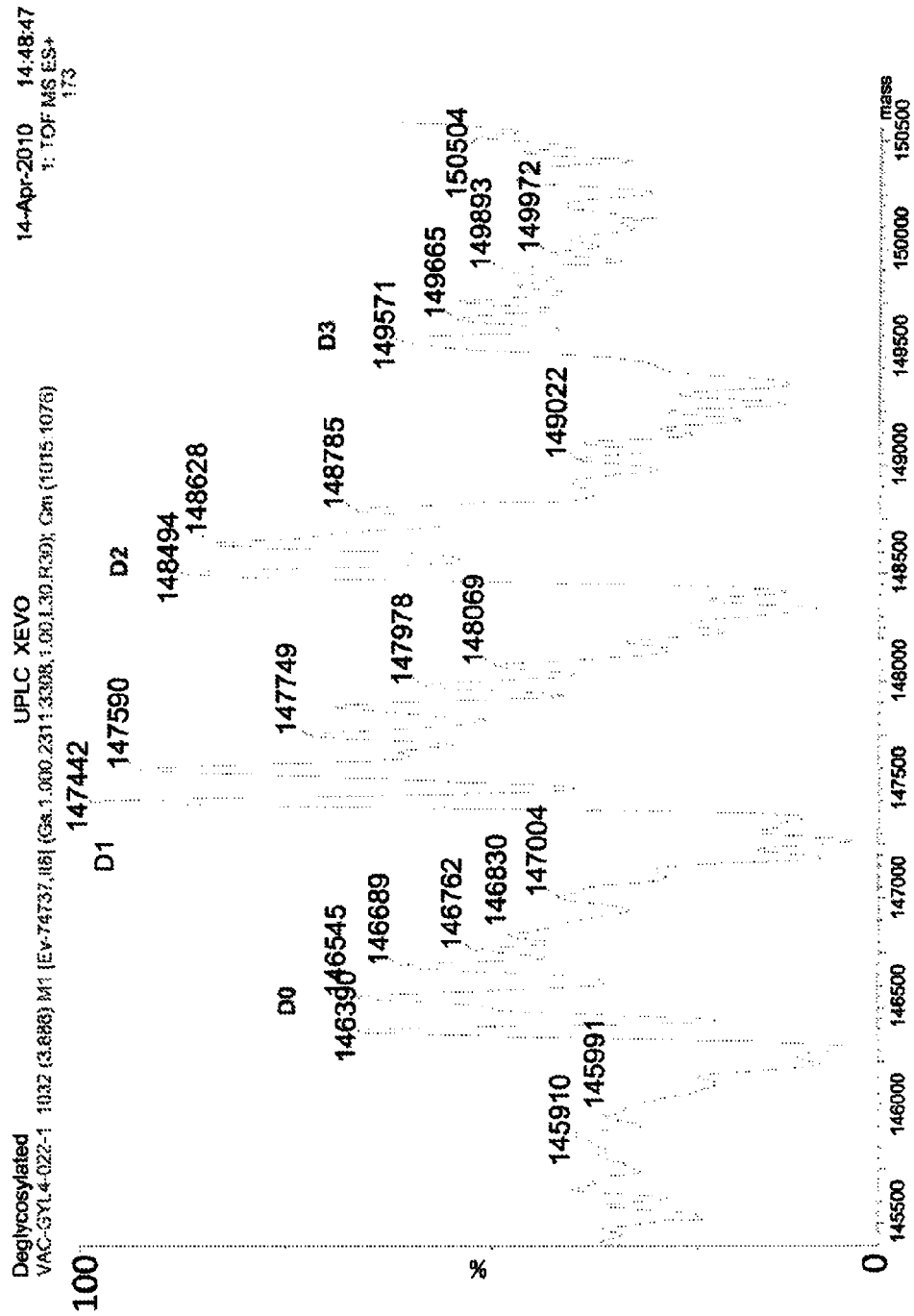
FIG. 3 shows deconvoluted high resolution mass spectrum of the conjugate of Ex. 8 after deglycosylation.
Figure 4:
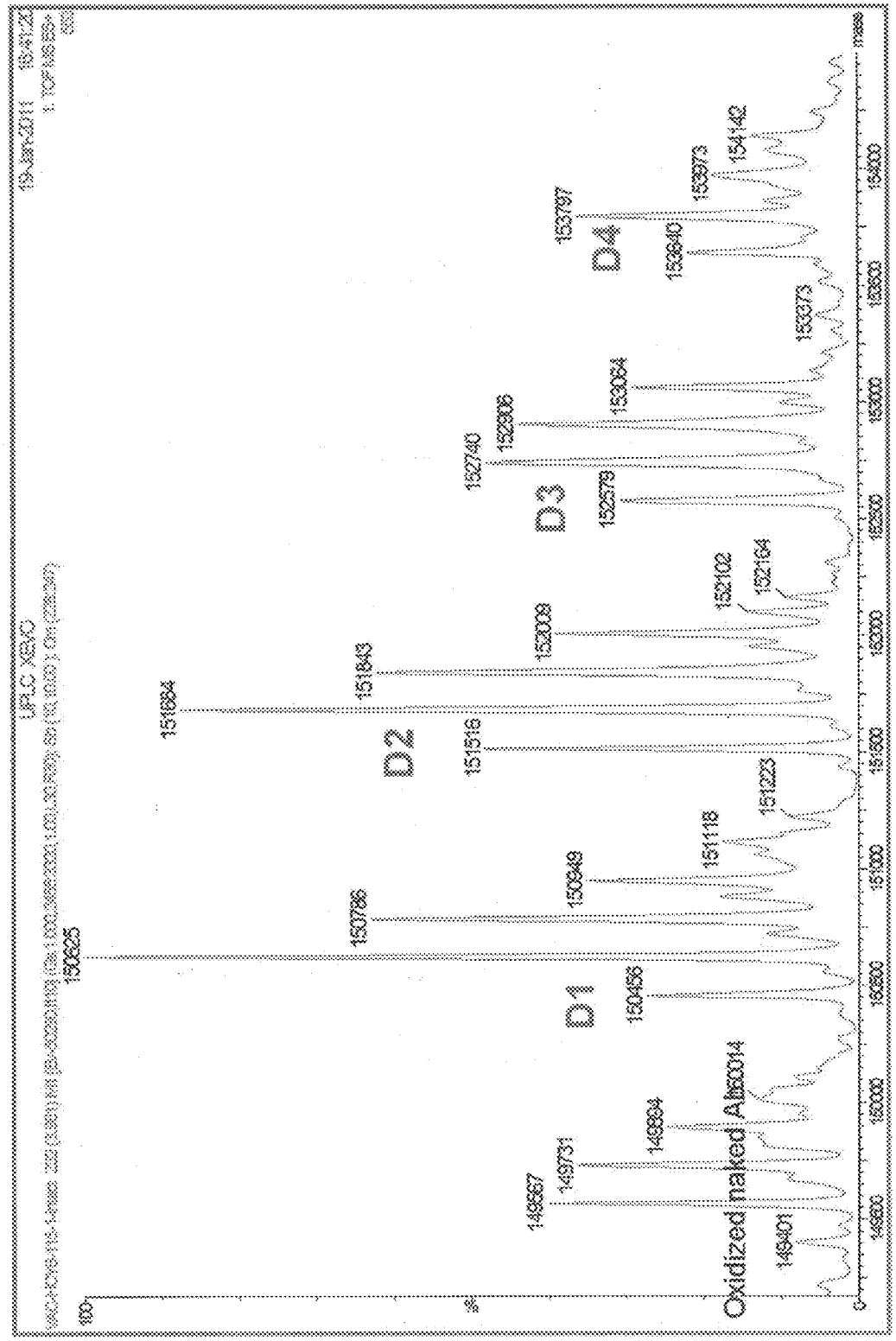
FIG. 4 shows deconvoluted high resolution mass spectrum (HRMS) of the non-deglycosylated conjugate of Ex. 9.
Figure 5:
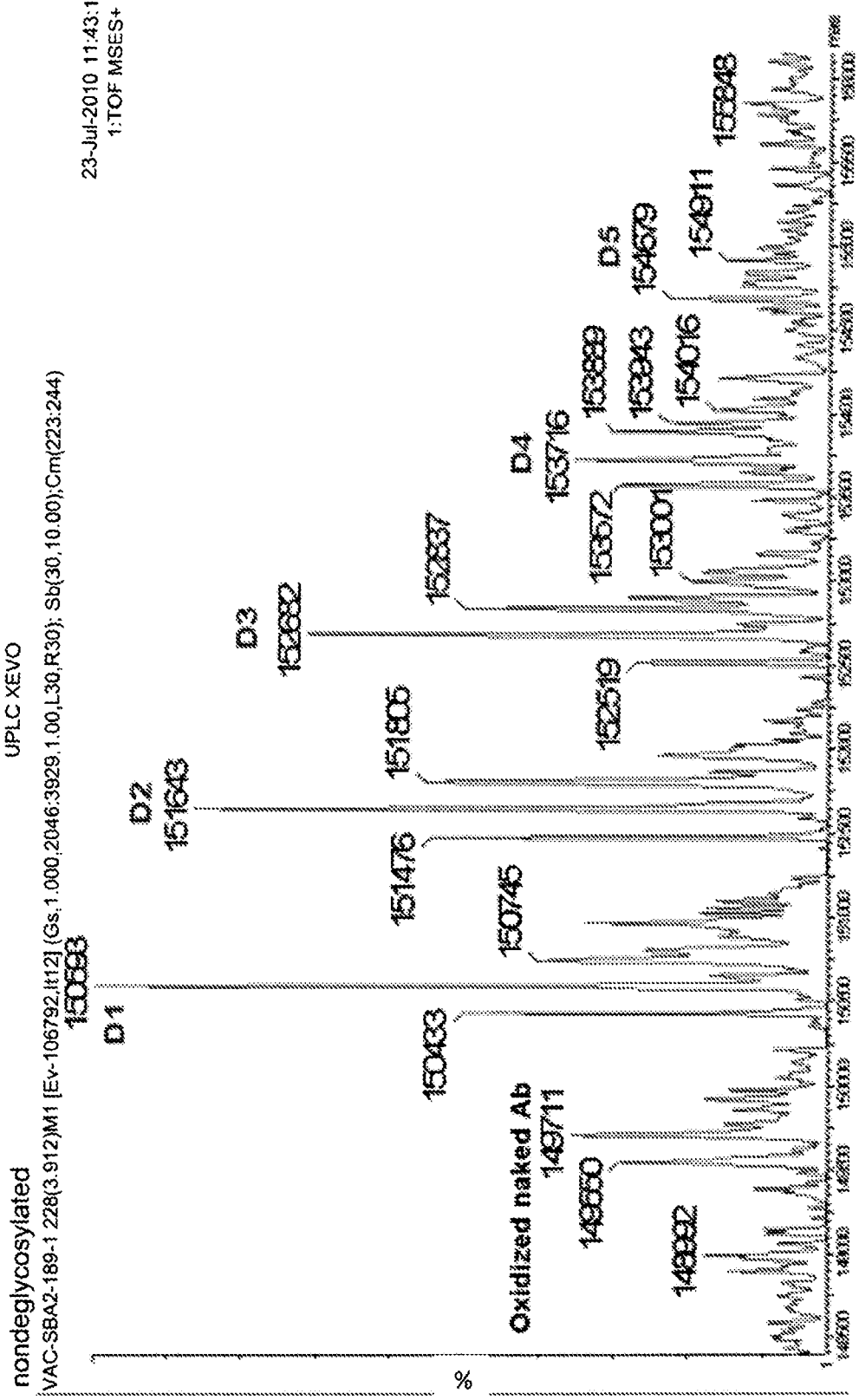
FIG. 5 shows deconvoluted high resolution mass spectrum (HRMS) of the non-deglycosylated conjugate of Ex. 10.
Figure 6:
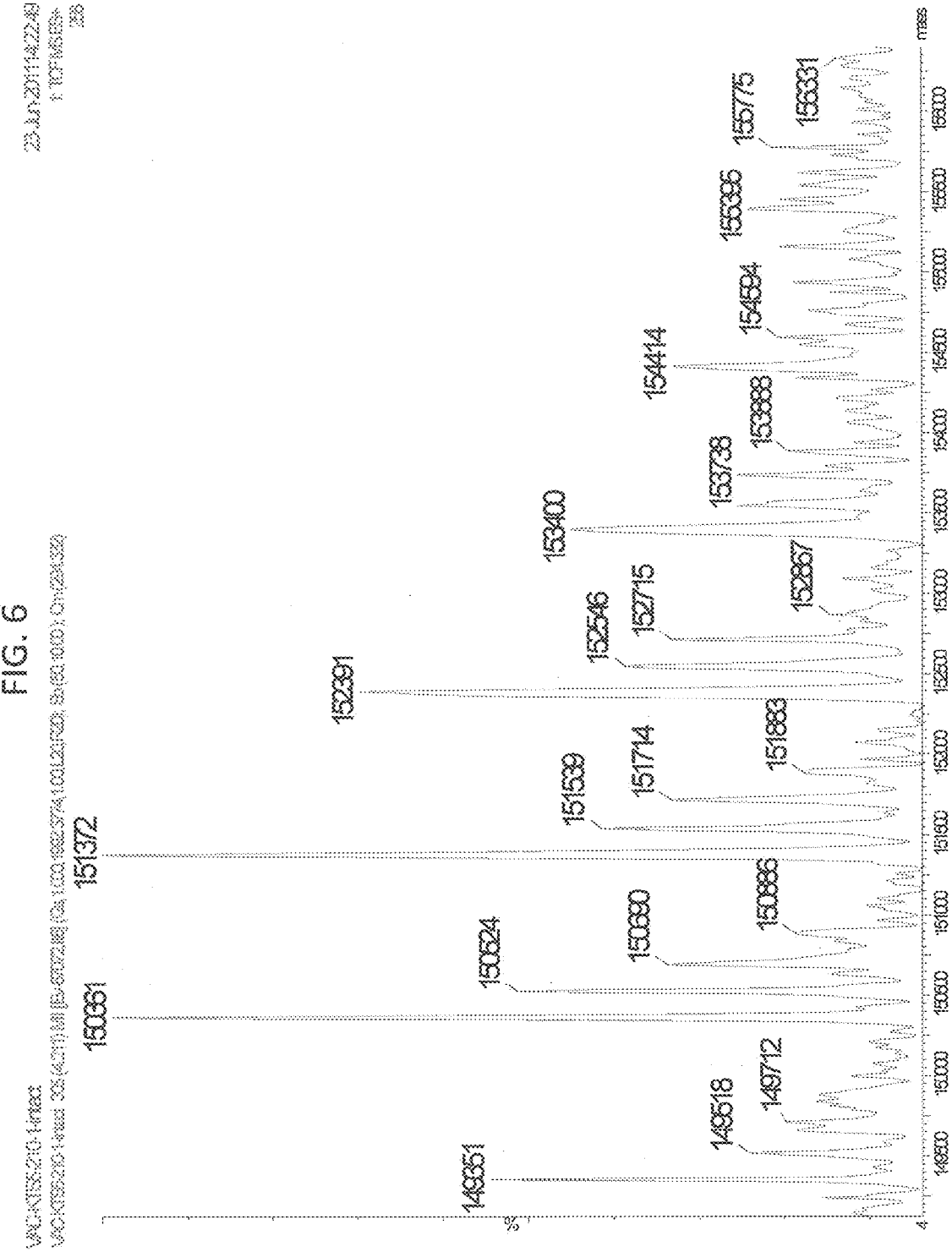
FIG. 6 shows deconvoluted high resolution mass spectrum (HRMS) of the non-deglycosylated conjugate of Ex. 11.
These figures show for each conjugate the distribution of the species bearing from 0 to 8 tomaymycin dimers ($D_0$: no dimers; $D_x$: x dimers).

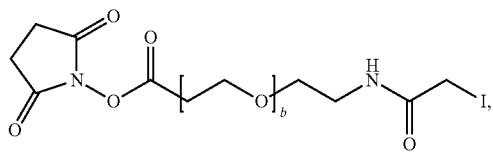

b being as described previously. FIGS. 1 and 2 illustrate the modification of an amino group of a binding agent with SPDP or alternatively the preferred iminothiolane above.

Thus, it is possible to introduce onto the binding agent disulfide RCG2 groups (—SSR), especially of pyridyldisulfide type

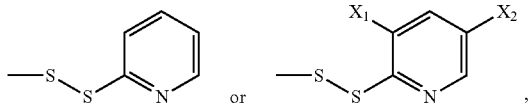

in the case where RCG1 represents —SH. Similarly, it is possible to introduce onto the binding agent thiol (—SH) RCG2 groups, for example with an iminothiolane, in the case where RCG1 represents disulfide (i.e. RCG1=—SZ$_a$ with Z$_a$≠H, for example

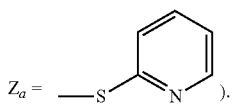

It is also possible to modify these thiol (—SH) RCG2 groups into disulfide (—SSR) RCG2 groups, especially of pyridyldisulfide type

by reaction with the corresponding aromatic disulfides

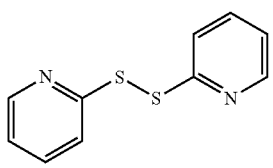

or

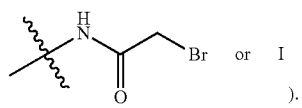

In both cases, the covalent bond that forms by reaction between RCG1 and RCG2 is a cleavable disulfide bond.

It is also possible, in the case where RCG1 represents —SH, to introduce at the surface of the binding agent RCG2 groups of maleimido

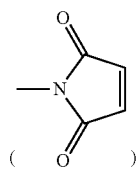

or haloacetamido type (e.g. bromo- or iodoacetamido

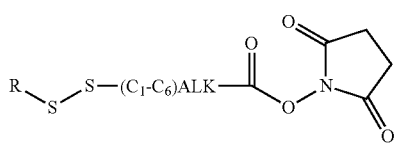

).

In this case, the covalent bond that forms by reaction between RCG1 and RCG2 is an uncleavable sulfide bond.

Thus,
in the presence of a derivative of formula (I) comprising a reactive chemical group RCG1 of the type —SZ$_a$, the binding agent comprises:
disulfide chemical groups in the case where RCG1 represents —SH;
thiol chemical groups in the case where RCG1 represents —SZ$_a$ with Z$_a$≠H;
maleimido or haloacetamido chemical groups in the case where RCG1 represents —SH;
in the presence of a derivative of formula (I) comprising a reactive chemical group RCG1 of the type —C(=O)—Z$_b$R$_b$, the derivative of formula (I) is reacted with the amino functions of the binding agent, especially the ε-amino groups borne by the side chains of the lysine (Lys) residues of an antibody.

More particularly,
when the reactive chemical group RCG1 is of the type —SH, and when the binding agent bears amino functions, especially ε-amino groups borne by the side chains of the lysine residues of an antibody, the latter is modified by means of a modifying agent chosen from a compound of formula:

in which R represents a group $(C_1-C_6)$alkyl, aryl, heteroaryl, $(C_3-C_7)$cycloalkyl, $(C_4-C_{10})$heterocycloalkyl;

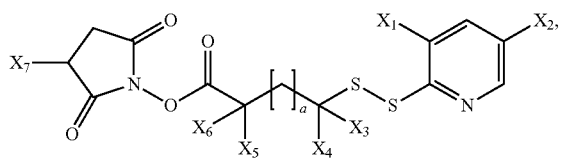

a pegylated analogue of formula:

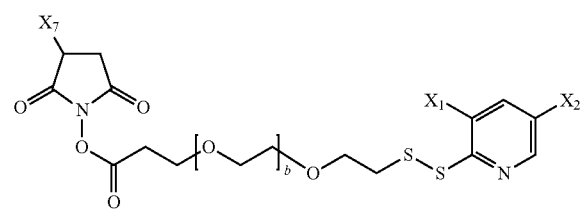

or a sulfonic analogue of formula

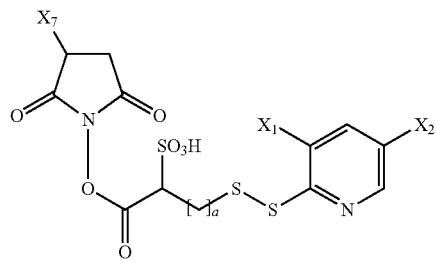

in which $X_3$ $X_4$, $X_5$, $X_6$ represent H or a group $(C_1-C_6)$alkyl, $X_1$ and $X_2$ represent —H, —$CONX_8X_9$, —$NO_2$, $X_8$ and $X_9$ representing H or a group $(C_1-C_6)$alkyl, $X_7$ represents —$SO_3^-M^+$ or H or alternatively a quaternary ammonium group and a denotes an integer ranging from 0 to 4 and b denotes an integer ranging from 0 to 2000; or chosen from succinimidyl-4-(N-maleimidomethyl)cyclohexane-1-carboxylate; sulfosuccinimidyl 4-(N-maleimidomethyl)cyclohexane-1-carboxylate;

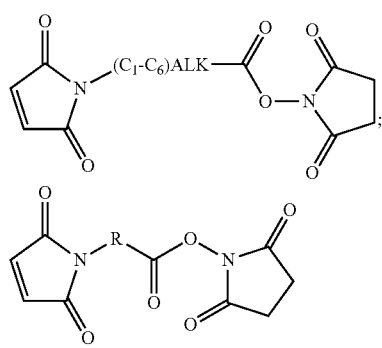

in which R represents a group —$(CH_2)_n$—, —$(CH_2)_n$-cyclohexyl-, -cyclohexyl-$(CH_2)_n$— and n represents an integer ranging from 1 to 10;

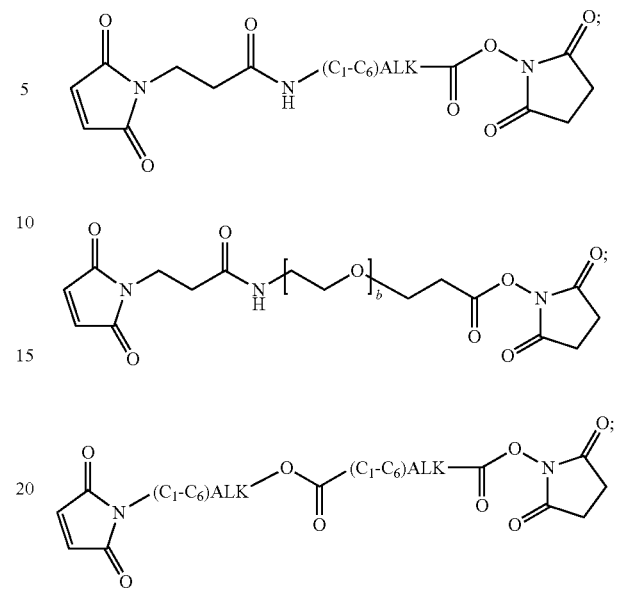

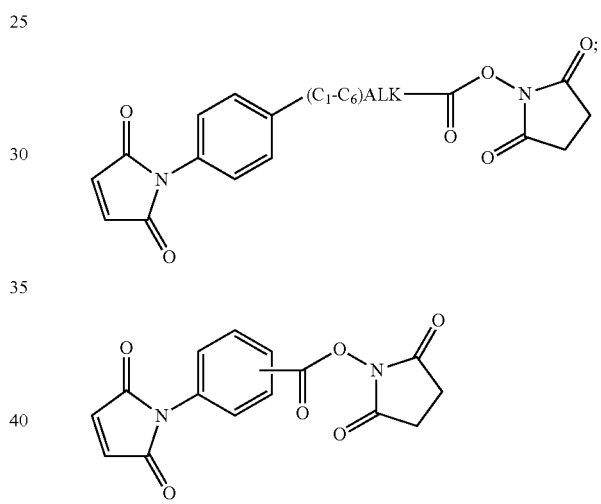

b being an integer between 0 and 2000;

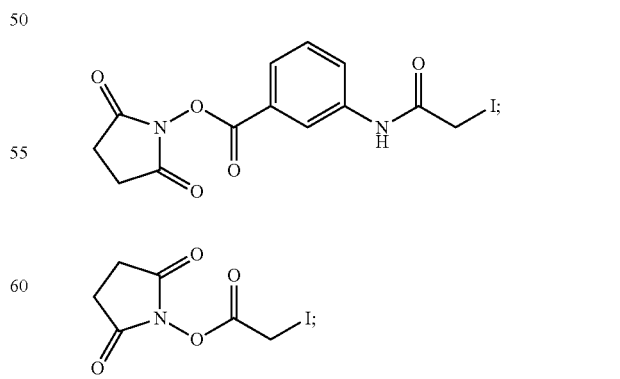

lp;1psuccinimidyl-N-bromoacetate; succinimidyl-3-(N-bromoacetamido)propionate;

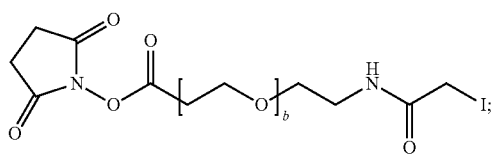

b being an integer between 0 and 2000.

when the reactive chemical group RCG1 is of the type —$SZ_a$ with $Z_a \neq H$, and when the binding agent bears amino functions, especially ε-amino groups borne by the side chains of the lysine residues of an antibody, the latter is modified by means of a modifying agent of formula

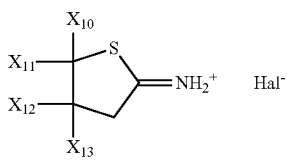

described previously.

when the reactive chemical group RCG1 is of the type —SH, and when the binding agent contains thiol functions, especially following the introduction of cysteines by mutation or by chemical modification of a binding agent containing amino functions, the binding agent is modified such that its thiol functions are converted into disulfide functions. It is possible, for example, to use a modifying agent chosen from a compound of formula

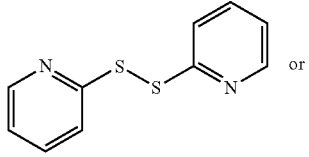 or

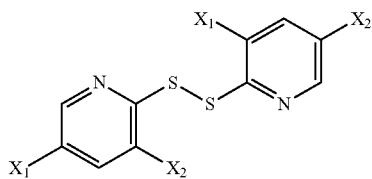

in which $X_1$ and $X_2$ represent —H, —$CONX_8X_9$ or —$NO_2$, $X_8$ and $X_9$ representing H or a group ($C_1$-$C_6$)alkyl.

Table II below illustrates the modification of an amino group of a binding agent according to the preceding methods. For the sake of simplicity, the following abbreviations are used:

Tom1 = 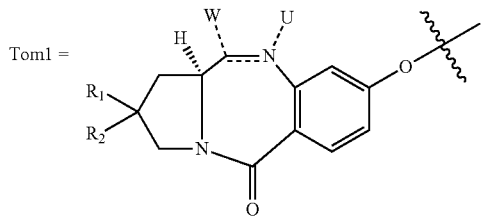

Tom'1 = 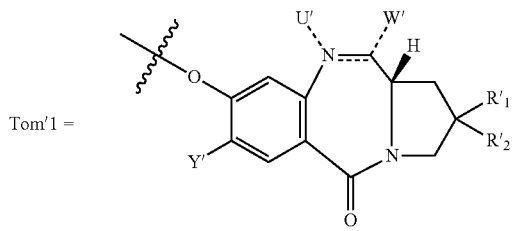

TABLE II examples of modifications of binding agents when RCG1 = —SZ$_a$

| Modifying agent | Example after reaction on an amino group, especially lysine, of an antibody, noted MAb | Conjugate |
|---|---|---|

TABLE II-continued examples of modifications of binding agents when RCG1 = —SZ_a Example after reaction on an amino group, especially lysine, of an antibody, noted MAb

| Modifying agent | Conjugate |
|---|---|
| SMCC = | |
| sulfo-SMCC = | |
| SNPP = | |

TABLE II-continued examples of modifications of binding agents when RCG1 = —SZ$_a$ TABLE II-continued examples of modifications of binding agents when RCG1 = —SZ$_a$

| Modifying agent | Example after reaction on an amino group, especially lysine, of an antibody, noted MAb | Conjugate | g: number of functions RCG2 on a modified binding agent;
d: number of pyrrolo[1,4]benzodiazepine dimers on the binding agent Mab
L* represents —L$_1$—N(Q—CH$_2$CH$_2$O)$_k$—CH$_2$CH$_2$—G)—L$_2$—

The compounds according to the invention may thus be used for the preparation of a binding agent to which is covalently attached in the para position of M the dimer of formula:

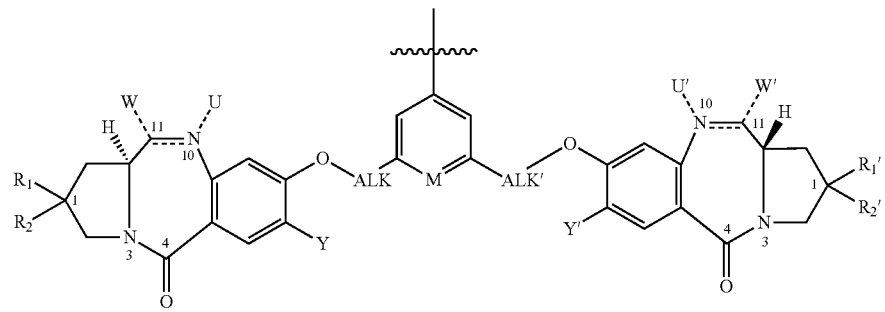

More particularly, the binding agent is an antibody. More particularly, the dimer has the formula:

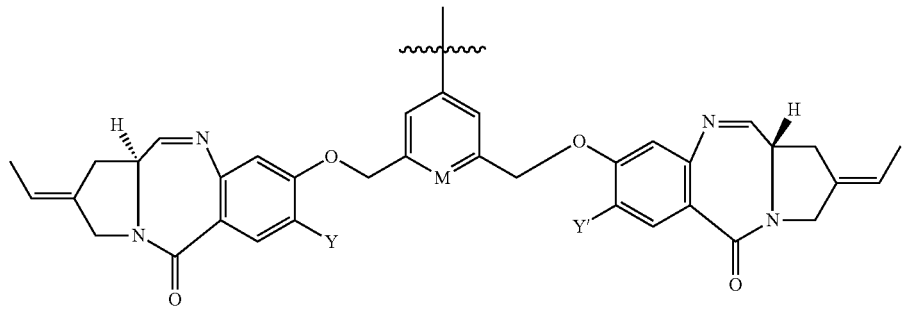

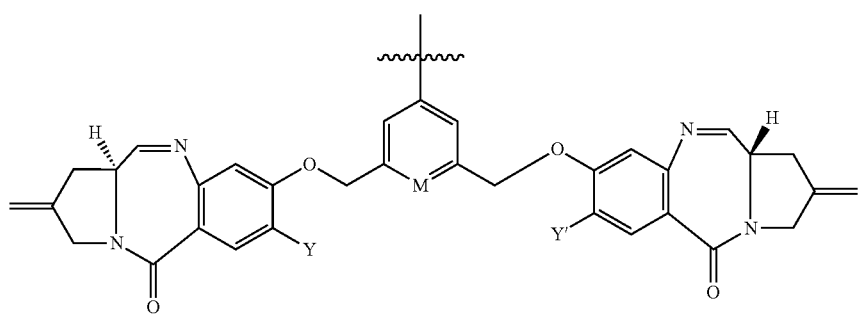

Process for Preparing the Compounds of Formula (I)

The compounds of formula (I) may be prepared according to Scheme 1:

Scheme 1

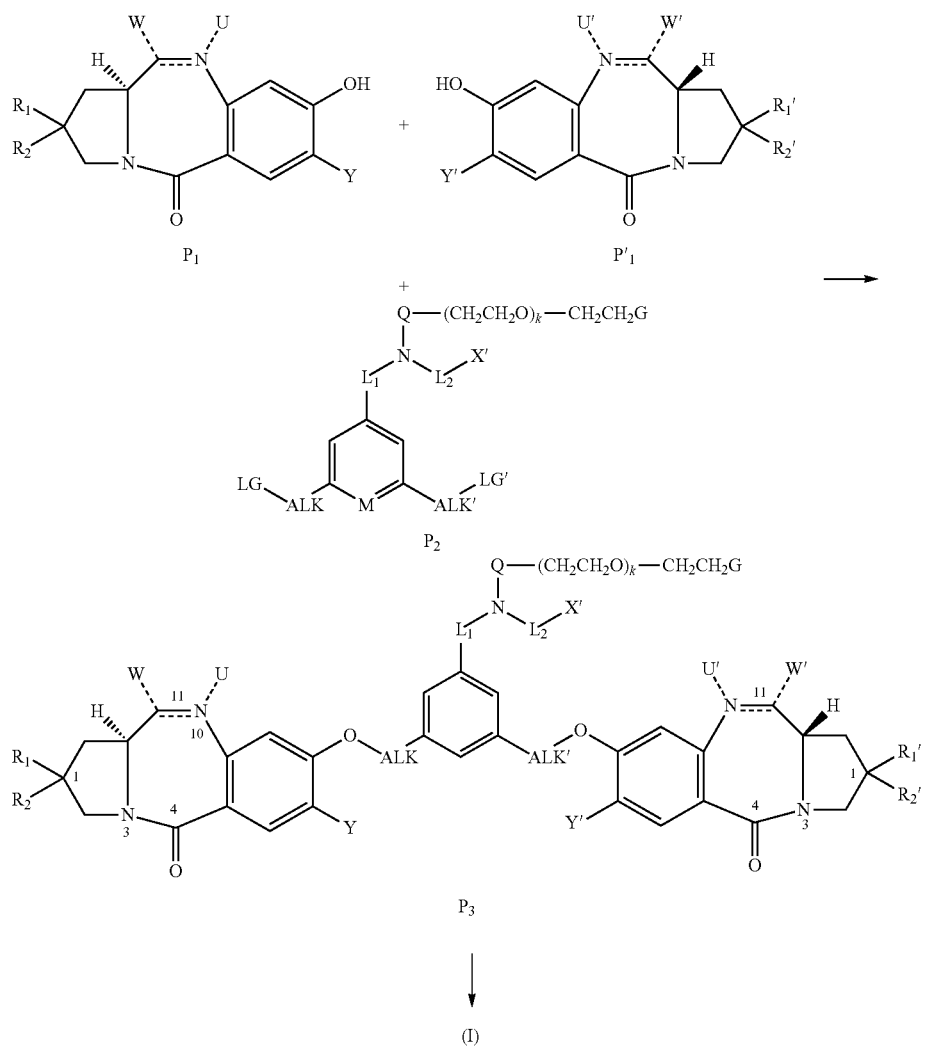

Compounds $P_1$, $P'_1$ and $P_2$ are reacted together to give $P_3$. LG and LG' denote a leaving group. The term "leaving group" denotes an atom or a group of atoms which, in the heterolytic reaction between $P_2$ and $P_1$ or $P'_1$, leaves taking the lone pair of electrons of the covalent bond connecting ALK and LG or LG'. The leaving group is more particularly chosen from a halogen atom, especially chlorine or bromine, a mesylate, tosylate or nosylate group or —OPPh$_3^+$. The intermediate compounds $P_2$ also form part of the invention.

In the preparation of a compound of formula (I) comprising the group RCG1, X' may represent the said group RCG1, in which case $P_3$ represents a compound of formula (I). X' may also be a precursor of the said group RCG1 of the type —SZ$_a$ or alternatively —C(=O)Z$_b$R$_b$ and in this case, it is necessary to convert X' into RCG1 by means of one or more chemical reactions. According to one variant, the conversion X'→RCG1 may also be performed on $P_2$.

Thus, for the preparation of a compound $P_3$ (or according to variant $P_2$) for which $Z_a$=H, it is preferred to introduce a group X'=—SZ$_a$ for which $Z_a$=—S(C$_1$-C$_6$)alkyl using the precursor of the corresponding linker, and then to reduce the disulfide function —SS(C$_1$-C$_6$)alkyl to a thiol function —SH. To do this, use may be made, for example, of tris(2-carboxy-ethyl)phosphine: see in this respect Burns J. A. et al., *J. Org. Chem.* 1991, 56(8), 2648-2650. This conversion —SS(C$_1$-C$_6$)alkyl→—SH may apply especially to compounds 1 to 19 of Table I.

In the case of preparation of a compound of formula (I) from $P_3$ according to the conversion X'→RCG1 such that RCG1 represents the group —SH, a compound $P_3$ may also be formed, such that X' may also represent the group —SZ$_a$ with $Z_a =$ 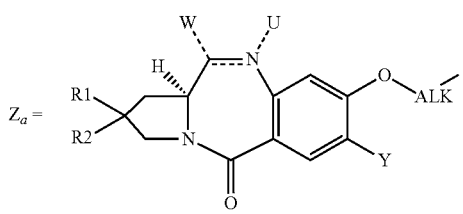

corresponding to the adduct of a thiol function to the imine function.

Similarly, for the production of a compound of formula (I) comprising a group RCG1=—C(=O)$Z_bR_b$, it is possible to convert a group X'=—C(=O)$Z_bR_b$ into a group RCG1=—C(=O)$Z_bR_b$ by means of one or more chemical reactions. In particular, in the case where

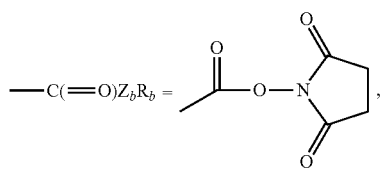

it is possible to introduce onto a compound $P_3$ (or according to variant $P_2$) the group X'=—C(=O)O—($C_1$-$C_4$)alkyl or —C(=O)O-allyl, which is then converted into a group —C(=O)OH, which finally reacts with N—N'-disuccinimidyl carbonate or NHS. The conversion —COOalkyl/allyl to —COOH may be performed by treatment with a base such as LiOH or a palladium catalyst, for example tetrakis(triphenylphosphine)palladium in the presence of an amine "scavenger", for example morpholine. The reaction with N,N'-disuccinimidyl is performed in the presence of a base, for example DIPEA; the reaction with NHS is performed in the presence of a coupling agent, for example DCC. Similarly, in the case where

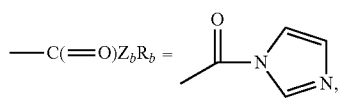

it is possible to introduce a group —C(=O)$Z_bR_b$=—COOH, which then reacts with N,N'-carbonyldiimidazole (*JACS* 1958, 80, 4423; *JACS* 1960, 82, 4596). This conversion X'=—C(=O)$Z_bR_b$→RCG1=—C(=O)$Z_bR_b$ may especially apply to the compounds of Examples 20 to 36 of Table I.

Compounds $P_1$ and $P'_1$ are described in patent applications WO 00/12508, WO 00/12507, WO 2005/040170, WO 20051085260, WO 07085930 or WO 2009/016516 or are accessible via total synthesis (Mori M. et al., *Tetrahedron*, 1986, 42, 3793-3806). In the case where P and/or $P'_1$ represent(s) tomaymycin of formula:

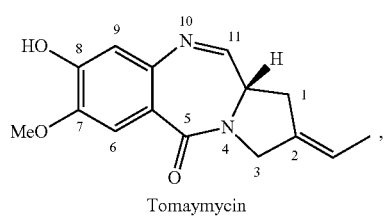
Tomaymycin the latter may be prepared with the aid of the strain *Streptomyces croceus* by following the teaching of FR 1516743 or alternatively by total synthesis (see *J. Antibiotics* 1983, XXXVI(3), 276-282 Z. Tozuka "Studies on tomaymycin. Total syntheses of the antitumor antibiotics E- and Z-tomaymycins"). Commercial compounds $P_1/P'_1$ also exist. For the introduction of the groups W/W', the imine function (═══ =double bond) is capable of adding various compounds HW/HW' (for example $H_2O$, alcohol ROH).

Case where Q=Single Bond

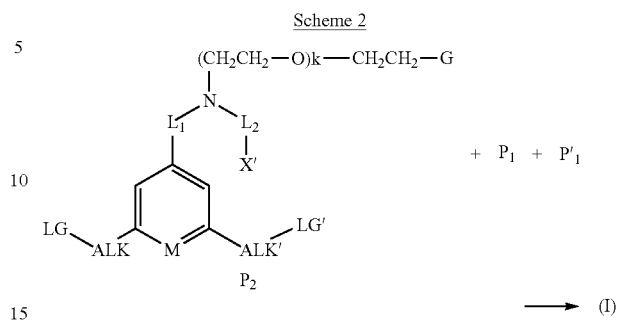

Scheme 2

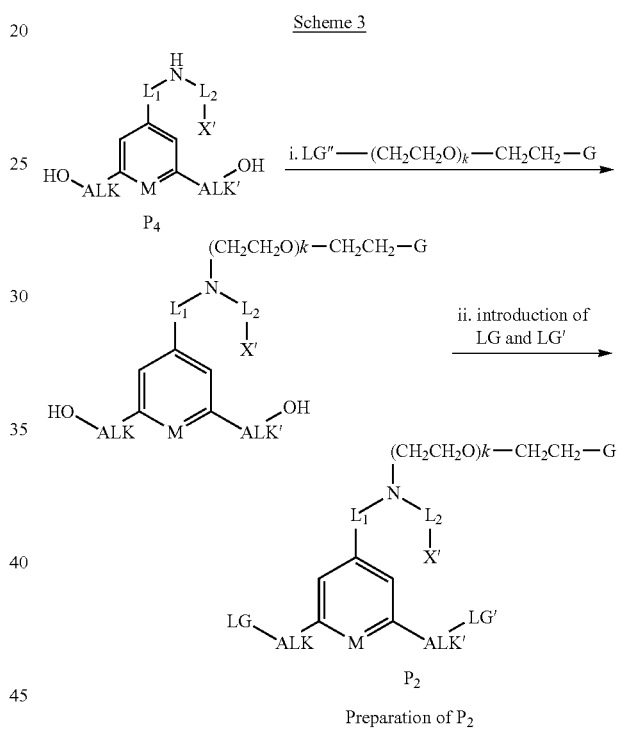

Scheme 3

Preparation of $P_2$ i. nucleophilic reaction between the secondary amine function —NH— of $P_4$ and a reagent of formula LG"-($CH_2CH_2O$)$_k$—$CH_2CH_2$-G (LG"=leaving group) in the presence of a base, for instance $K_2CO_3$ in a polar solvent such as DMF or THF.

The reagent LG"-($CH_2CH_2O$)$_k$—$CH_2CH_2$-G is obtained from a compound of formula HO—($CH_2CH_2O$)$_k$—$CH_2CH_2$-G by replacing the group —OH with the leaving group LG" by means of chemical reactions known to those skilled in the art. For example, in the case where LG" represents a mesylate group, use is made of methanesulfonyl chloride in the presence of a base such as a tertiary amine (for example TEA). In the case where LG" represents I, the mesylate is substituted with I, for example using sodium iodide, according to D. Marquis et al. *J. Org. Chem.* 1995, 24, 7984-96.

The PEG-alcohols of formula HO($CH_2CH_2O$)$_k$—$CH_2CH_2OCH_3$ are commercially available (see for example the catalogue of the American company QuantaBioDesign, Ltd.). Other PEG-alcohols HO(CH$_2$CH$_2$O)$_k$—CH$_2$CH$_2$OR with R≠Me are commercially available or alternatively are available from HO(CH$_2$CH$_2$O)$_k$—CH$_2$CH$_2$OH by means of chemical reactions known to those skilled in the art. Similarly, certain compounds for which G=NRR' and k>=1 are commercially available, for example:

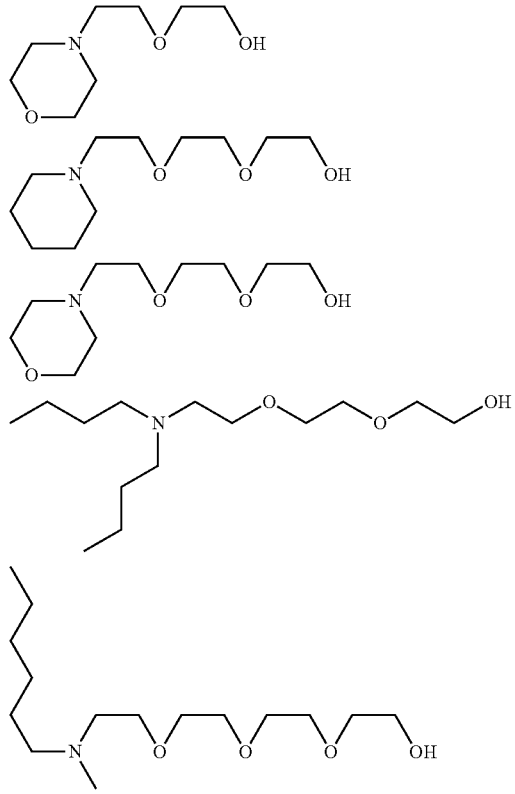

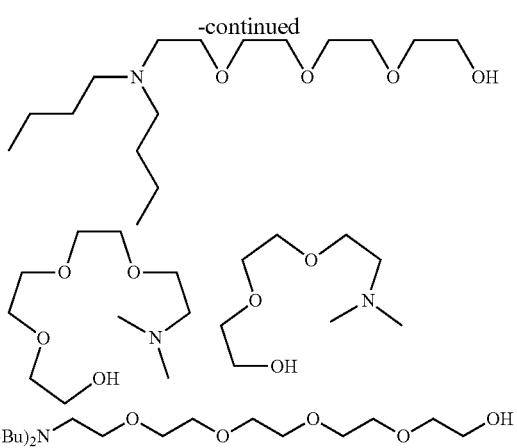

ii. introduction of LG and LG'. In the case of a mesylate group, use is made of MSC in the presence of a base such as a tertiary amine (for example TEA).
Case where Q=—C(═O)

Scheme 4

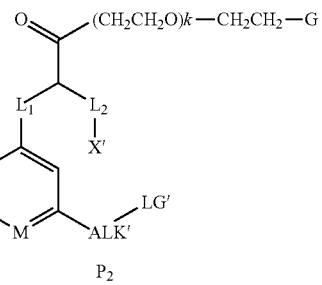

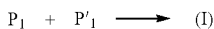

Scheme 5

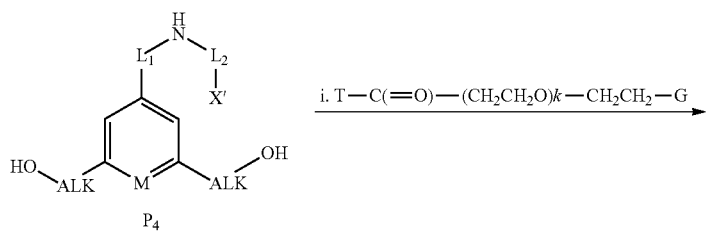

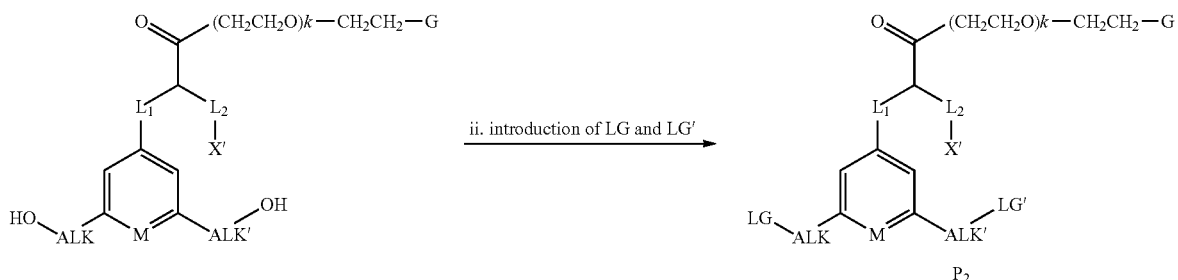

Preparation of P$_2$ i. Amidation reaction between P₄ and a carboxylic acid derivative of formula T-C(=O)—(CH₂CH₂O)ₖ—CH₂CH₂-G.

The carboxylic acid derivative may be an acyl halide (T=-Hal). According to one variant, use is made of an activated ester (for example T=—ONHS) or alternatively the carboxylic acid (T=—OH) in the presence of a coupling agent. The PEG-acids of formula HOC(=O)—(CH₂CH₂O)ₖ—CH₂CH₂OR may be prepared from the corresponding PEG-alcohols of formula HO—(CH₂CH₂O)ₖ₋₁—CH₂CH₂OR, which are commercially available for k=1 to 11, by addition to sodium acrylate, according to J. Huskens, J. A. Peters, H. van Bekkum, *Tetrahedron* 1993, 15, 3149-64. This is likewise the case when G is the group NRR' for k>=1 starting with the corresponding compounds of formula H—(OCH₂CH₂)ₖ₋₁—CH₂CH₂NRR'. Similarly, the compounds HOC(=O)—(CH₂CH₂)—NRR' (k=0) are commercially available.

ii. introduction of LG and LG'. In the case of a mesylate group, use is made of MSC in the presence of a base such as a tertiary amine (for example TEA).

Preparation of P₄
Case where X'=—C(=O)—Z_bR_b

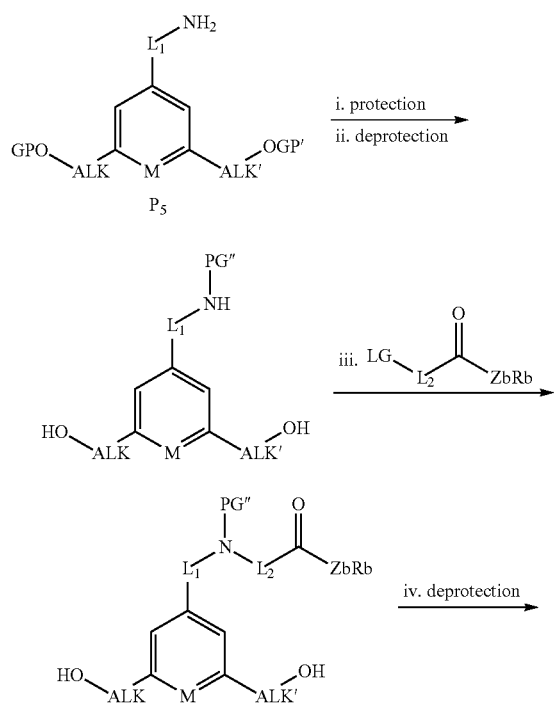

i. introduction of the protecting group PG". In the case of a nosylate group, use is made of 2-nitrobenzenesulfonyl chloride in the presence of a base such as a tertiary amine (for example TEA) or pyridine;

ii. deprotection of the groups PG and PG'. For example in the presence of hydrochloric acid or TFA when the groups PG and PG' are TBDMS.

According to one variant, in the case where ALK=ALK'=—CH₂—, P₅ may represent

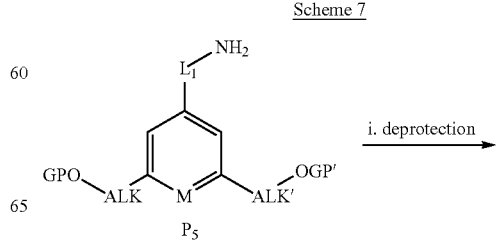

The deprotection step is then replaced with a step of reduction of the ester function to a —CH₂OH, for example with sodium borohydride; to do this, the reduction conditions given on pages 62-63 of WO 20071085930 may be applied. As described later, this variant consisting in using a diester and in then applying a reduction may be generalized to the other P₅. Furthermore, the reduction of the ester functions may be performed on a P₄ but optionally also, according to one variant, on a P₅.

iii. Nucleophilic reaction between the protected amine function —NH(PG") and a reagent of formula LG-L₂-C(=O)—Z_bR_b in the presence of a base, for instance K₂CO₃ in a polar solvent such as DMF or THF.

For the case where L₂=(C₁-C₆)ALK, the bromo-alkyl esters of formula Br—(C₁-C₆)ALK-C(=O)—OMe are commercially available. For the case where L₂=—(CH₂CH₂O)ⱼ—CH₂CH₂—, LG may be introduced starting with the corresponding PEG-alcohols of formula HO—(CH₂CH₂O)ⱼ—CH₂CH₂—C(=O)Z_bR_b. Such compounds are commercially available or alternatively may be obtained from the corresponding PEG-diols of formula HO—(CH₂CH₂O)ⱼ—H, which are commercially available for j=1 to 11, by addition to sodium acrylate, according to J. Huskens, J. A. Peters, H. van Bekkum, *Tetrahedron* 1993, 15, 3149-64.

iv. deprotection of the group PG". For example in the presence of thiophenol and a base such as caesium carbonate when PG" is the nosylate group.

Case where X'=—SZ_a
Case where L₂=(C₁-C₅)ALK

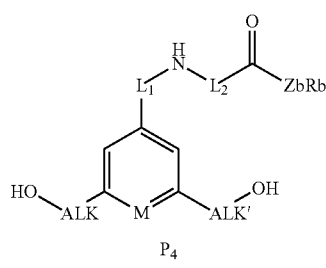

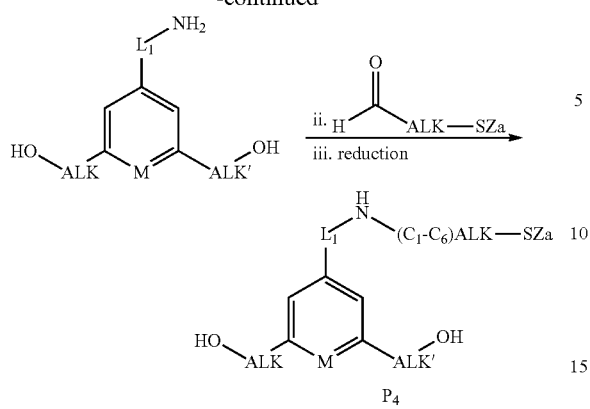

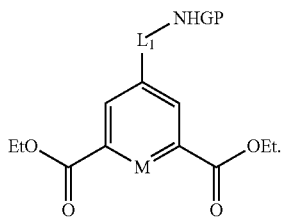

i. deprotection of the protecting groups PG and PG', preferably in acidic medium, for example in the presence of hydrochloric acid or TFA when the groups PG and PG' are TBDMS.

According to one variant, in the case where ALK=ALK'=—$CH_2$—, $P_5$ may represent The step of deprotection of the alcohol functions is then replaced with a reaction for reduction of the ester function to a function —$CH_2OH$, for example with sodium borohydride, followed by a step of deprotection of the amine function; to do this, the reduction conditions given on pages 62-63 of WO 2007/085930 may be applied.

ii. reductive amination with the aldehyde of formula HC(=O)-ALK-$SZ_a$;

iii. the intermediate amine is reduced in situ with a reducing agent, for instance sodium triacetoxyborohydride according to A. F. Abdel-Magid et al., J. Org. Chem. 1996, 61, 3849-62, preferably in acetic acid.

Case where $L_2$=—$(CH_2CH_2O)_j$—$CH_2CH_2NR''$-ALK-

Scheme 8

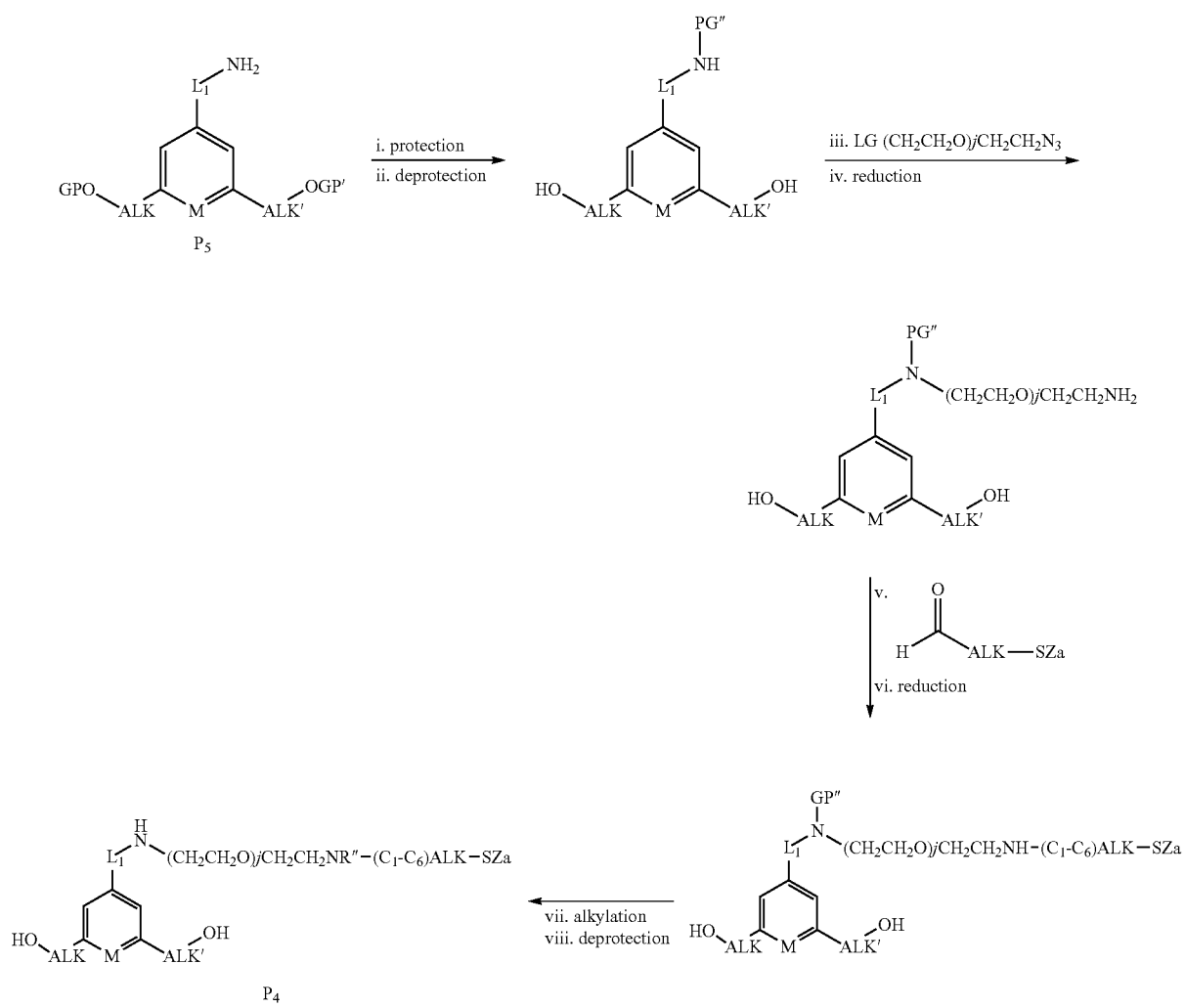

i. introduction of the protecting group PG". In the case of a nosylate group, use is made of 2-nitrobenzenesulfonyl chloride in the presence of a base such as a tertiary amine (for example TEA) or pyridine;

ii. deprotection of the groups PG and PG'. For example in the presence of hydrochloric acid or TFA when the groups PG and PG' are TBDMS.

According to one variant, in the case where ALK=ALK'=—CH$_2$—, P$_5$ may represent

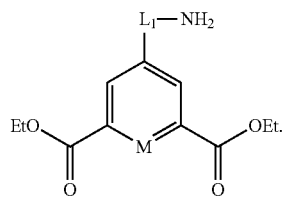

The deprotection step is then replaced with a step of reduction of the ester function to a function —CH$_2$OH, for example with sodium borohydride; to do this, the reduction conditions given on pages 62-63 of WO 2007/085930 may be applied.

iii. nucleophilic reaction between the protected amine function —NH(PG") and a reagent of formula LG-(CH$_2$CH$_2$O)$_j$CH$_2$CH$_2$N$_3$ in the presence of a base, for instance K$_2$CO$_3$ in a polar solvent such as DMF or THF. Such compounds may be obtained according to WO 07/085930, starting with the corresponding PEG-diols of formula HO—(CH$_2$CH$_2$O)$_{j+i}$—H, which are commercially available for j=0 to 10.

iv. reduction of the azido group, for example via the Staudinger reaction in the presence of triphenylphosphine and water.

v. reductive amination with the aldehyde of formula HC(=O)-ALK-SZ$_a$;

vi. the intermediate amine is reduced in situ with a reducing agent, for instance sodium triacetoxyborohydride, according to A. F. Abdel-Magid et al., J. Org. Chem. 1996, 61, 3849-62, preferably in acetic acid.

vii. alkylation of the secondary amine function.

viii. deprotection of the group PG". For example in the presence of thiophenol and a base such as caesium carbonate when PG" is the nosylate group.

Preparation of P$_5$

Case where L$_1$=-D-(C$_1$-C$_6$)ALK-, D=O or NH

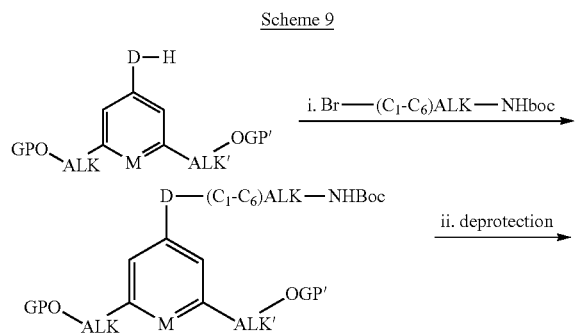

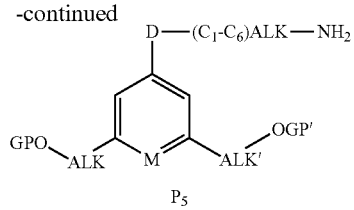

i. nucleophilic reaction between the function -DH and a boc-protected bromo-amine of formula Br(C$_1$-C$_6$)ALK-NHboc in the presence of a base, for instance K$_2$CO$_3$ in a polar solvent such as DMF or THF (see for example the conditions on page 63 of WO 07085930).

ii. selective deprotection of the amine, preferably in acidic medium, for example in the presence of hydrochloric acid or TFA. For the cases where a selective deprotection cannot be performed, for example when the groups PG and PG' are TBDMS, a step of selective reprotection of the alcohols is necessary.

According to one variant, in the case where ALK=ALK'=—CH$_2$—, it is possible to perform the nucleophilic substitution of the bromo-amine with a diester of formula:

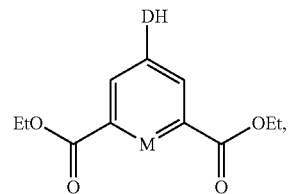

so as to obtain a compound P$_5$ of formula

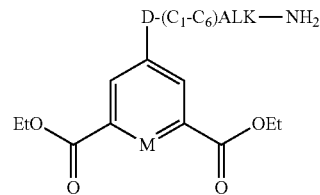

which is used in the form as obtained, for the preparation of P$_4$.

Case where L$_1$=—N((C$_1$-C$_4$)Alkyl)-(C$_1$-C$_6$)ALK-

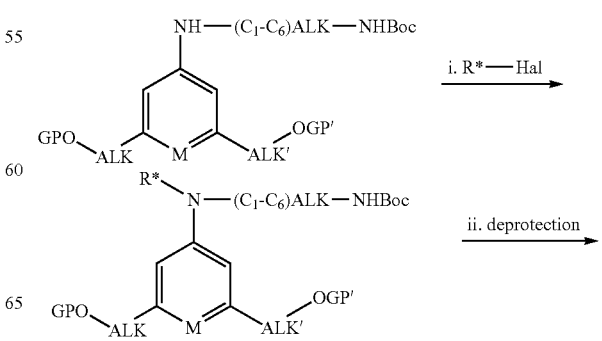

-continued

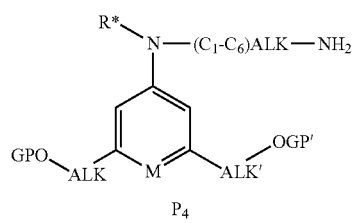

P$_4$ i. nucleophilic reaction between the function —NH— and an alkyl halide of formula R*-Hal with R*=(C$_1$-C$_4$)alkyl in the presence of a base, for instance K$_2$CO$_3$ in a polar solvent such as DMF or THF.

According to one variant, in the case where ALK=ALK'=—CH$_2$—, it is possible to perform the nucleophilic substitution of the alkyl halide with a diester of formula:

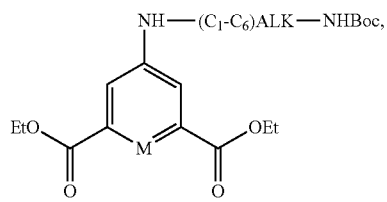

so as to obtain a compound P$_5$ of formula

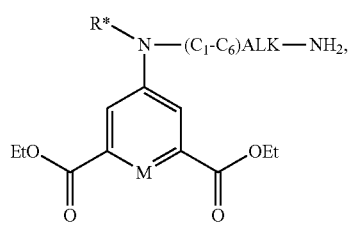

which is used in the form as obtained, for the preparation of P$_4$.

Case where L$_1$=—(OCH$_2$CH$_2$)$_i$ i. nucleophilic reaction between one of the —OH functions (the two others being protected with PG which denotes a protecting group) and an azido-PEG reagent of formula LG-(CH$_2$CH$_2$)—(OCH$_2$CH$_2$)$_{i-1}$—N$_3$ bearing a nucleofugal group (LG) such as Hal or mesylate, in the presence of a base, for instance K$_2$CO$_3$ in a polar solvent such as DMF or THF (see for example the conditions on page 63 of WO 07085930).

ii. reduction of the azido group, for example with triphenylphosphine in the presence of water in a polar solvent such as THF.

According to one variant, in the case where ALK=ALK'=—CH$_2$—, it is possible to perform the nucleophilic substitution of the azido-PEG reagent with the hydroxy-diester of formula:

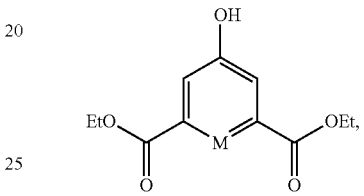

so as to obtain a compound P$_5$ of formula

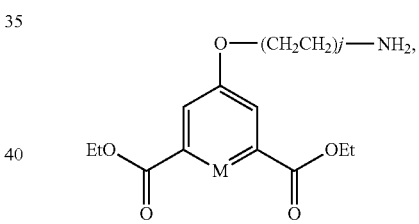

which is used in the form as obtained, for the preparation of P$_4$.

Scheme 10

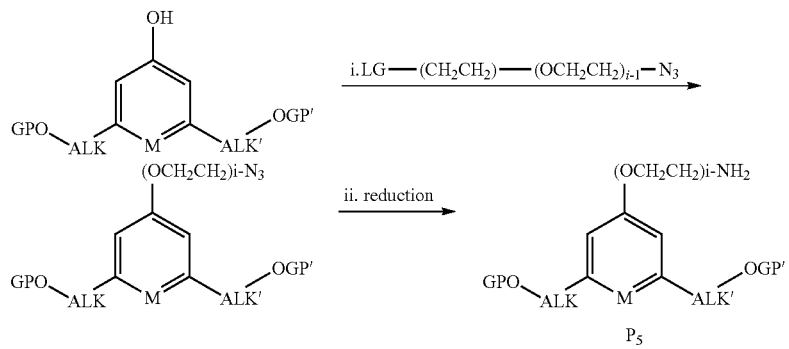

Case where $L_1$=Single Bond

Scheme 11

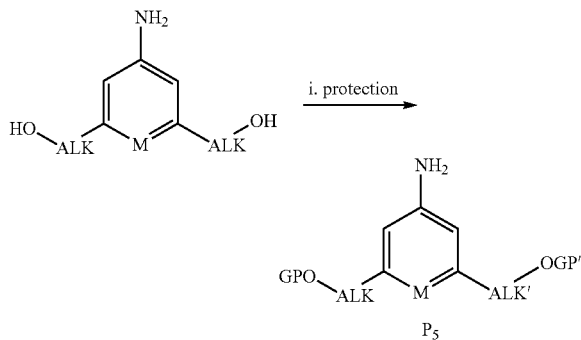

i. protection of the alcohol groups
$P_5$ may be obtained from the halo-diol of formula

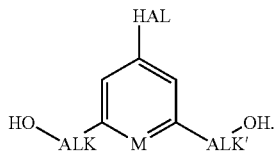

An example of a halo-diol and of the corresponding protected diol is described in Scheme 1 on page 48 of WO 2009/016516 (compounds 2 and 3 of Scheme 1). Two examples of protected diols are those of CAS Nos. 181225-40-1 and 181225-41-2. The halo-diol may be obtained by reduction of the corresponding diacid or diester compound, for example that of CAS No. 193010-40-1. See also in the case of a pyridine (M=N): *Liebigs Annalen der Chemie* 1991, 10, 987-988 or *Tetrahedron* 2005, 61(7), 1755-1763 (compound 3 of Scheme 1).

A person skilled in the art may be inspired by the operating conditions of the examples described below which are given for particular linkers $L_1$ and $L_2$ and may adapt them to other linkers $L_1$ and $L_2$.

Process for Preparing the Conjugate

The conjugate is obtained via the process that consists in:
(i) placing in contact and leaving to react an aqueous solution, optionally buffered, of the binding agent, optionally modified with a modifying agent, and a solution of a compound of formula (I);
(ii) and then in optionally separating the conjugates formed in step (i) from the compound of formula (I) and/or the unreacted binding agent and/or any aggregates that may have formed.

The chemical group RCG1 of the compound of formula (I) must be reactive towards the chemical groups RCG2 present on the binding agent, especially towards the amino groups present on antibodies, the said chemical groups RCG2 having been introduced, where appropriate, by the modifying agent, so as to attach the compound of formula (I) to the binding agent via formation of a covalent bond.

According to one variant, in step (ii) the conjugate formed in step (i) is separated from the unreacted binding agent and from any aggregates that may be present in the solution. According to another variant, in step (ii) the conjugate from step (i) is separated only from the unreacted compound of formula (I) and from the aggregates that may have formed, and any unreacted binding agent is left in solution.

The aqueous solution of the binding agent may be buffered with at least one buffer, for instance potassium phosphate or N-2-hydroxyethylpiperazine-N'-2-ethanesulfonic acid (HEPES buffer). The buffer depends on the nature of the binding agent. The compound of formula (I) is dissolved in a polar organic solvent, for example DMSO or DMA.

The reaction takes place at a temperature generally of between 20 and 40° C. The reaction time may range between 1 and 24 hours. The reaction between the binding agent and the compound of formula (I) may be monitored by SEC with a refractometric and/or ultraviolet detector, so as to determine its progress. If the degree of grafting is insufficient, the reaction may be left for longer and/or compound of formula (I) may be added. Reference may be made to the general method given in the examples section for further details regarding the particular conditions that may be used for the conjugation.

A person skilled in the art has at his disposal various chromatographic techniques for the separation of step (ii): the conjugate may be purified, for example, by steric exclusion chromatography (SEC), by adsorption chromatography (such as ion exchange, IEC), by hydrophobic interaction chromatography (HIC), by affinity chromatography, by chromatography on mixed supports such as ceramic hydroxyapatite, or by HPLC. Purification by dialysis or diafiltration may also be used.

The term "aggregates" means associations that may form between two or more binding agents, the binding agents having possibly been modified by conjugation. Aggregates are capable of being formed under the influence of a large number of parameters such as a high concentration of binding agent in the solution, the pH of the solution, high shear forces, the number of grafted dimers and their hydrophobic nature, the temperature (see the references cited in the introduction of *J. Membrane Sci.* 2008, 318, 311-316), the influence of some of them occasionally not being explained with precision. In the case of proteins or antibodies, reference may be made to *AAPS Journal*, "Protein Aggregation and Bioprocessing" 2006, 8(3), E572-E579. The content of aggregates may be determined by means of known techniques such as SEC (see in this respect *Analytical Biochemistry* 1993, 212(2), 469-480).

After step (i) or (ii), the solution of the conjugate may undergo a step (iii) of ultrafiltration and/or diafiltration. The conjugate in aqueous solution is thus obtained after these steps.

Antibody

The antibody (see in this respect Janeway et al. "Immunobiology", 5th edition, 2001, Garland Publishing, New York) may be chosen from those described especially in patent applications WO 04043344, WO 08010101, WO 08047242, WO 05009369 (anti-CA6). The antibody may especially be monoclonal, polyclonal or multispecific. It may also be an antibody fragment. It may also be a murine, human, humanized or chimeric antibody.

Conjugate

A conjugate generally comprises from about 1 to 10 pyrrolo[1,4]benzodiazepine dimers attached to the binding agent (this is the degree of grafting or the "drug-to-antibody ratio" (or "DAR")). This number varies as a function of the nature of the binding agent and of the dimer, and also of the operating conditions used for the conjugation (for example the number of equivalents of dimer relative to the binding agent, the reaction time, the nature of the solvent and of any cosolvent). Placing the binding agent and the dimer in contact leads to a mixture comprising: several conjugates that are individually distinguished from each other by different DARs; possibly the unreacted binding agent (in the case of an incomplete reaction); possibly aggregates. The DAR, which is determined on the final solution, for example by UV spectroscopy, thus corresponds to an average DAR.

In the case where the binding agent is an antibody, UV spectroscopy may be a method used for determining the DAR. This method is inspired by that presented in Antony S. Dimitrov (ed), LLC, 2009, "Therapeutic Antibodies and Protocols", vol. 525, 445, Springer Science. It consists in measuring the absorbance of a solution of conjugate after the separation step (ii) at two wavelengths noted WL1 and WL2. The following molar extinction coefficients of the naked antibody and of the pyrrolo[1,4]benzodiazepine dimer prior to conjugation are used.

The absorbances of the solution of conjugate at WL1 and WL2 ($A_{WL1}$) and ($A_{WL2}$) are measured either on the corresponding peak of the SEC spectrum (which makes it possible to calculate a "DAR(SEC)") or by using a standard UV spectrophotometer (which makes it possible to calculate a "DAR (UV)"). The absorbances may be expressed in the form:

$$A_{WL1}=(c_D \times e_{DWL1})+(c_A \times e_{AWL1})$$

$$A_{WL2}=(c_D \times e_{DWL2})+(c_A \times e_{AWL2})$$

for which equations:
- $c_D$ and $c_A$ denote, respectively, the concentrations in the solution of the part of the conjugate relating to the pyrrolo[1,4]benzodiazepine dimer and the part of the conjugate relating to the antibody;
- $e_{DWL1}$ and $e_{DWL2}$ denote, respectively, the molar extinction coefficients of the pyrrolo[1,4]benzodiazepine dimer before conjugation at the wavelengths WL1 and WL2;
- $e_{AWL1}$ and $e_{AWL2}$ denote, respectively, the molar extinction coefficients of the naked antibody at the two wavelengths WL1 and WL2.

The term "naked antibody" means the antibody to which no pyrrolo[1,4]benzodiazepine dimer is attached, i.e. the antibody before the conjugation step.

Resolution of these two equations leads to:

$$c_D=[(e_{AWL1} \times A_{WL2})-(e_{AWL2} \times A_{WL1})]/[(e_{DWL2} \times e_{AWL1})-(e_{AWL2} \times e_{DWL1})]$$

$$c_A=[A_{WL1}-(c_D \times e_{DWL1})]/e_{AWL1}$$

The average DAR then corresponds to $C_D/C_A$. In the case of the pyrrolo[1,4]benzodiazepine dimers, the two wavelengths considered are: WL1=280 nm and WL2=320 nm. The average DAR is preferably between 1 and 10, and preferably between 1.5 and 7.

The conjugate may be used as an anticancer agent. By virtue of the presence of the binding agent, the conjugate is made very selective towards tumour cells rather than healthy cells. This makes it possible to direct the compound of formula (I) which has anticancer activity into an environment close to these tumour cells or directly therein (see in this respect the following publications that describe the use of monoclonal antibody conjugates in cancer treatment: "Antibody-drug conjugates for cancer therapy" Carter P. J. et al., Cancer J. 2008, 14, 154-169; "Targeted cancer therapy: conferring specificity to cytotoxic drugs" Chari R., Acc. Chem. Res. 2008, 41, 98-107). It is possible to treat solid or liquid cancers.

The conjugate is formulated in the form of a buffered aqueous solution at a concentration generally of between 1 and 10 mg/ml. This solution may be injected in perfusion form as such, or may be rediluted to form a perfusion solution.

EXAMPLES

Method A

High-Pressure Liquid Chromatography—Mass Spectrometry (LMSC)

The spectra were acquired on a Waters UPLC-SQD machine in positive and/or negative electrospray ionization mode (ES+/−). Chromatographic conditions: column: ACQUITY BEH C18—1.7 µm—2.1×50 mm; solvents: A: $H_2O$ (0.1% formic acid) B: $CH_3CN$ (0.1% formic acid); column temperature: 50° C.; flow rate: 1 ml/min; gradient (2 min): from 5 to 50% B in 0.8 min; 1.2 min: 100% B; 1.85 min: 100% B; 1.95: 5% B.

Method B

High-Pressure Liquid Chromatography—Mass Spectrometry (LMSC)

The spectra were acquired on a Waters ZQ machine in positive and/or negative electrospray mode (ES+/−) with a U.V. DAD 200<WL<400 nm detector. Chromatographic conditions: column: Phenomenex Kinetex C18 100A 3×50 mm, particle diameter 2.6 µm; solvents: A: $H_2O$ (0.1% formic acid) B: $CH_3CN$; column temperature: 50° C.; flow rate: 1 ml/min; gradient (6 min): 6% B for 0.80 min; from 6 to 100% B in 3.9 min; 4.80 min: 100% B; 5 min: 6% B; 6 min: 6% B.

Method C

High-Pressure Liquid Chromatography—Mass Spectrometry (LMSC)

The spectra were acquired on a Waters ZQ machine in positive and/or negative electrospray mode (ES+/−) with a U.V. DAD 200<WL<400 nm detector. Chromatographic conditions: column: Phenomenex Kinetex C18 3×100 mm column, particle diameter 2.6 µm; solvents: A: $H_2O$ (0.1% formic acid) B: $CH_3CN$; column temperature: 50° C.; flow rate: 0.8 ml/min; gradient (8.2 min): 4% B for 0.15 min; from 6 to 100% B in 6.85 min; 7.1 min: 100% B; 7.4 min: 4% B; 8.2 min: 4% B.

Method D

Deglycosylation and Mass Spectrometry (HRMS) of a Conjugate

Deglycosylation is an enzymatic digestion technique using glycosidase. It is performed starting with 500 µl of conjugate+100 µl of Tris HCl 50 mM buffer+10 µl of glycanase-F enzyme (100 units of lyophilized enzyme/100 µl of water). The mixture is vortexed and maintained overnight at 37° C. The deglycosylated sample is then ready to be analysed by HRMS. Depending on the case, the HRMS analysis of the sample may also be performed without prior deglycosylation. In both cases, the mass spectra were obtained on a Waters Xévo Q-Tof machine in positive electrospray mode (ES+). Chromatographic conditions: Acquity UPLC Waters BEH 300 C4 2.1×150 mm column, particle diameter 1.7 µm; solvents: A: $H_2O$+0.1% formic acid: B: $CH_3CN$+0.1% formic acid; column temperature 70° C.: flow rate 0.5 ml/min; gradient (10 min): 20% B for 2 min 50 sec; from 20 to 80% B in 2 min 5 sec; 8 min 50 sec: 80% B; 8 min 55 sec: 20% B; 10 min: 20% B.

Method E

High-Pressure Liquid Chromatography—Mass Spectrometry (LMSC)

The spectra were acquired on a Waters UPLC-SQD line in positive and/or negative electrospray ionization mode (ES+/−) with a U.V. DAD 210<WL<400 nm detector. Chromatographic conditions: column: ACQUITY UPLC BEH C18—1.7 μm—2.1×30 mm; solvents: A: $H_2O$ (0.1% formic acid) B: $CH_3CN$ (0.1% formic acid); column temperature: 45° C.; flow rate: 0.6 ml/min; gradient (2 min): from 5 to 50% B in 1 min; from 50 to 100% B in 0.3 min; 1.45 min: 100% B; from 100 to 5% B in 0.3 min; 2 min: 100% B.

Method F

High-Pressure Liquid Chromatography—Mass Spectrometry (LMSC)

The spectra were acquired on a Waters ZQ line in positive and/or negative electrospray mode (ES+/−) with a U.V. DAD 200<WL<400 nm detector. Chromatographic conditions: column: XSelect CSH Waters C18 3×75 mm, particle diameter 3.5 μm; solvents: A: $H_2O$ (0.1% formic acid) B: $CH_3CN$ (0.1% formic acid); column temperature: 50° C.; flow rate: 0.8 ml/min; gradient (6 min): 6% B for 0.80 min; from 6 to 100% B in 3.9 min; 4.80 min: 100% B; 5 min: 6% B; 6 min: 6% B.

Method G

High-Pressure Liquid Chromatography—Mass Spectrometry (LMSC)

The spectra were acquired on a Waters UPLC-SQD machine in positive and/or negative electrospray ionization mode (ES+/−). Chromatographic conditions: column: ACQUITY BEH C18—1.7 μm—2.1×50 mm; solvents: A: $H_2O$ (0.1% formic acid) B: $CH_3CN$ (0.1% formic acid); column temperature: 50° C.; flow rate: 0.8 ml/min; gradient (2.5 min): from 5 to 100% B in 1.8 min; 2.40 min: 100% B; 2.45 min: 100% B; from 100 to 5% B 0.05 min.

The antibody hu2H11 (also known as hu53 2H11 on page 15 of WO 2008010101; it is an antibody comprising a Vh having the amino acid sequence SEQ ID No. 24) or the antibody hu2H11R35R74 obtained by directed mutagenesis of hu53 2H11 (referenced on page 20 of WO 2011039721; it is an antibody comprising a Vh having the amino acid sequence SEQ ID No. 18 and a Vl having the sequence SEQ No. 16) is used.

Chapter 1

Novel Tomaymycin Derivatives

Example 1

1.1. 4-{2-[{2-[2-(2-methoxy-ethoxy)-ethoxy]-ethyl}-(2-methyl-(2-methyl-2-mercapto-propyl)-amino]-ethoxy}-2,6-bis-[(S)-2-eth-(E)-ylidene-7-dimethoxy-1,2,3,11a-tetrahydropyrrolo[2,1c][1,4]benzodiazepin-5-one-8-yloxymethyl]-pyridine

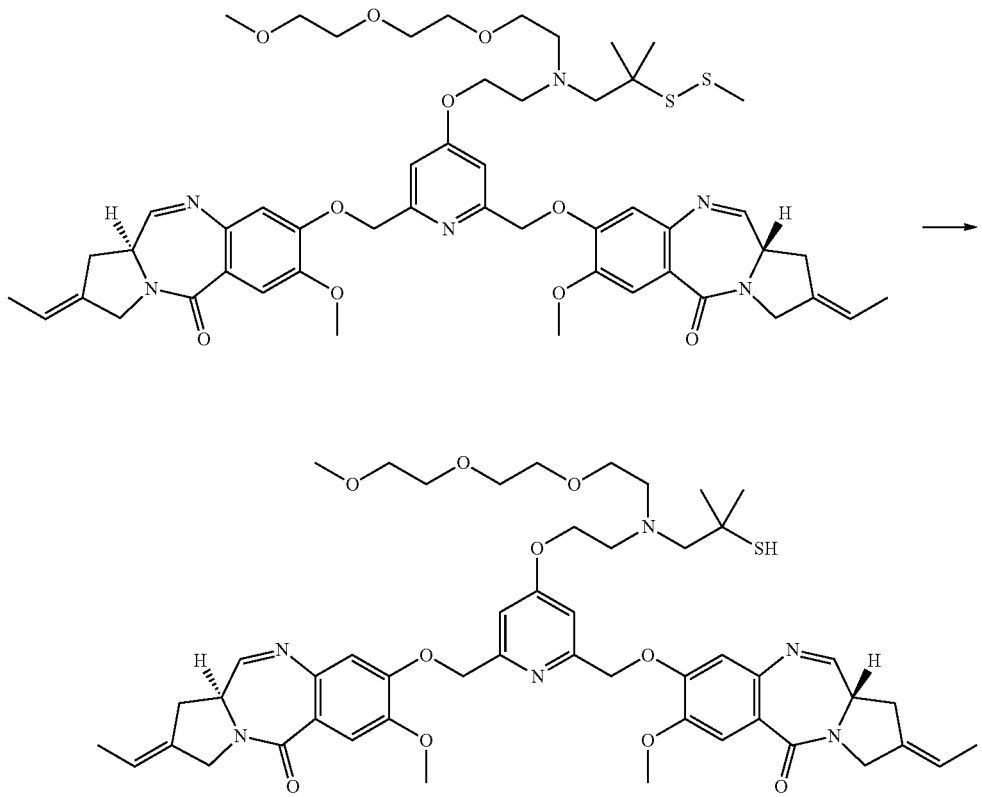

To 20 mg of 4-{2-[{2-[2-(2-methoxy-ethoxy)-ethoxy]-ethyl}-(2-methyl-2-methyldisulfanyl-propyl)-amino]-ethoxy}-2,6-bis-[(S)-2-eth-(E)-ylidene-7-dimethoxy-1,2,3,11a-tetrahydropyrrolo[2,1c][1,4]benzodiazepin-5-one-8-yloxymethyl]-pyridine dissolved in 900 μL of MeOH and 400 μL of DMF was added a solution of 17.5 mg of tris(2-carboxyethyl)phosphine hydrochloride and 15.8 mg of NaHCO₃ in 370 μL of water. The mixture obtained was stirred for 1 hour at room temperature and then concentrated under reduced pressure and purified by flash chromatography on silica (Interchrom Puriflash Silica 15/35U 2G), using a gradient of 0 to 10% MeOH in a 9:1 DCM/acetonitrile mixture. The fractions containing the desired product were combined and concentrated under reduced pressure. 7 mg of 4-{2-[methyl-(2-methyl-2-mercapto-propyl)-amino]-ethoxy}-2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridine are thus obtained: LC/MS (A): tr=1.06 min; [M+H]+: m/z 941; [M+H₂O+H]+: m/z 959.

1.2. 4-{2-[{2-[2-(2-methoxy-ethoxy)-ethoxy]-ethyl}-(2-methyl-2-methyldisulfanyl-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine mg of tomaymycin in 425 μL of DMF, along with 39.6 mg of K₂CO₃ and 15.8 mg of KI. The mixture was stirred for 12 hours at 30° C. and then hydrolysed until precipitation takes place. The insoluble matter was removed by filtration on a sinter funnel, washed with DCM and the combined organic phases were then concentrated under reduced pressure and purified by flash chromatography on silica (Analogix Super Flash SiO₂ SF25-8g) using a gradient of 0 to 10% MeOH in DCM. The fractions containing the desired product were combined and concentrated under reduced pressure, taken up in a 1/1 dioxane/water mixture and concentrated again under reduced pressure. 23 mg of 4-{2-[{2-[2-(2-methoxy-ethoxy)-ethoxy]-ethyl}-(2-methyl-2-methyldisulfanyl-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine were thus obtained. ¹H NMR (500 MHz, chloroform-d): broad signals: 1.20 to 1.78 (m, 12H); 2.40 (s, 3H); 2.70 to 3.10 (m, 10H); 3.34 (m, 4H); 3.49 to 3.70 (m, 8H); 3.71 (s, 3H); 3.91 (m, 2H); 4.00 (s, 6H); 4.27 (m, 4H); 5.27 (m, 4H); 5.60 (m, 2H); 6.86 (s, 2H); 7.00 (m, 2H); 7.56 (s, 2H); 7.65 (d, J=4.4 Hz, 2H). LC/MS (A): Tr=0.81 min; [M+H]+: m/z 987.

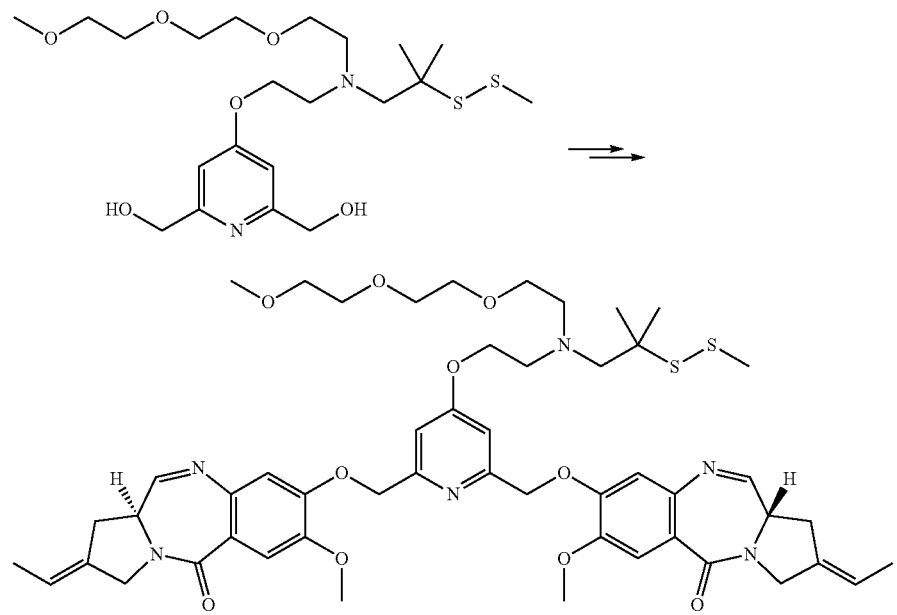

To a solution of 30 mg of 4-{2-[{2-[2-(2-methoxy-ethoxy)-ethoxy]-ethyl}-(2-methyl-2-methyldisulfanyl-propyl)-amino]-ethoxy}-2,6-bis-(hydroxy methyl)-pyridine and 65.5 μL of diisopropylethylamine in 200 μL of DCM cooled to −20° C. was added 19.4 μL of MSC. After stirring for 20 minutes, the mixture was hydrolysed and the organic phase was washed with water and then dried over MgSO₄ and concentrated under reduced pressure. The residue obtained (36 mg) dissolved in 400 μL of DMF was added to a solution of 26

1.3. 4-{2-[{2-[2-(2-methoxy-ethoxy)-ethoxy]-ethyl}-(2-methyl-2-methyldisulfanyl-propyl)-amino]-ethoxy}-2,6-bis-(hydroxy methyl)-pyridine

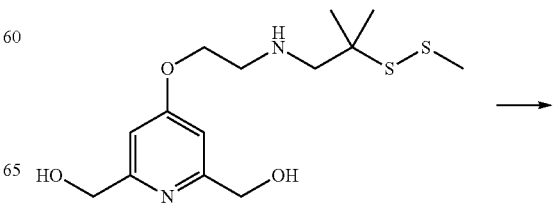

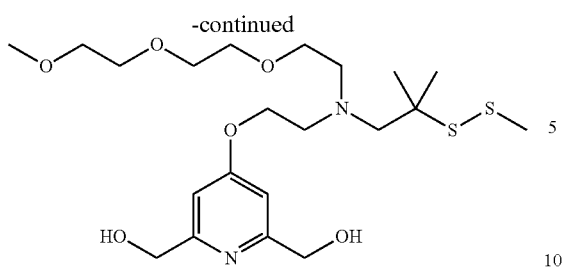

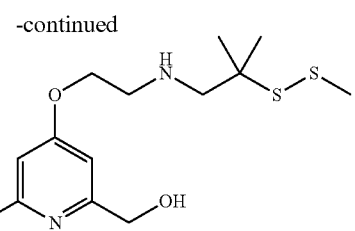

To a solution of 100 mg of 4-[2-(2-methyl-2-methyldisulfanyl-propylamino)ethoxy]-2,6-bis-(hydroxymethyl)-pyridine in 2 mL of DMF was added 99 mg of 1-iodo-2-[2-(2-methoxy-ethoxy)-ethoxy]-ethane (B. Ben Aroya Bar Nir, J. F. Kadla *Carbohydrate Polymers*, 2009, 76, 60-67) and 54 mg of K$_2$CO$_3$. After 12 hours at 60° C., the mixture was supplemented with 40 mg of 1-iodo-2-[2-(2-methoxy-ethoxy)-ethoxy]-ethane and a further 55 mg of K$_2$CO$_3$. The mixture obtained was stirred for a further 24 hours at 80° C. After concentration under reduced pressure, the crude product thus obtained was dissolved in a minimum amount of MeOH and applied on Mega BE-SCX, 1GM 6ML (Varian). After washing the phase with MeOH, the product of interest was eluted with a 2N solution of ammonia in MeOH. The MeOH phase was concentrated under reduced pressure and then reapplied on Mega BE-SCX, 2GM 12ML (Varian) according to the same protocol. The methanol/NH$_3$ phases were concentrated under reduced pressure and the residue obtained was purified by flash chromatography on silica (Merck SuperVarioFlash 10 g column, Si60 15-40 µm), using a gradient of 0 to 10% MeOH in DCM. The fractions containing the desired product were combined and concentrated under reduced pressure. 30 mg of 4-{2-[{2-[2-(2-methoxy-ethoxy)-ethoxy]-ethyl}-(2-methyl-2-methyldisulfanyl-propyl)-amino]-ethoxy}-2,6-bis-(hydroxymethyl)-pyridine were thus obtained. $^1$H NMR (400 MHz, DMSO-d$_6$): 1.27 (s, 6H); 2.40 (s, 3H); 2.75 (s, 2H); 2.80 (t, J=5.9 Hz, 2H); 3.00 (t, J=5.9 Hz, 2H); 3.23 (s, 3H); 3.40 (m, 2H); 3.47 to 3.55 (m, 8H); 4.12 (t, J=5.9 Hz, 2H); 4.45 (d, J=5.9 Hz, 4H); 5.30 (t, J=5.9 Hz, 2H); 6.85 (s, 2H). LC/MS (A): tr=0.44 min; [M+H]+: m/z 479; [M−H+HCO$_2$H]−: m/z 523.

1.4. 4-[2-(2-methyl-2-methyldisulfanyl-propylamino)-ethoxy]-2,6-bis-(hydroxymethyl)-pyridine

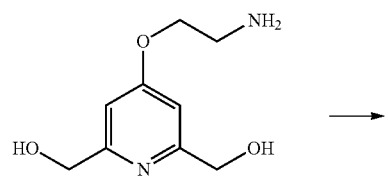

To a suspension of 390 mg of 4-[2-amino-ethoxy]-2,6-bis-(hydroxymethyl)-pyridine (prepared after deprotection of the boc group of 4-(2-tert-butoxycarbonylamino-ethoxy)-2,6-bis-(hydroxymethyl)-pyridine described on page 101 of WO 07085930) in 2 mL of THF was added 270 µl of 2-(methyldithio)-isobutyraldehyde and 730 µL of titanium isopropoxide. After 20 min, a further 270 µl of 2-(methyldithio)-isobutyraldehyde and 730 µL of titanium isopropoxide were added and the mixture was stirred for 2 hours at room temperature. The mixture was then supplemented with 6 mL of ethanol, stirred for 20 min at room temperature and then supplemented with 124 mg of sodium cyanoborohydride. After stirring for 45 minutes, a further 124 mg of sodium cyanoborohydride were added and after stirring for 1 hour, the mixture was concentrated under reduced pressure, and diluted with EtOAc and water. The resulting precipitate was filtered off, and dissolved in aqueous 1M HCl solution. The aqueous phase obtained was brought to basic pH with aqueous 5M sodium hydroxide solution, extracted 3× with DCM and the combined organic phases were concentrated under reduced pressure. 322 mg of 4-[2-(2-methyl-2-methyldisulfanyl-propylamino)-ethoxy]-2,6-bis-(hydroxymethyl)-pyridine were obtained. $^1$H NMR (400 MHz, DMSO-d$_6$): 1.26 (s, 6H); 1.81 (broad m, 1H); 2.39 (s, 3H); 2.67 (broad s, 2H); 2.94 (broad t, J=5.7 Hz, 2H); 4.11 (t, J=5.7 Hz, 2H); 4.45 (d, J=5.5 Hz, 4H); 5.32 (t, J=5.5 Hz, 2H); 6.85 (s, 2H). LC/MS (A): tr=0.24 min; [M+H]+: m/z 347.

Example 2

2.1. 4-([2-(2,6-bis-[(S)-2-eth-(E)-ylidene-7-dimethoxy-1,2,3,11a-tetrahydro-pyrrolo[2,1c][1.4] benzodiazepin-5-one-8-yloxymethyl]-pyridin-4-yloxy)-ethyl]-{2-[2-(2-methoxy-ethoxy)-ethoxy]-ethyl}-amino)-butanoic acid

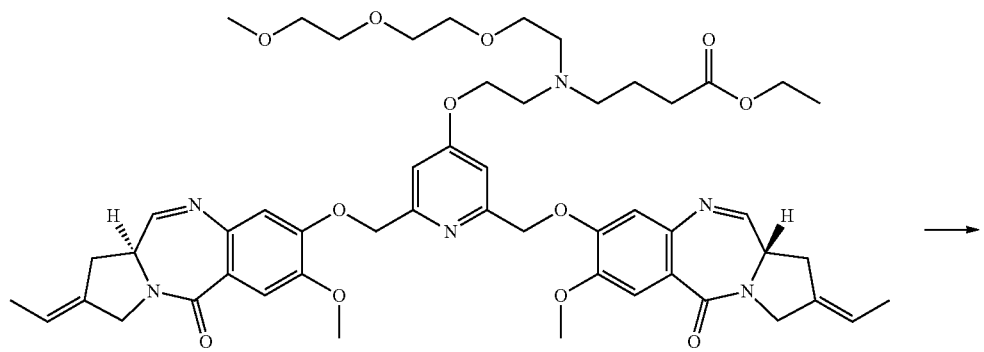

-continued

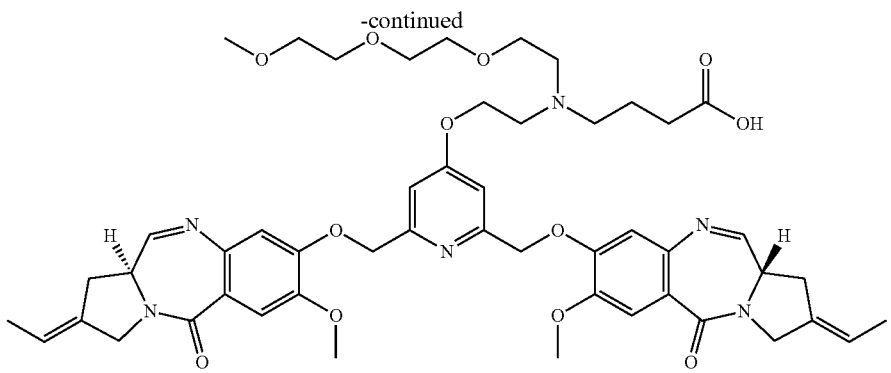

To a solution of 28 mg of ethyl 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-butanoate in 527 µl of THF and 61 µl of water was added 32 µl of an aqueous 1 M lithium hydroxide solution. The mixture was stirred for 1 hour 30 minutes at room temperature and a further 5 µl of aqueous 1 M lithium hydroxide solution were added thereto. After stirring for 1 hour 30 minutes at room temperature, the mixture was acidified to a pH close to 3 by adding 800 µl of potassium phosphate buffer (pH=3) and then extracted 5× with DCM. The organic phases were combined, dried over MgSO₄, concentrated under reduced pressure and purified by flash chromatography on silica (Analogix Super Flash SiO₂ SF10-4g), using a gradient of 3 to 20% MeOH in DCM. The fractions containing the desired product were combined and concentrated under reduced pressure. 10.2 mg of 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-butanoic acid were obtained. LC/MS (B): tr=3.08 min; [M+H]⁺: m/z 939.

2.2. Ethyl 4-([2-(2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-butanoate

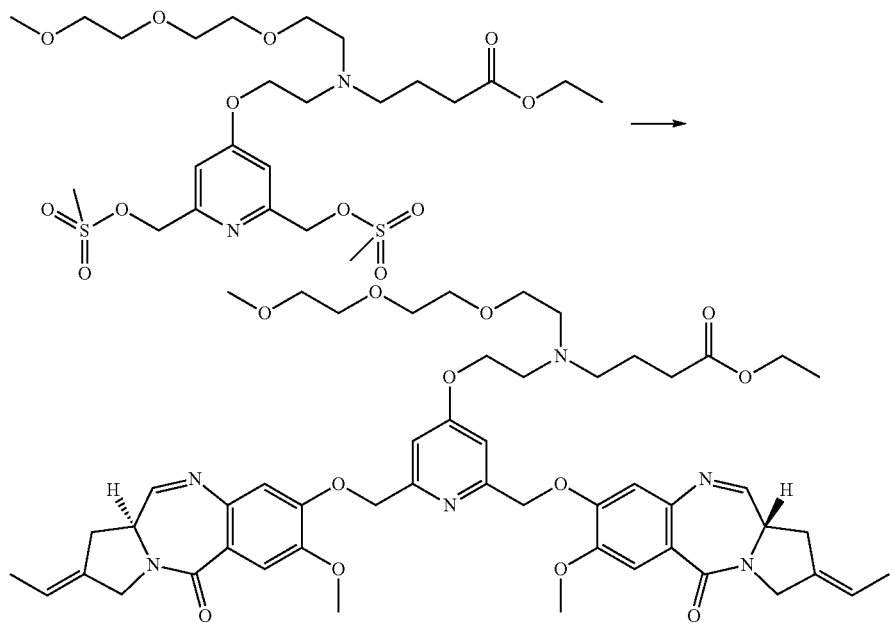

To a solution of 50.4 mg of (S)-2-eth-(E)-ylidene-8-hydroxy-7-methoxy-1,2,3,11a-tetrahydro-pyrrolo[2.1-c][1.4]benzodiazepin-5-one in 4 ml of DMF was added 77 mg of K₂CO₃, 30.7 mg of potassium iodide and 67 mg of ethyl 4-([2-(2,6-bis-methanesulfonyloxymethyl-pyridin-4-yloxy)-ethyl]-{2-[2-(2-methoxy-ethoxy)-ethoxy]-ethyl}-amino)-butyrate. The mixture was heated for 18 hours at 30° C. and then cooled to room temperature, filtered through a 0.45 µm membrane, concentrated under reduced pressure and purified by flash chromatography on silica (Analogix Super Flash SiO₂ SF15-12g), using a gradient of 0 to 10% MeOH in DCM. The fractions containing the desired product were combined and concentrated under reduced pressure. 51 mg of ethyl 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxyethoxy)-ethoxy]ethyl}-amino)-butanoate were obtained. LC/MS (B): tr=3.20 min; [M+H]+: m/z 967.

2.3. Ethyl ([2-(2,6-bis-methanesulfonyloxymethyl-pyridin-4-yloxy)-ethyl]-{2-[2-(2-methoxy-ethoxy)-ethoxy]-ethyl}-amino)-butyrate

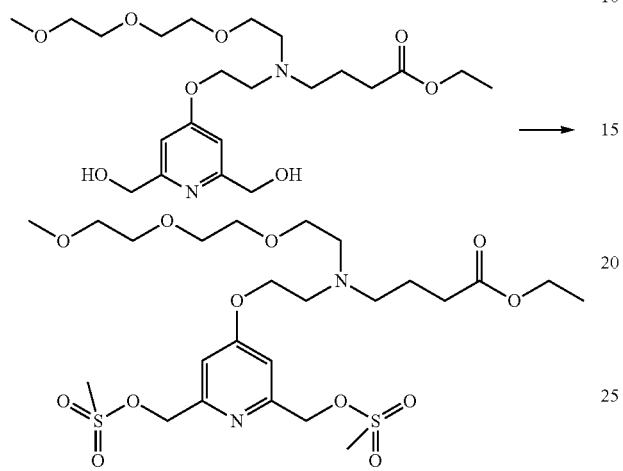

To a solution of 51 mg of ethyl 4-([2-(2,6-bis-hydroxymethyl-pyridin-4-yloxy)-ethyl]-{2-[2-(2-methoxy-ethoxy)-ethoxy]-ethyl}-amino)-butanoate in 5 ml of DCM, precooled to −25° C., was added 110 µl of diisopropylethylamine and 34 µl of MSC. The mixture was stirred for 1 hour at −15° C. and then washed with 5 ml of water. The aqueous phase was extracted with 5 ml of DCM. The organic phases were combined, dried over MgSO$_4$ and concentrated under reduced pressure. 69 mg of ethyl 4-([2-(2,6-bis-methanesulfonyloxymethyl-pyridin-4-yloxy)-ethyl]-{2-[2-(2-methoxy-ethoxy)-ethoxy]-ethyl}-amino)-butyrate were obtained. LC/MS (B): tr=2.87 min; [M+H]+: m/z 615.

2.4. Ethyl 4-([2-(2,6-bis-hydroxymethyl-pyridin-4-yloxy)-ethyl]-{2-[2-(2-methoxy-ethoxy)-ethoxy]-ethyl}-amino)-butanoate

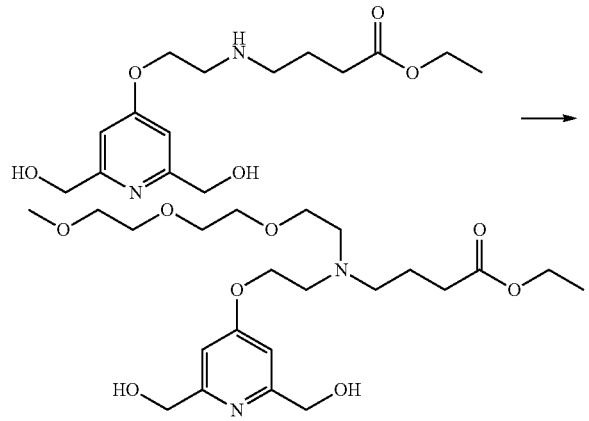

To a solution of 180 mg of ethyl 4-[2-(2,6-bis-hydroxymethyl-pyridin-4-yloxy)-ethylamino]-butanoate in 18 ml of acetonitrile was added 207 mg of 1-iodo-2-[2-(2-methoxy-ethoxy)-ethoxy]-ethane and 192 µl of diisopropylethylamine. The mixture was heated for 3 days at 80° C. and then concentrated under reduced pressure and purified by flash chromatography on silica (Merck SuperVarioFlash 15 g column, Si60 15-40 µm), using a DCM/MeOH/water mixture (40/5/0.5). The fractions containing the desired product were combined and concentrated under reduced pressure. 51 mg of ethyl 4-([2-(2,6-bis-hydroxymethyl-pyridin-4-yloxy)-ethyl]-{2-[2-(2-methoxy-ethoxy)-ethoxy]-ethyl}-amino)-butanoate were obtained. LC/MS (B): tr=0.70 min; [M+H]+: m/z 459.

2.5. Ethyl 4-[2-(2,6-bis-hydroxymethyl-pyridin-4-yloxy)-ethylamino]-butanoate

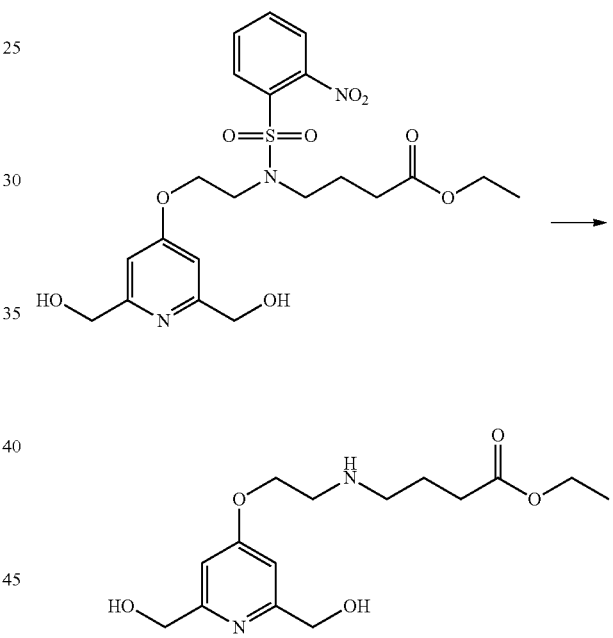

To a solution of 390 mg of ethyl 4-[[2-(2,6-bis-hydroxymethyl-pyridin-4-yloxy)ethyl]-(2-nitro-benzenesulfonyl)-amino]-butanoate in 10 ml of acetonitrile, under argon, was added 766 mg of caesium carbonate and 160 µl of thiophenol. The mixture was stirred for 17 hours at room temperature and then filtered through a sinter of porosity 4. The cake was washed with EtOAc and the filtrate was concentrated under reduced pressure and purified on a Mega BE-SCX, 2GM 12ML cartridge (Varian), using washing with MeOH and detachment of the expected product with a 2N solution of ammonia in MeOH. The fractions containing the desired product were combined and concentrated under reduced pressure. 183 mg of ethyl 4-[2-(2,6-bis-hydroxymethyl-pyridin-4-yloxy)-ethylamino]-butanoate were obtained. LC/MS (B): tr=0.68 min; [M+H]+: m/z 313.

2.6. Ethyl 4-[[2-(2,6-bis-hydroxymethyl-pyridin-4-yloxy)-ethyl]-(2-nitro-benzenesulfonyl)-amino]-butanoate

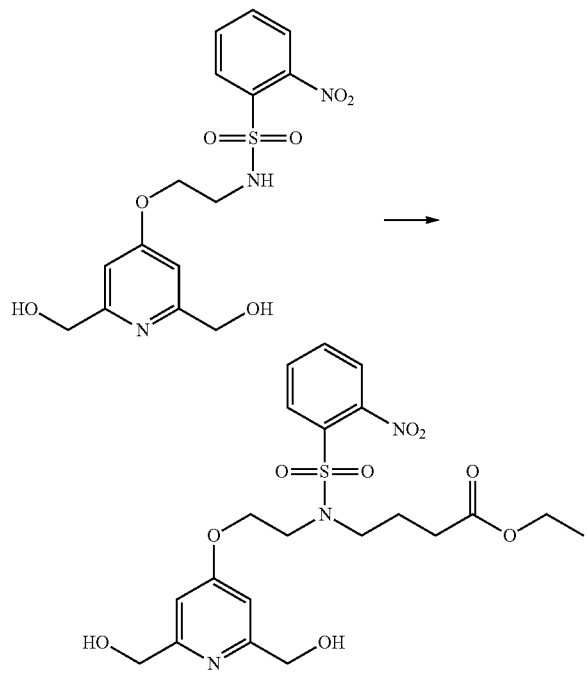

To a solution of 767 mg of N-[2-(2,6-bis-hydroxymethyl-pyridin-4-yloxy)-ethyl]-2-nitro-benzenesulfonamide in 15 ml of DMF, under argon, was added 344 µl of ethyl 3-bromobutyrate and 1.38 g of K$_2$CO$_3$. The mixture was stirred for about 20 hours at 40° C. and then filtered through a sinter of porosity 4. The cake was washed with EtOAc and the filtrate was concentrated under reduced pressure. The crude product was purified by flash chromatography on silica (Merck SuperVarioPrep 90 g column, Si60 15-40 µm), using a gradient of 0 to 10% MeOH in DCM. The fractions containing the desired product were combined and concentrated under reduced pressure. 395 mg of ethyl 4-[[2-(2,6-bis-hydroxymethyl-pyridin-4-yloxy)-ethyl]-(2-nitro-benzenesulfonyl)-amino]-butanoate were obtained. LC/MS (B): tr=2.72 min; [M+H]$^+$: m/z 498; [M+HCO$_2$H−H]$^−$: m/z 542.

2.7. N-[2-(2,6-Bis-hydroxymethyl-pyridin-4-yloxy)-ethyl]-2-nitro-benzenesulfonamide

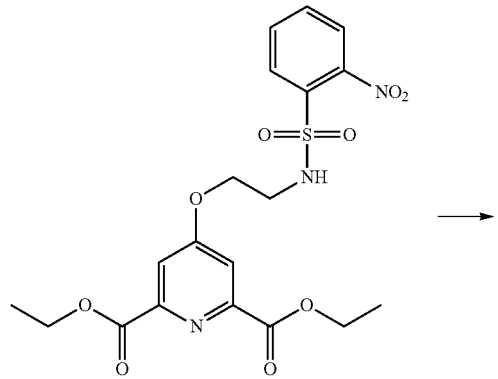

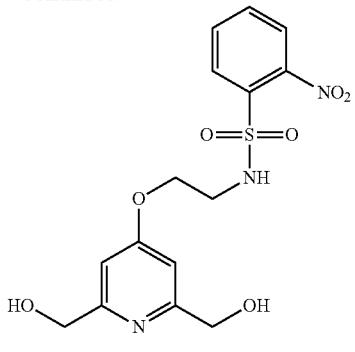

To a solution of 1.3 g of diethyl 4-[2-(2-nitro-benzenesulfonylamino)-ethoxy]-pyridine-2,6-dicarboxylate in 200 mL of ethanol was successively added 315 mg of sodium borohydride and 941 mg of CaCl$_2$. The mixture was stirred for 1 hour 30 minutes at room temperature and 50 ml of water were then added thereto. The ethanol was removed under reduced pressure and 50 ml of water were added to the residue obtained; the aqueous phase was extracted 3× with EtOAc. The organic phases were combined, washed with saturated NaCl solution, dried over MgSO$_4$ and concentrated under reduced pressure. 1.06 g of N-[2-(2,6-bis-hydroxymethyl-pyridin-4-yloxy)-ethyl]-2-nitro-benzenesulfonamide were obtained. LC/MS (A): tr=0.57 min; [M+H]$^+$: m/z 384.

2.8. Diethyl 4-[2-(2-nitro-benzenesulfonylamino)-ethoxy]-pyridine-2,6-dicarboxylate

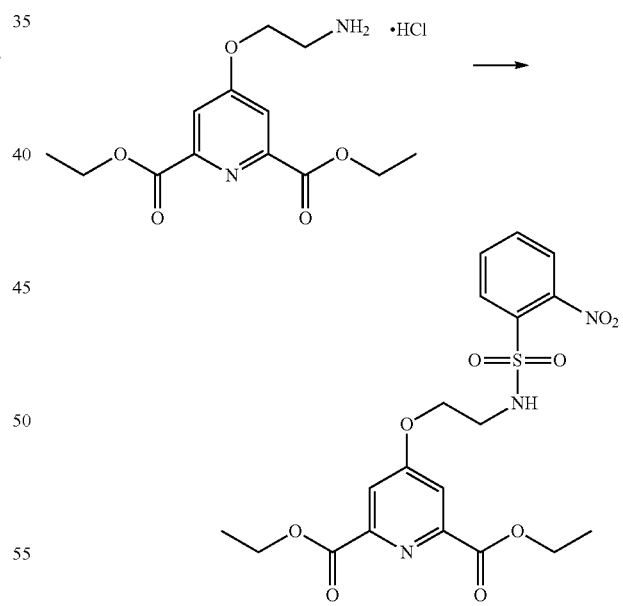

To a solution of 957 mg of diethyl 4-(2-amino-ethoxy)-pyridine-2,6-dicarboxylate monohydrochloride in 30 ml of DCM and 734 µl of pyridine, precooled to about 5° C., was added 798 mg of 2-nitrobenzenesulfonyl chloride. The mixture was warmed to room temperature and stirred for 2 hours. A further 244 µl of pyridine and 665 mg of 2-nitrobenzenesulfonyl chloride were then added thereto and stirring was continued for 15 hours. The mixture was washed with 25 ml of water and the aqueous phase was extracted 2× with 25 ml of DCM. The organic phases were combined, dried over MgSO₄, concentrated under reduced pressure and purified by flash chromatography on silica (Merck EasyVarioPrep 150 g column, Si60 15-40 µm), using a gradient of 0 to 10% EtOAc in DCM. The fractions containing the desired product were combined and concentrated under reduced pressure. 960 mg of diethyl 4-[2-(2-nitro-benzenesulfonylamino)-ethoxy]-pyridine-2,6-dicarboxylate were obtained. ¹H NMR (400 MHz, DMSO-d₆): 1.35 (t, J=7.2 Hz, 6H); 3.41 (t, J=5.2 Hz, 2H); 4.22 (t, J=5.2 Hz, 2H); 4.39 (q, J=7.2 Hz, 4H); 7.50 (s, 2H); 7.80 (m, 2H); 7.92 (m, 1H); 8.04 (m, 2H); 8.40 (m, 1H). LC/MS (C): tr=3.50 min; [M+H]⁺: m/z 468.

2.9. Diethyl 4-(2-amino-ethoxy)-pyridine-2,6-dicarboxylate monohydrochloride

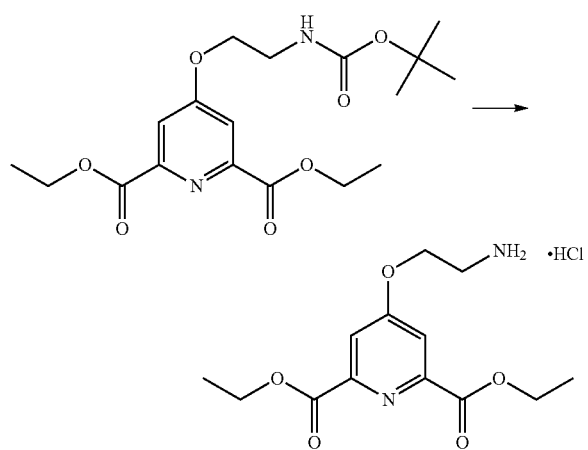

To a solution of 2.64 g of diethyl 4-(2-tert-butoxycarbonylamino-ethoxy)-pyridine-2,6-dicarboxylate (described on page 101 of WO 07085930) in 27 ml of dioxane was added 20.7 ml of 4N hydrochloric acid in dioxane. The mixture was stirred for about 20 hours at room temperature and then concentrated under reduced pressure. The evaporation residue was taken up in about 70 ml of dioxane, and then concentrated again under reduced pressure. The operation was repeated 3×. The mixture was taken up in 50 ml of tert-butyl methyl ether and the suspension obtained was filtered through a sinter of porosity 4. The cake was washed with tert-butyl methyl ether, and dried in a desiccator under reduced pressure at room temperature. 2 g of diethyl 4-(2-amino-ethoxy)-pyridine-2,6-dicarboxylate monohydrochloride were obtained. ¹H NMR (400 MHz, DMSO-ds): 1.35 (t, J=7.2 Hz, 6H); 3.26 (m, 2H); 4.39 (q, J=7.2 Hz, 4H); 4.45 (m, 2H); 7.77 (s, 2H); 8.16 (broad m, 3H). LC/MS (C): tr=2.39 min; [M+H]⁺: m/z 283.

Example 3

3.1. 3-([2-(2,6-Bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-propanoic acid

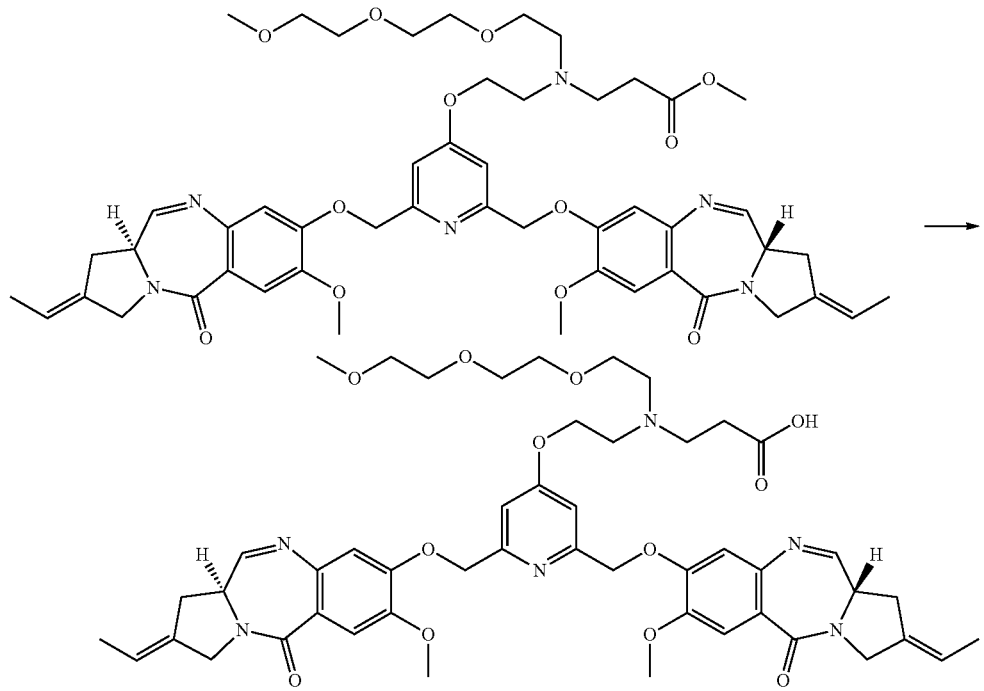

To a solution of 30 mg of methyl 3-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-propanoate in 576 µl of THF and 67 µl of water was added 35 µl of an aqueous 1 M lithium hydroxide solution. The mixture was stirred for 1 hour 30 minutes at room temperature and then taken up in 4 ml of DCM and acidified to a pH close to 3 by adding 1 ml of potassium phosphate buffer (pH=3). The mixture was extracted 4× with DCM and the organic phases were combined, dried over MgSO$_4$, concentrated under reduced pressure and purified by flash chromatography on silica (Analogix Super Flash SiO$_2$ SF10-4g), using a gradient of 10 to 20% MeOH in DCM. The fractions containing the desired product were combined and concentrated under reduced pressure. 13 mg of 3-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-propanoic acid were obtained. LC/MS (B): tr=3.07 min; [M+H]$^+$: m/z 925

3.2. Methyl 3-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2(2-methoxy-ethoxy)-ethoxy]-ethyl}-amino)-propanoate (2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-{2-[2-(2-methoxy-ethoxy)-ethoxy]-ethyl}-amino)-propanoate were obtained. LC/MS (B): tr=3.21 min; [M+H]$^+$: m/z 939

3.3. Methyl 3-([2-(2,6-bis-methanesulfonyloxymethyl-pyridin-4-yloxy)-ethyl]-{2-[2-(2 methoxy-ethoxy)-ethoxy]-ethyl}-amino)-propanoate

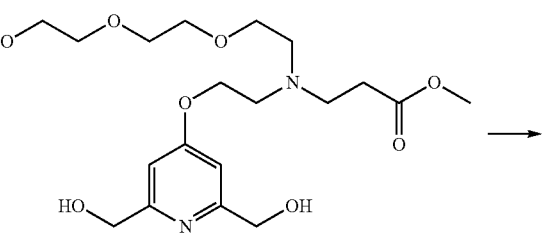

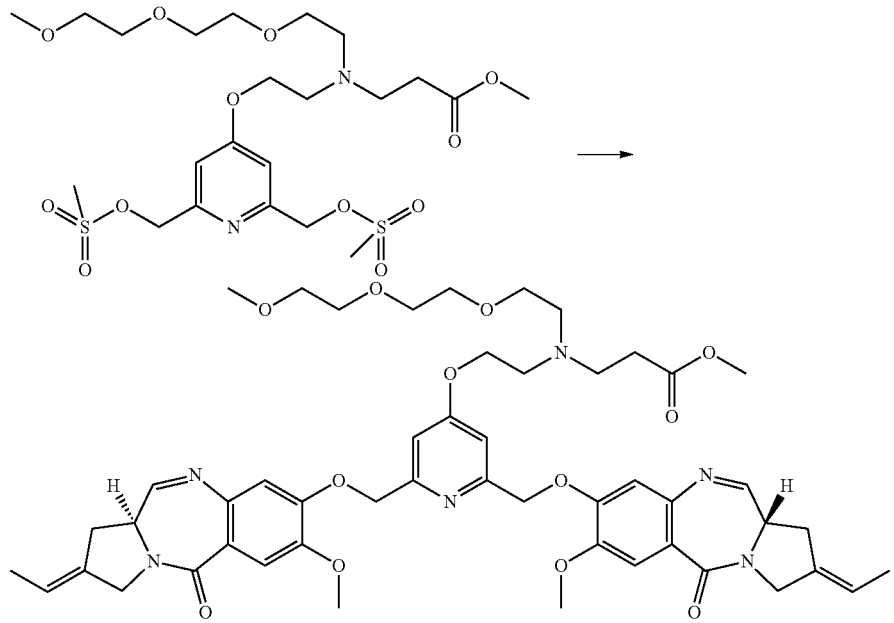

To a solution of 84 mg of (S)-2-eth-(E)-ylidene-8-hydroxy-7-methoxy-1,2,3,11a-tetrahydro-pyrrolo[2.1-c][1.4]benzodiazepin-5-one in 5 ml of DMF was added 128 mg of K$_2$CO$_3$, 51 mg of KI and 110 mg of methyl 3-([2-(2,6-bis-methanesulfonyloxymethyl-pyridin-4-yloxy)-ethyl]-{2-[2-(2-methoxy-ethoxy)-ethoxy]-ethyl}-amino)-propanoate. The mixture was heated for 18 hours at 30° C. and then cooled to room temperature, filtered through a 0.45 µm membrane, concentrated under reduced pressure and purified by flash chromatography on silica (Analogix Super Flash SiO$_2$ SF15-24g), using a gradient of 0 to 10% MeOH in DCM. The fractions containing the desired product were combined and concentrated under reduced pressure. 33 mg of methyl 3-([2-

-continued

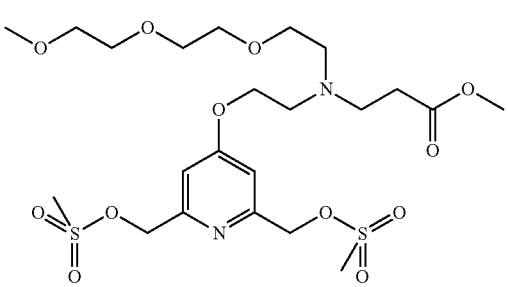

To a solution of 80 mg of methyl 3-([2-(2,6-bis-hydroxymethyl-pyridin-4-yloxy)-ethyl]-{2-[2-(2-methoxy-ethoxy)-ethoxy]-ethyl}-amino)-propanoate in 8 ml of DCM, precooled to −25° C., was added 183 µl of diisopropylethylamine and 57 µl of methanesulfonyl chloride. The mixture was stirred for 1 hour at −15° C. and then washed with 5 ml of water. The aqueous phase was extracted with 5 ml of DCM. The organic phases were combined, dried over MgSO₄ and concentrated under reduced pressure. 110 mg of methyl 3-([2-(2,6-bis-methanesulfonyloxymethyl-pyridin-4-yloxy)-ethyl]-{2-[2-(2-methoxy-ethoxy)-ethoxy]-ethyl}-amino)-propanoate were obtained. LC/MS (B): tr=2.67 min; [M+H]⁺: m/z 587

3.4. Methyl 3-([2-(2,6-bis-hydroxymethyl-pyridin-4-yloxy)-ethyl]-{2-[2-(2-methoxy-ethoxy)-ethoxy]-ethyl}-amino)-propanoate

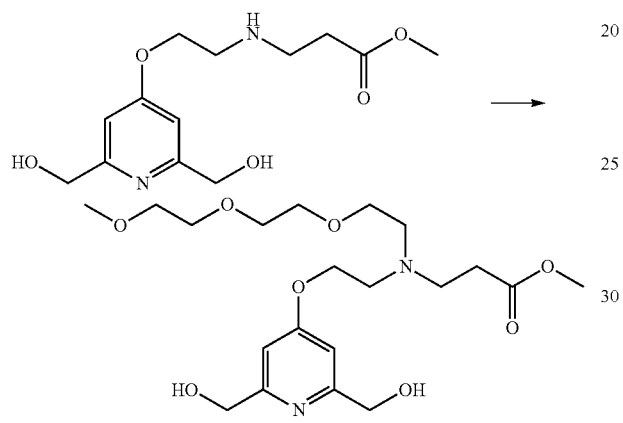

To a solution of 284 mg of methyl 3-[2-(2,6-bis-hydroxymethyl-pyridin-4-yloxy)-ethylamino]-propanoate in 28 ml of acetonitrile was added 356 mg of 1-iodo-2-[2-(2-methoxy-ethoxy)-ethoxy]-ethane and 330 µl of diisopropylethylamine. The mixture was heated at 80° C. for 3 days and then concentrated under reduced pressure and purified by flash chromatography on silica (Analogix Super Flash SiO₂ SF25-40g), using a gradient of 5 to 10% MeOH in DCM. The fractions containing the desired product were combined and concentrated under reduced pressure. 165 mg of methyl 3-([2-(2,6-bis-hydroxymethyl-pyridin-4-yloxy)-ethyl]-{2-[2-(2-methoxy-ethoxy)-ethoxy]-ethyl}-amino)-propanoate were obtained. LC/MS (B): tr=0.44 min; [M+H]⁺: m/z 431.

3.5. Methyl 3-[2-(2,6-bis-hydroxymethyl-pyridin-4-yloxy)-ethylamino]-propanoate

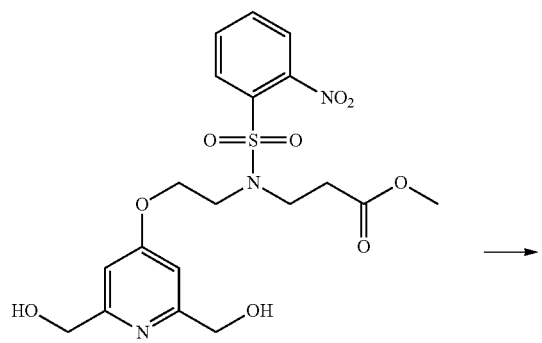

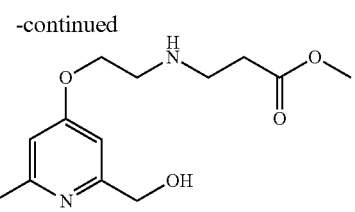

To a solution of 155 mg of methyl 3-[[2-(2,6-bis-hydroxymethyl-pyridin-4-yloxy)-ethyl]-(2-nitro-benzenesulfonyl)-amino]-propanoate in 6 ml of acetonitrile, under argon, was added 325 mg of caesium carbonate and 67 µl of thiophenol. The mixture was stirred for 4 hours at room temperature and then filtered through a sinter of porosity 4. The cake was washed with EtOAc and the filtrate was concentrated under reduced pressure and purified on a Mega BE-SCX, 2GM 12ML cartridge (Varian), using washing with MeOH and detachment of the expected product with a 2N solution of ammonia in MeOH. The fractions containing the desired product were combined and concentrated under reduced pressure. 82 mg of methyl 3-[2-(2,6-bis-hydroxymethyl-pyridin-4-yloxy)-ethylamino]-propanoate were obtained. LC/MS (B): tr=0.33 min; [M+H]⁺: m/z 285.

3.6. Methyl 3-[[2-(2,6-bis-hydroxymethyl-pyridin-4-yloxy)-ethyl]-(2-nitro-benzenesulfonyl)-amino]-propanoate

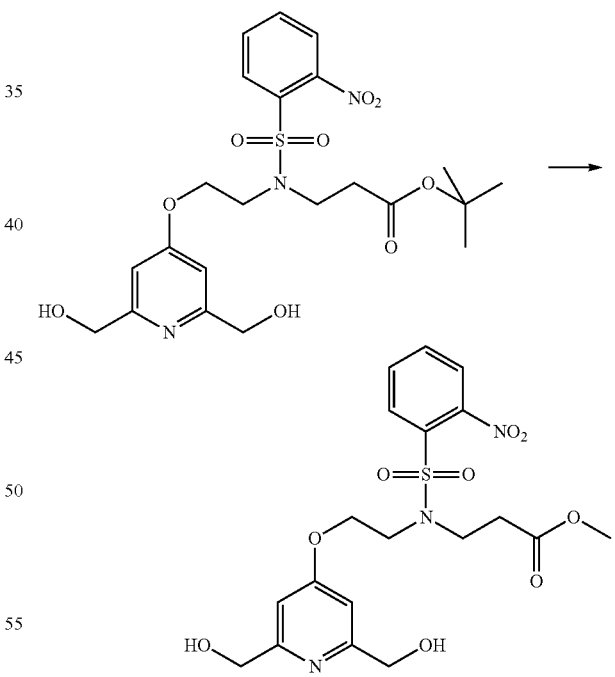

To a solution of 670 mg of tert-butyl 3-[2-(2,6-bis-hydroxymethyl-pyridin-4-yloxy)-ethylamino]-propanoate in 20 ml of DCM was added 2 ml of TFA. The mixture was stirred for 6 hours at room temperature and then concentrated under reduced pressure, taken up in DCM and concentrated again under reduced pressure. To the residue obtained, dissolved in 10 ml of MeOH, was added, at 5° C., 7 ml of a 2M solution of (trimethylsilyl)diazomethane in hexane. The mixture was stirred for 1 hour 30 minutes at 5° C. and then 200 µl of acetic acid were added. The mixture was taken up in 30 ml of water and 30 ml of EtOAc. The aqueous phase was extracted 2× with 30 ml of EtOAc. The organic phases were combined, washed with saturated NaCl solution, concentrated under reduced pressure and purified by flash chromatography on silica (Analogix Super Flash SiO₂ SF15-24g), using a gradient of 0 to 10% MeOH in DCM. The fractions containing the desired product were combined and concentrated under reduced pressure. 155 mg of methyl 3-[2-(2,6-bis-hydroxymethyl-pyridin-4-yloxy)-ethylamino]-propanoate were obtained. LC/MS (C): tr=2.56 min; [M+H]⁺: m/z 470.

3.7. tert-Butyl 3-[[2-(2,6-bis-hydroxymethyl-pyridin-4-yloxy)-ethyl]-(2-nitro-benzenesulfonyl)-amino]-propanoate

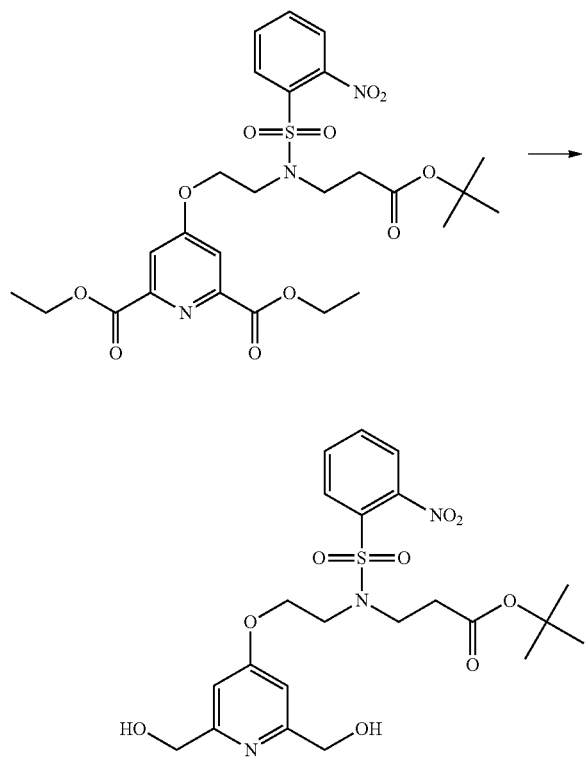

To a solution of 0.8 g of diethyl 4-{2-[(2-tert-butoxycarbonyl-ethyl)-(2-nitro-benzenesulfonyl)-amino]-ethoxy}-pyridine-2,6-dicarboxylate in 80 mL of ethanol were successively added 152 mg of sodium borohydride and 447 mg of CaCl₂. The mixture was stirred at room temperature and 20 ml of water were then added at the end of the reaction. The ethanol was removed under reduced pressure, 100 ml of water were added to the residue obtained and the aqueous phase was extracted 3× with EtOAc. The organic phases were combined, washed with saturated NaCl solution, dried over MgSO₄ and concentrated under reduced pressure. 670 mg of tert-butyl 3-[[2-(2,6-bis-hydroxymethyl-pyridin-4-yloxy)-ethyl]-(2-nitro-benzenesulfonyl)-amino]-propanoate were obtained. LC/MS (C): tr=3 min; [M+H]⁺: m/z 512.

3.8. Diethyl 4-{2-[(2-tert-butoxycarbonyl-ethyl)-(2-nitro-benzenesulfonyl)-amino]-ethoxy}-pyridine-2,6-dicarboxylate

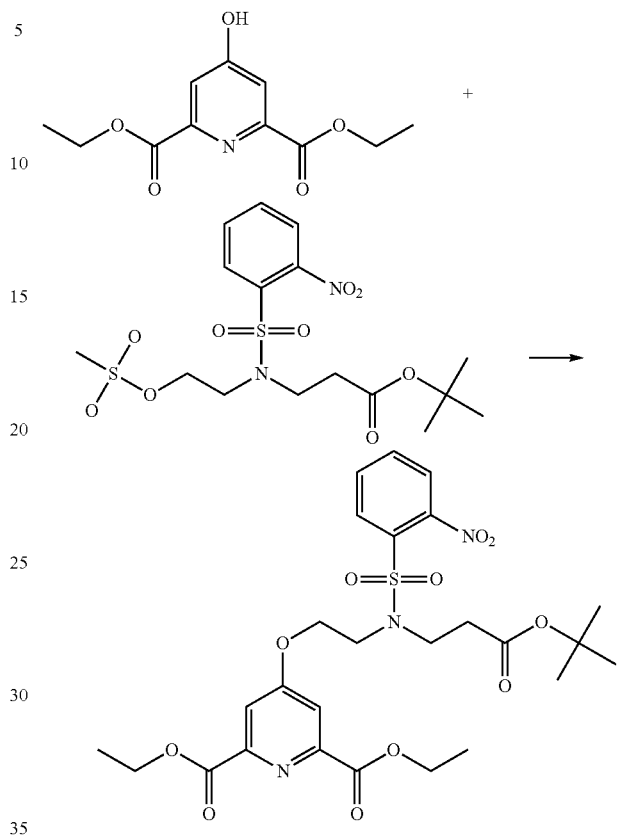

To a solution of 10.6 g of tert-butyl 3-[(2-methanesulfonyloxy-ethyl)-(2-nitro-benzenesulfonyl)-amino]-propionate in 220 ml of DMF was added 16.2 g of K₂CO₃ and 5.6 g of diethyl 4-hydroxy-pyridine-2,6-dicarboxylate. The mixture was heated for 20 hours at 60° C. and then concentrated under reduced pressure and taken up in 200 ml of water and 200 ml of EtOAc. The aqueous phase was extracted 2× with EtOAc. The organic phases were combined, washed with saturated NaCl solution, dried over MgSO₄, concentrated under reduced pressure and purified by flash chromatography on silica (Merck EasyVarioPrep 600 g column, Si60 15-40 μm), using a gradient of 0 to 20% EtOAc in DCM. The fractions containing the desired product were combined and concentrated under reduced pressure. 6.56 g of diethyl 4-{2-[(2-tert-butoxycarbonyl-ethyl)-(2-nitro-benzenesulfonyl)-amino]-ethoxy}-pyridine-2,6-dicarboxylate were obtained. LC/MS (C): tr=4.14 min; [M+H]⁺: m/z 596.

3.9. tert-Butyl 3-[(2-methanesulfonyloxy-ethyl)-(2-nitro-benzenesulfonyl)-amino]-propionate

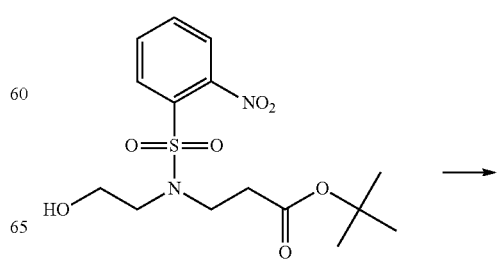

107

-continued

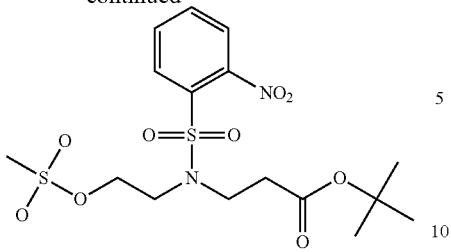

To a solution of 9.2 g of tert-butyl 3-[(2-hydroxy-ethyl)-(2-nitro-benzenesulfonyl)-amino]-propionate in 92 ml of DCM was added 8.1 ml of diisopropylethylamine. The mixture was cooled to −5° C. and a solution of 2.34 ml of MSC in 10 ml of DCM was added dropwise. After warming to room temperature, the mixture was stirred for about 2 hours and was then supplemented with 100 ml of water. The aqueous phase was extracted twice with DCM and the organic phases were combined, dried over $MgSO_4$, concentrated under reduced pressure and purified by flash chromatography on silica (Analogix Super Flash $SiO_2$ SF40-240g), using a gradient of 0 to 5% of ethyl acetate in DCM. The fractions containing the desired product were combined and concentrated under reduced pressure. 10.62 g of tert-butyl 3-[(2-methanesulfonyloxy-ethyl)-(2-nitro-benzenesulfonyl)-amino]-propionate were obtained. LC/MS (C): tr=3.77 min; $[M+Na]^+$: m/z 475.

3.10. tert-Butyl 3-[(2-Hydroxy-ethyl)-(2-nitro-benzenesulfonyl)-amino]-propionate

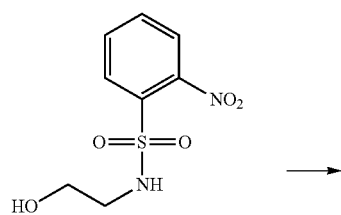

108

-continued

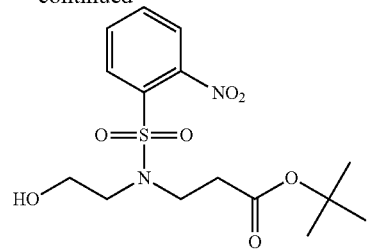

To a solution of 8.7 g of N-(2-hydroxy-ethyl)-2-nitro-benzenesulfonamide (Skerlj, R. T.; Nan, S.; Zhou, Y.; Bridger, G. J. *Tetrahedron Lett.* 2002 (43) 7569-7571) in 87 ml of DMF, under argon, was added 8.8 ml of tert-butyl 3-bromopropionate and 14.6 g of $K_2CO_3$. The mixture was stirred for 15 hours at 40° C. and a further 5 ml of tert-butyl 3-bromopropionate were then added. The mixture was heated at 40° C. overnight and then filtered through a sinter of porosity 4. The cake was washed with ethyl acetate and the filtrate was then concentrated under reduced pressure and purified by flash chromatography on silica (Merck EasyVarioPrep 400 g column, Si60 15-40 µm), using a gradient of 0 to 10% EtOAc in DCM. The fractions containing the desired product were combined and concentrated under reduced pressure. 9.54 g of tert-butyl 3-[(2-hydroxy-ethyl)-(2-nitro-benzenesulfonyl)-amino]-propionate were obtained. LC/MS (C): tr=3.39 min; $[M+Na]^+$: m/z 397.

Example 4

4.1. 4-[2-((2-methyl-2-methyldisulfanyl-propyl)-{2-[2-(2-morpholin-4-yl-ethoxy)-ethoxy]-ethyl}-amino)-ethoxy]-2,6-bis-[(S)-2-eth-(E)-ylidene-7-dimethoxy-1,2,3,11a-tetrahydro pyrrolo[2,1c][1.4] benzodiazepin-5-one-8-yloxymethyl]-pyridine Prepared as for Ex. 1, starting with 4-[2-((2-methyl-2-methyldisulfanyl-propyl)-{2-[2-(2-morpholin-4-yl-ethoxy)-ethoxy]-ethyl}-amino)-ethoxy]-2,6-bis-(hydroxy methyl)-pyridine:

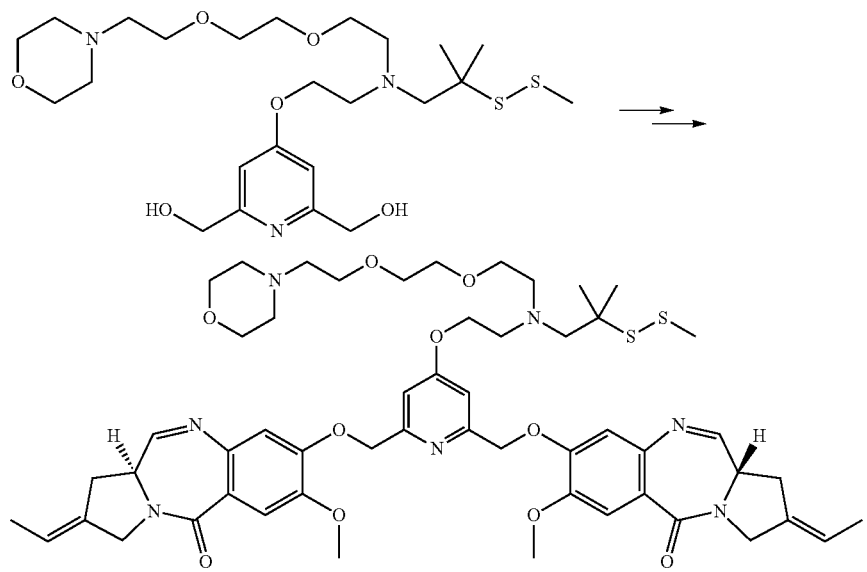

¹H NMR (500 MHz, DMSO-d₆): 1.22 (s, 6H); 1.69 (d, J=7.0 Hz, 6H); 2.28 to 2.44 (m, 6H); 2.36 (m, 3H); 2.71 (s, 2H); 2.77 (t, J=6.7 Hz, 2H); 2.88 to 3.08 (m, 6H); 3.42 to 3.55 (m, 12H); 3.86 (s, 6H); 3.88 (m, 2H); 4.10 (s, 4H); 4.15 (t, J=5.7 Hz, 2H); 5.17 (d, J=13.2 Hz, 2H); 5.23 (d, J=13.2 Hz, 2H); 5.55 (m, 2H); 6.93 (s, 2H); 7.06 (s, 2H); 7.38 (s, 2H); 7.76 (d, J=4.4 Hz, 2H). LC/MS (A): tr=0.68 min; [M+H]⁺: m/z 1042; [M+2H]²⁺: m/z 521.5 (base peak)

4.2. 4-[2-((2-methyl-2-methyldisulfanyl-propyl)-{2-[2-(2-morpholin-4-yl-ethoxy)-ethoxy]-ethyl}-amino)-ethoxy]-2,6-bis-(hydroxy methyl)-pyridine Prepared as for Ex. 1, starting with 4-{2-[2-(2-iodo-ethoxy)-ethoxy]-ethyl}-morpholine and 4-[2-(2-methyl-2-methyldisulfanyl-propylamino)-ethoxy]-2,6-bis-(hydroxymethyl)-pyridine:

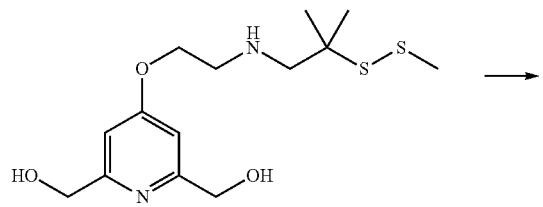

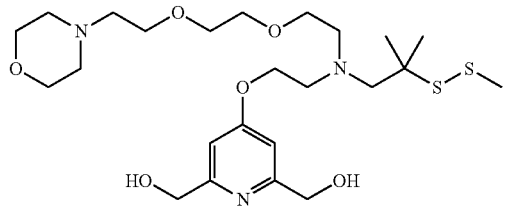

¹H NMR (400 MHz, DMSO-d₆): 1.26 (s, 6H); 2.36 (m, 4H); 2.39 (s, 3H); 2.43 (t, J=5.9 Hz, 2H); 2.74 (s, 2H); 2.79 (t, J=5.9 Hz, 2H); 3.00 (t, J=5.9 Hz, 2H); 3.46 to 3.55 (m, 12H); 4.12 (t, J=5.9 Hz, 2H); 4.45 (d, J=5.9 Hz, 4H); 5.30 (t, J=5.9 Hz, 2H); 6.84 (s, 2H). LC/MS (E): tr=0.33 min; [M+H]⁺: m/z 534

4.3. 4-{2-[2-(2-iodo-ethoxy)-ethoxy]-ethyl}-morpholine

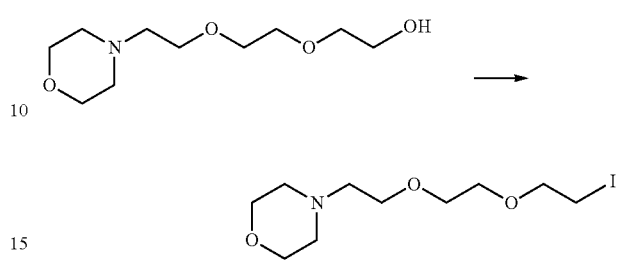

To a solution of 1.12 g of 2-[2-(2-morpholin-4-yl-ethoxy)-ethoxy]-ethanol and 940 µl of diisopropylethylamine in 6 ml of DCM, cooled to 00° C., was added a solution of 440 µl of methanesulfonyl chloride in 3 mL of DCM at the same temperature. The mixture was stirred for 1 hour at 0° C. and then washed with 8 ml of water. The organic phase was dried over MgSO₄ and concentrated under reduced pressure.

The residue obtained was dissolved in 30 ml of acetone and then supplemented with 1.42 g of sodium iodide. After stirring at reflux for 5 hours, the insoluble matter was removed by filtration on a sinter funnel. The filtrate was concentrated under reduced pressure and then taken up in dichloromethane. The insoluble matter was again removed by filtration, and the filtrate was concentrated under reduced pressure and purified by flash chromatography on silica (Analogix Super Flash SiO₂ SF25-40g), using a gradient of 0 to 5% MeOH in DCM. The fractions containing the desired product were combined and concentrated under reduced pressure. 1.09 g of 4-{2-[2-(2-iodo-ethoxy)-ethoxy]-ethyl}-morpholine were obtained. ¹H NMR (400 MHz, DMSO-d₆): 2.39 (m, 4H); 2.45 (t, J=5.9 Hz, 2H); 3.32 (t, J=6.4 Hz, 2H); 3.47 to 3.60 (m, 10H); 3.67 (t, J=6.4 Hz, 2H). LC/MS (A): tr=0.29 min; [M+H]⁺: m/z 330

Example 5

5.1. N-Hydroxysuccinimidyl 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoate

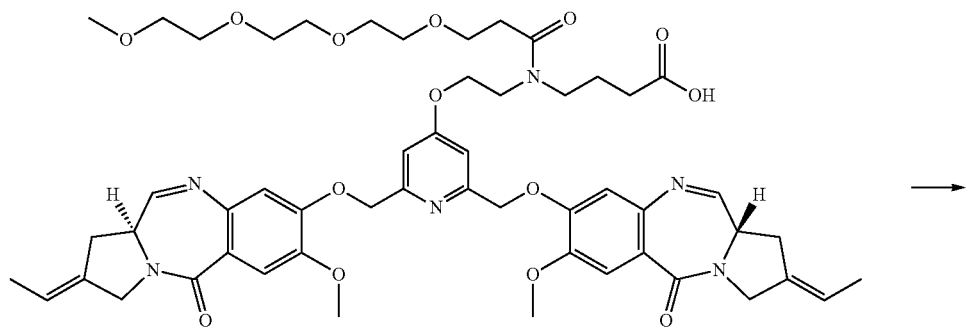

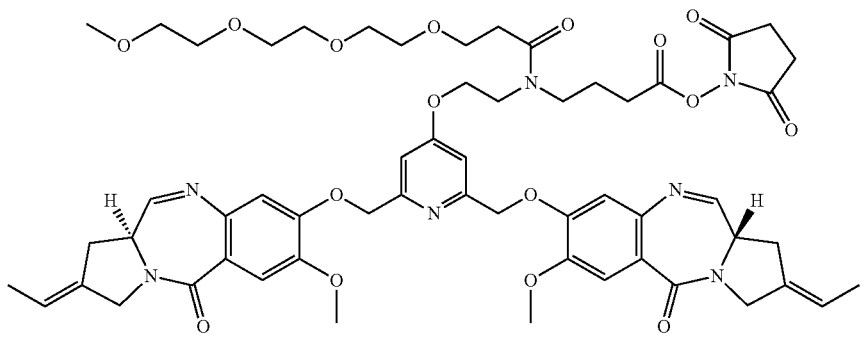

To 65 mg of 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoic acid dissolved in 3.8 mL of THF are added 67 µl of DIPEA and 33 mg of N,N'-disuccinimidyl carbonate. After 1 hour at room temperature, 8 mL of DCM were added and the resulting organic phase was washed twice with water, dried over MgSO$_4$, concentrated under reduced pressure and purified by flash chromatography on silica (Analogix Super Flash SiO$_2$ SF10-8g), using a gradient of 0 to 7.5% methanol in DCM. 35 mg of N-hydroxysuccinimidyl 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoate were thus obtained. LC/MS (F): tr=3.54 min; [M+H]$^+$: m/z 1108; [M+H$_2$O+H]$^+$: m/z 1126; [M+2H$_2$O+H]$^+$: m/z 1144

5.2. 4-([2-(2,6-Bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoic acid Prepared as for Ex. 2, starting with methyl 4-([2-(2,6-bis-[(S)-2-eth-(E)-ylidene-7-dimethoxy-1,2,3,11a-tetrahydro-pyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoate:

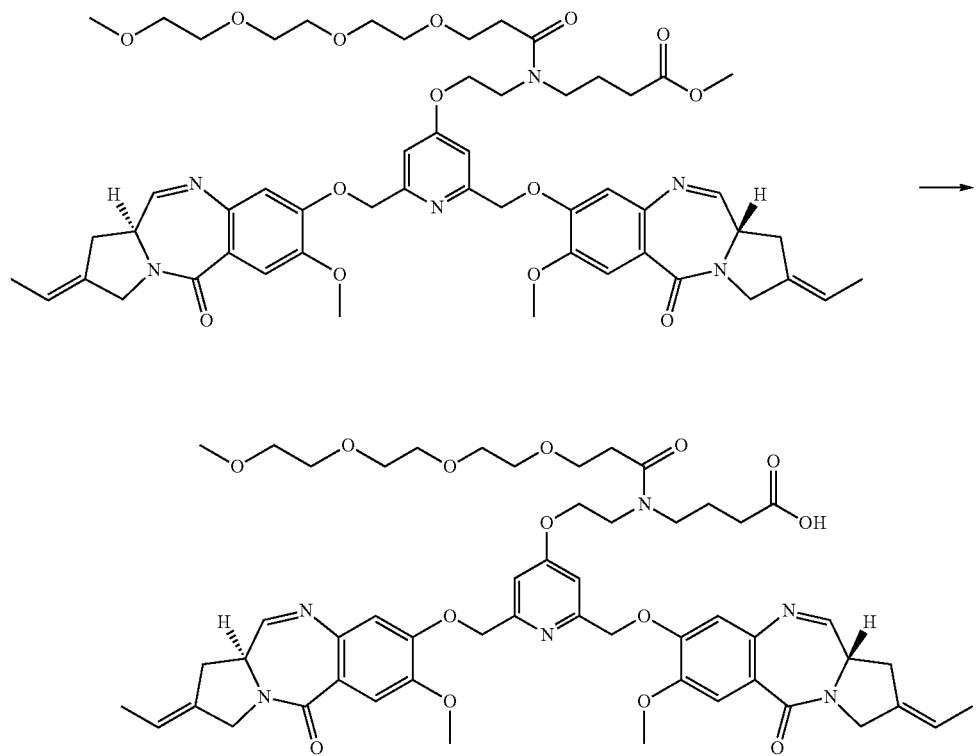

LC/MS (E): tr=1.05 min; [M+H]⁺: m/z 1011; [M+H₂O+H]⁺: m/z 1029; [M+2H₂O+H]⁺: m/z 1047

5.3. Methyl 4-([2-(2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoate Prepared as for Ex. 2, starting with ethyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate:

ethoxy)-ethoxy]-ethoxy}-propionyl)-amino]-butanoate in 7 ml of DCM were added 1.14 ml of TFA. The mixture was stirred for 15 hours at room temperature and then concentrated under reduced pressure. To the residue obtained, dissolved in 3.8 ml of MeOH, was added, at 50° C., 3.1 ml of a 2M solution of (trimethylsilyl)diazomethane in hexane. The mixture was stirred for 1 hour at 5° C. and 100 µl of acetic acid were then added. After concentration under reduced pressure, the residue obtained was purified by flash chromatography on silica (Analogix Super Flash SiO₂ SF25-40g), using a gradient of 2 to 10% MeOH in DCM. The fractions containing the desired product were combined and concentrated under

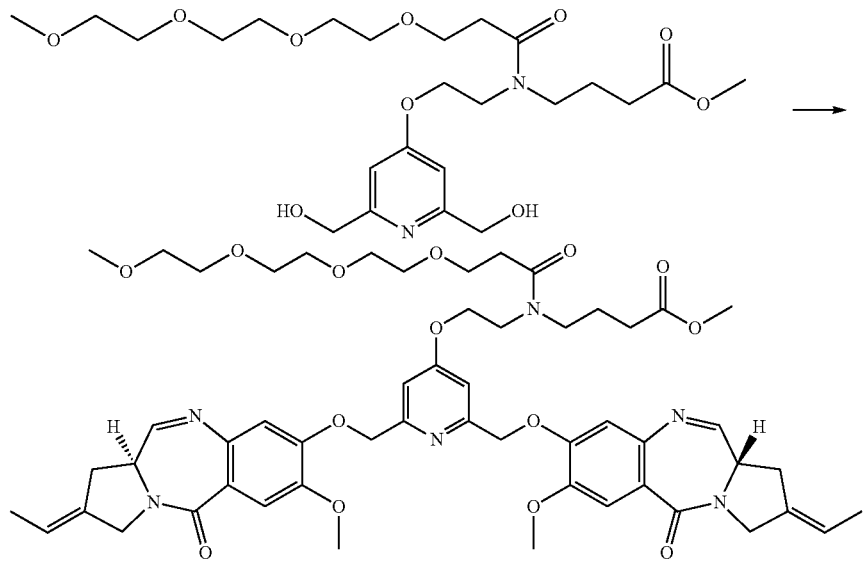

LC/MS (E): tr=1.14 min; [M+H]⁺: m/z 1025; [M+H₂O+H]⁺: m/z 1043; [M+2H₂O+H]⁺: m/z 1061

5.4. Methyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate reduced pressure. 265 mg of methyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate were obtained. ¹H NMR (400 MHz, DMSO-d₆): 50%-50% mixture of conformers with: 1.67 to 1.86 (m, 2H); 2.27 (t, J=7.3 Hz, 1H); 2.36 (t, J=7.3 Hz, 1H); 2.57 (t, J=6.7 Hz, 1H); 2.66

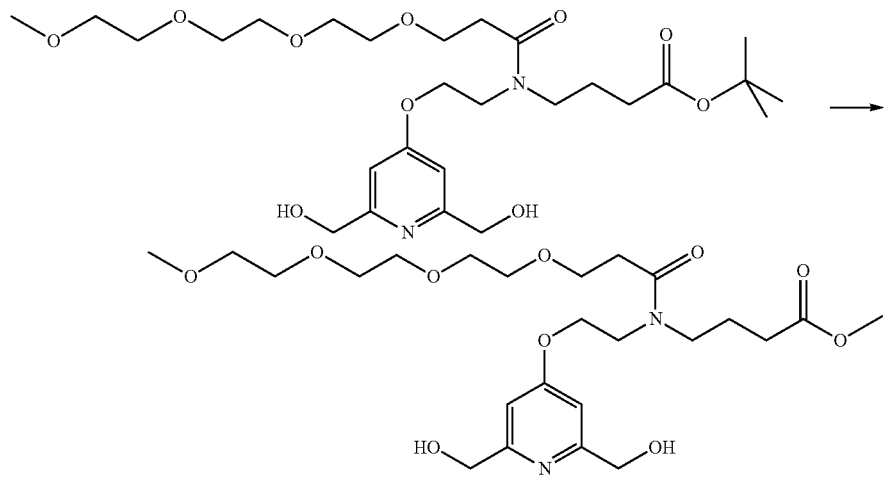

To a solution of 460 mg of tert-butyl 4-[[2-(2,6-bis-hydroxymethyl-pyridin-4-yloxy)-ethyl]-(3-{2-[2-(2-methoxy- (t, J=6.7 Hz, 1H); 3.23 (s, 3H); 3.31 to 3.75 (m, 21H); 4.14 (t, J=5.6 Hz, 1H); 4.19 (t, J=5.6 Hz, 1H); 4.45 (m, 4H); 5.30 (m, 2H); 6.84 (s, 1H); 6.86 (s, 1H). LC/MS (G): tr=0.62 min; [M+H]⁺: m/z 517; [M−H+HCO₂H]⁻: m/z 561

5.5. tert-Butyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate

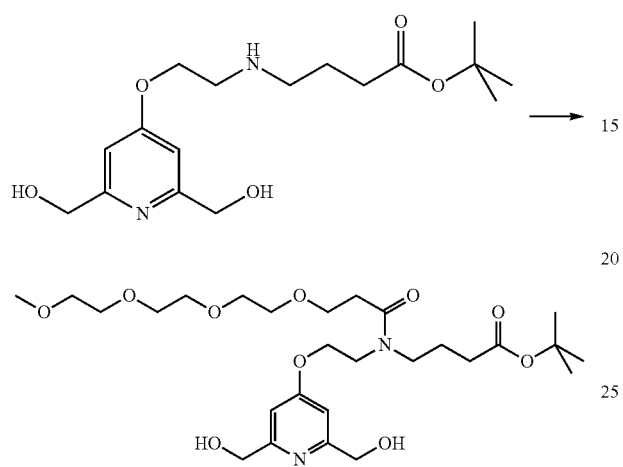

To a solution of 560 mg of tert-butyl 3-[2-(2,6-bis-hydroxymethyl-pyridin-4-yloxy)-ethylamino]-butanoate in 4 ml of DMF was added a solution of 658 mg of N-hydroxysuccinimidyl 3-{2-[2-(2-methoxy-ethoxy)-ethoxy]-ethoxy}-propanoate (cf. M. A. Miller, N. B. Malkar, D. Severynse-Stevens, K. G. Yarbrough, M. J. Bednarcik, R. E. Dugdell, M. E. Puskas, R. Krishnan, K. D. James *Bioconjugate Chem.*, 2006, 17, 267-274) in 4 mL of DMF. The mixture was stirred at room temperature for 15 hours and then concentrated under reduced pressure and purified by flash chromatography on silica (Analogix Super Flash SiO₂ SF40-80g), using a gradient of 0 to 10% of a 10% solution of ammonia in MeOH, in DCM. The fractions containing the desired product were combined and concentrated under reduced pressure. 460 mg of tert-butyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate were obtained. ¹H NMR (400 MHz, DMSO-d₆): 50%-50% mixture of conformers with: 1.39 (s, 4.5H); 1.40 (s, 4.5H); 1.63 to 1.81 (m, 2H); 2.16 (t, J=7.3 Hz, 1H); 2.25 (t, J=7.3 Hz, 1H); 2.57 (t, J=6.7 Hz, 1H); 2.66 (t, J=6.7 Hz, 1H); 3.23 (s, 3H); 3.31 to 3.74 (m, 18H); 4.14 (t, J=5.7 Hz, 1H); 4.19 (t, J=5.7 Hz, 1H); 4.45 (m, 4H); 5.30 (m, 2H); 6.84 (s, 1H); 6.86 (s, 1H). LC/MS (G): tr=0.80 min; [M+H]⁺: m/z 559; [M−H+HCO₂H]⁻: m/z 603.

5.6. tert-Butyl 3-[2-(2,6-bis-hydroxymethyl-pyridin-4-yloxy)-ethylamino]-butanoate Prepared as for Ex. 2, starting with tert-butyl 3-bromo-butyrate and N-[2-(2,6-bis-hydroxymethyl-pyridin-4-yloxy)-ethyl]-2-nitro-benzenesulfonamide:

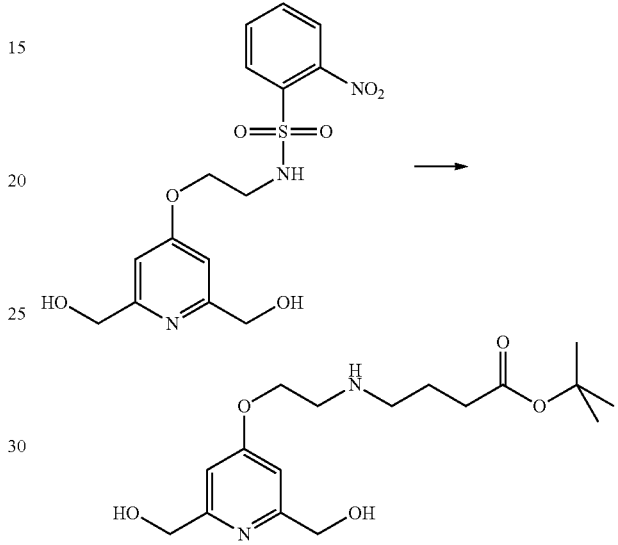

¹H NMR (400 MHz, DMSO-d₆): 1.39 (s, 9H); 1.62 (t, J=7.2 Hz, 2H); 1.84 (broad m, 1H); 2.22 (t, J=7.2 Hz, 2H); 2.55 (t, J=7.2 Hz, 2H); 2.86 (t, J=5.7 Hz, 2H); 4.07 (t, J=5.7 Hz, 2H); 4.45 (d, J=5.7 Hz, 4H); 5.29 (t, J=5.7 Hz, 2H); 6.85 (s, 2H). LC/MS (A): tr=0.40 min; [M+H]⁺: m/z 341; base peak: m/z 156.

Example 6

6.1. Ethyl 4-([2-(2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoate Prepared as for Ex. 5, starting with ethyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate:

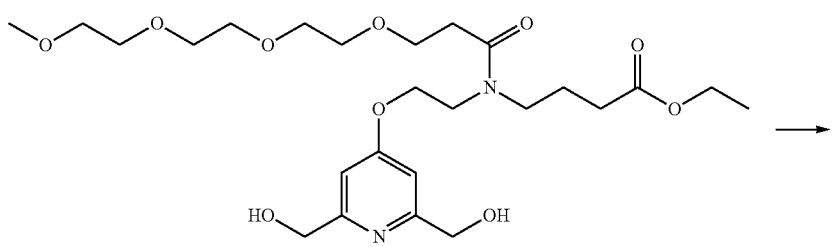

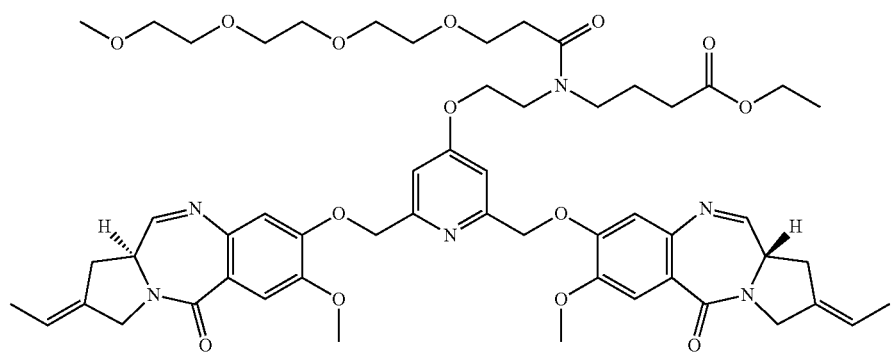 [SMILES: C/C=C1\C[C@H]2C=Nc3cc(OCc4cc(OCCN(CCCC(=O)OCC)C(=O)CCOCCOCCOCCOC)cc(COc5cc6c(cc5OC)C(=O)N5C/C(=C/C)C[C@H]5C=N6)n4)c(OC)cc3C(=O)N2C1]

¹H NMR (500 MHz, DMSO-d₆): 50%-50% mixture of conformers with: 1.11 to 1.18 (m, 3H); 1.54 to 1.82 (m, 8H); 2.24 (d, J=7.3 Hz, 1H); 2.32 (d, J=7.3 Hz, 1H); 2.53 to 2.68 (m, 4H); 2.87 to 3.07 (m, 4H); 3.20 (s, 1.5H); 3.21 (s, 1.5H); 3.31 to 4.27 (m, 32H); 5.16 (d, J=13.2 Hz, 2H); 5.22 (d, J=13.2 Hz, 2H); 5.55 (q, J=7.0 Hz, 2H); 6.94 (s, 2H); 7.08 (s, 2H); 7.37 (s, 2H); 7.76 (d, J=4.4 Hz, 2H). LC/MS (A): tr=0.86 min; [M+H]⁺: m/z 1039; base peak: m/z 376.

6.2. Ethyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate Prepared as for Ex. 5, starting with ethyl 3-[2-(2,6-bis-hydroxymethyl-pyridin-4-yloxy)-ethylamino]-butanoate:

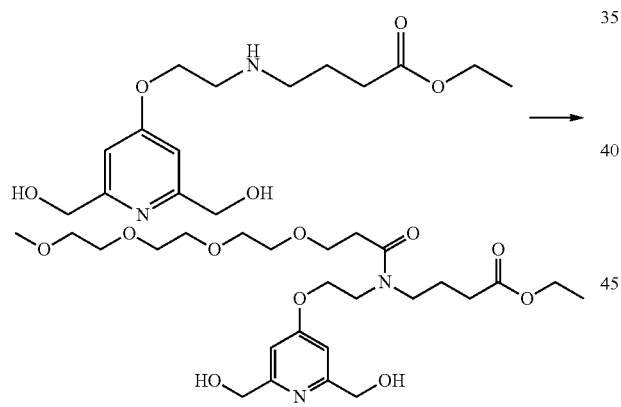

¹H NMR (400 MHz, DMSO-d₆) 50%-50% mixture of conformers with: 1.16 (t, J=7.1 Hz, 1.5H); 1.17 (t, J=7.1 Hz, 1.5H); 1.67 to 1.97 (m, 2H); 2.25 (t, J=7.3 Hz, 1H); 2.34 (t, J=7.3 Hz, 1H); 2.57 (t, J=6.8 Hz, 1H); 2.66 (t, J=6.8 Hz, 1H); 3.23 (s, 3H); 3.32 to 3.74 (m, 18H); 4.04 (q, J=7.1 Hz, 1H); 4.05 (q, J=7.1 Hz, 1H); 4.14 (t, J=5.7 Hz, 1H); 4.19 (t, J=5.7 Hz, 1H); 4.45 (m, 4H); 5.30 (m, 2H); 6.84 (s, 1H); 6.86 (s, 1H). LC/MS (A): tr=0.47 min; [M+H]⁺: m/z 531; base peak: m/z 376; [M−H+HCO₂H]⁻: m/z 575

Example 7

7.1. Methyl 4-([2-(2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridin-4-yloxy)-ethyl]-(3-{2-[2-(2-morpholin-4-yl-ethoxy)-ethoxy]-ethoxy}-propionyl)-amino]-butanoate Prepared as for Ex. 5, starting with methyl 4-[[2-(2,6-bis-hydroxymethyl-pyridin-4-yloxy)-ethyl]-(3-{2-[2-(2-morpholin-4-yl-ethoxy)-ethoxy]-ethoxy}-propionyl)-amino]-butanoate:

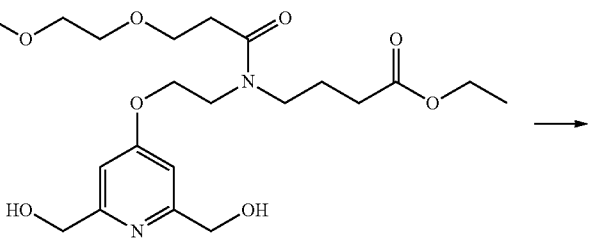

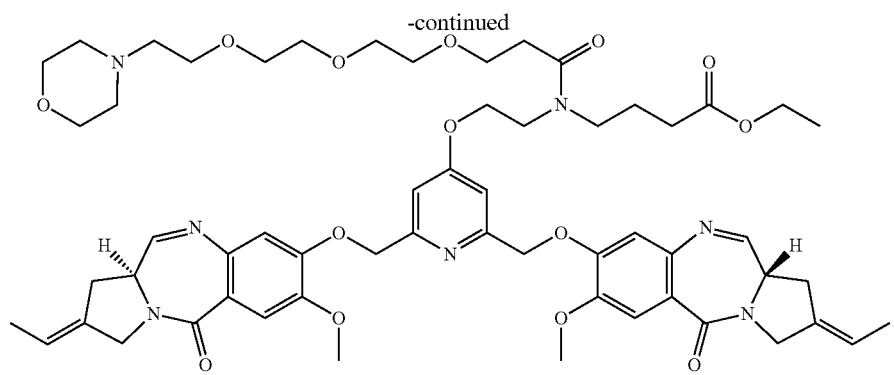

LC/MS (E): tr=0.88 min; [M+H]+: m/z 1080; [M+H2O+H]+: m/z 1098; [M+2H2O+H]+: m/z 1116

7.2. Methyl 4-[[2-(2,6-bis-hydroxymethyl-pyridin-4-yloxy)-ethyl]-(3-{2-[2-(2-morpholin-4-yl-ethoxy)-ethoxy]-ethoxy}-propionyl)-amino]-butanoate Prepared as for Ex. 5, starting with tert-butyl 4-[[2-(2,6-bis-hydroxymethyl-pyridin-4-yloxy)-ethyl]-(3-{2-[2-(2-morpholin-4-yl-ethoxy)-ethoxy]-ethoxy}-propionyl)-amino]-butanoate:

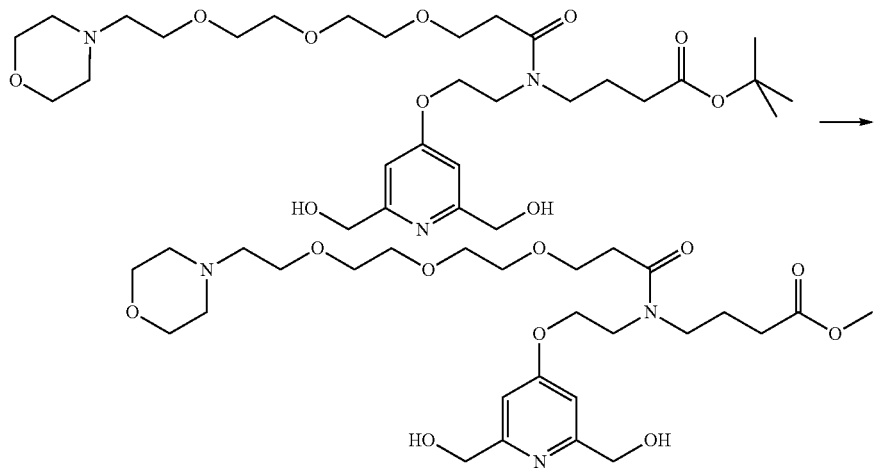

$^1$H NMR (400 MHz, DMSO-d6): 1.83 (m, 2H); 2.33 (m, 2H); 2.42 (m, 4H); 2.48 (t, J=5.8 Hz, 2H); 2.61 (m, 2H); 3.40 (m, 2H); 3.49 to 3.55 (m, 10H); 3.56 (m, 4H); 3.62 (s, 3H); 3.69 (broad t, J=6.6 Hz, 4H); 4.21 (t, J=5.6 Hz, 2H); 4.49 (d, J=5.3 Hz, 4H); 4.90 (t, J=5.3 Hz, 2H); 6.87 (s, 2H). LC/MS (G): tr=0.50 min; [M+H]+: m/z 572; base peak: m/z 198; [M−H+HCO2H]−: m/z 616

7.3. tert-Butyl 4-[[2-(2,6-bis-hydroxymethyl-pyridin-4-yloxy)-ethyl]-(3-{2-[2-(2-morpholin-4-yl-ethoxy))-ethoxy]-ethoxy}-propionyl)-amino]-butanoate Prepared as for Ex. 5, starting with N-hydroxysuccinimidyl 3-{2-[2-(2-morpholin-4-yl-ethoxy)-ethoxy]-ethoxy}-propanoate:

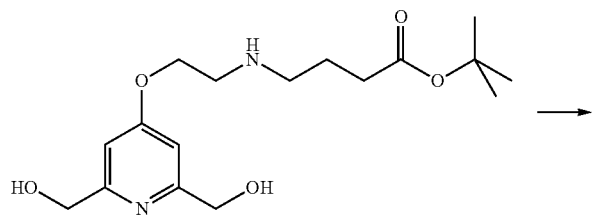

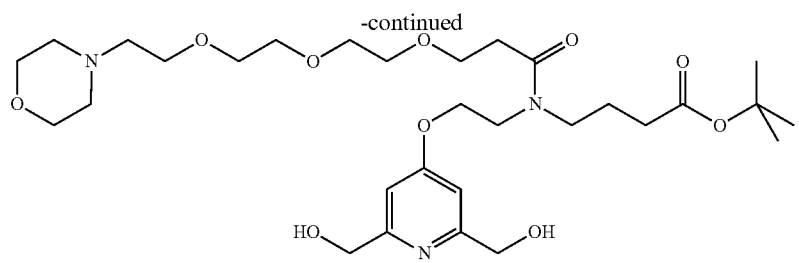

$^1$H NMR (400 MHz, DMSO-$d_6$): 1.42 (s, 9H); 1.78 (m, 2H); 2.22 (m, 2H); 2.42 (m, 4H); 2.48 (t, J=5.8 Hz, 2H); 2.61 (m, 2H); 3.39 (m, 2H); 3.48 to 3.55 (m, 10H); 3.56 (m, 4H); 3.69 (broad t, J=6.6 Hz, 4H); 4.21 (t, J=5.6 Hz, 2H); 4.49 (d, J=5.3 Hz, 4H); 4.90 (t, J=5.3 Hz, 2H); 6.87 (s, 2H). LC/MS (G): tr=0.65 min; [M+H]+: m/z 614; base peak: m/z 240

7.4. N-Hydroxysuccinimidyl 3-{2-[2-(2-morpholin-4-yl-ethoxy)-ethoxy]-ethoxy}-propanoate

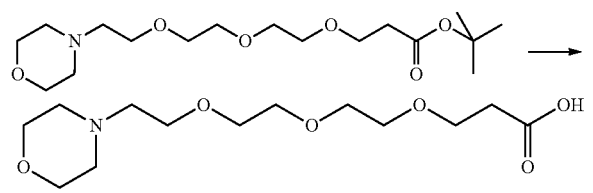

To 830 mg of 3-{2-[2-(2-morpholin-4-yl-ethoxy)-ethoxy]-ethoxy}-propanoic acid dissolved in 50 mL of THF were added 1.1 g of N,N'-disuccinimidyl carbonate and 1.5 mL of DIPEA. After 24 hours at room temperature, 200 mL of DCM were added and the resulting organic phase was concentrated to half its volume under reduced pressure and then washed twice with water, dried over MgSO$_4$ and concentrated under reduced pressure. 1.05 g of N-hydroxysuccinimidyl 3-{2-[2-(2-morpholin-4-yl-ethoxy)-ethoxy]-ethoxy}-propanoate were thus obtained. $^1$H NMR (400 MHz, DMSO-$d_6$): 2.39 (m, 4H); 2.45 (t, J=5.9 Hz, 2H); 2.81 (s, 4H); 2.92 (t, J=6.0 Hz, 2H); 3.45 to 3.57 (m, 14H); 3.72 (t, J=6.0 Hz, 2H). LC/MS (G): tr (ELSD)=0.49 min; [M+H]+: m/z 389.

7.5. 3-{2-[2-(2-Morpholin-4-yl-ethoxy)-ethoxy]-ethoxy}-propanoic acid

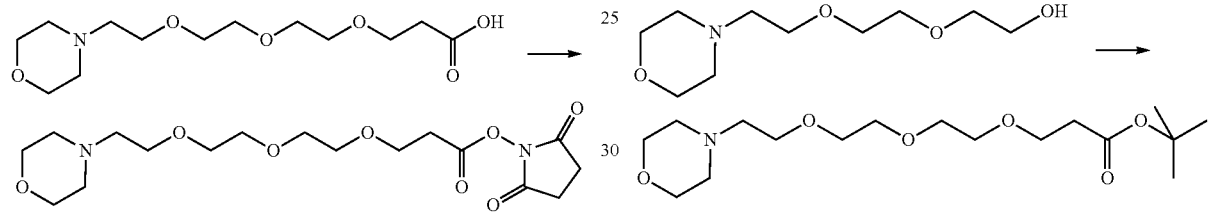

To a solution of 1 g of tert-butyl 3-{2-[2-(2-morpholin-4-yl-ethoxy)-ethoxy]-ethoxy}-propanoate in 50 ml of DCM was added 4 ml of TFA. The mixture was stirred for 10 hours at room temperature and then concentrated under reduced pressure and purified on a Mega BE-SCX, 25GM 150ML cartridge (Varian), using washing with MeOH and detachment of the expected product with a 2N solution of ammonia in MeOH. The fractions containing the desired product were combined and concentrated under reduced pressure. 830 mg of 3-{2-[2-(2-morpholin-4-yl-ethoxy)-ethoxy]-ethoxy}-propanoic acid were obtained. LC/MS (E): tr (ELSD)=0.16 min; [M+H]+: m/z 292

7.6. tert-Butyl 3-{2-[2-(2-morpholin-4-yl-ethoxy)-ethoxy]-ethoxy}-propanoate

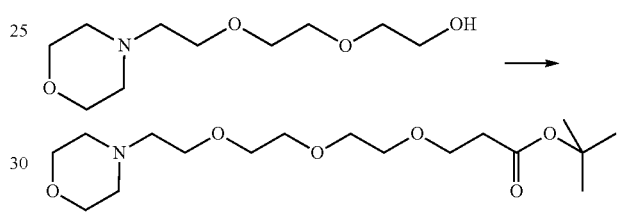

To a solution of 989 mg of 2-[2-(2-morpholin-4-yl-ethoxy)-ethoxy]-ethanol in 2.8 mL of anhydrous THF was added 1.04 mg of sodium. After heating at 40° C. for 2 hours 15 minutes, 793 µL of tert-butyl acrylate were added. After heating for a further two hours at 40° C., the reaction mixture was left for 20 hours at room temperature and then concentrated under reduced pressure and purified by flash chromatography on silica (Merck SuperVarioPrep 70 g column, Si60 15-40 µm), using a gradient of 0 to 6% MeOH in DCM. The fractions containing the desired product were combined and concentrated under reduced pressure. 1 g of tert-butyl 3-{2-[2-[2-(2-morpholin-4-yl-ethoxy)-ethoxy]-ethoxy}-propanoate were obtained. LC/MS (E): tr (ELSD)=0.59 min; [M+H]+: m/z 348

Evaluation of the Inhibition of Proliferation of the Cell Lines MDA-MB-231, MDA-A1 and HCT116 with the Compounds of Formula (IA) with RCG1=—SZ$_a$ (Z$_a$=SMe) or RCG1=—C(=O)Z$_b$R$_b$ (Z$_b$R$_b$=OMe)

MDA-MB-231, MDA-A1 or HCT116 cells in their exponential growth phase were trypsinized and resuspended in their respective culture medium (DMEM/F12 Gibco #21331, 10% FCS Gibco #10500-056, 2 nM Glutamine Gibco #25030 for the MDA cells; DMEM Gibco #11960, 10% FCS Gibco #10500-056, 2 mM Glutamine Gibco #25030 for the HCT116 cells). The cell suspension was seeded in Cytostar 96-well culture plates (GE Healthcare Europe, #RPNQ0163) in the complete culture medium containing serum to a density of 5000 cells/well (MDA-MB-231, MDA-A1, HCT116). After incubation for 4 hours, successive dilutions of the tomaymycin dimers were added to the wells in triplicate for each concentration. The cells were cultured for 3 days at 37° C. under an atmosphere of 5% CO$_2$ in the presence of the cytotoxic agents. On the fourth day, 10 µl of a solution of $^{14}$C-thymidine (0.1 µCi/well, Perkin Elmer #NEC56825000)

were added to each well. The incorporation of $^{14}$C-thymidine was measured 96 hours after the start of the experiment with a Microbeta radioactivity counter (Perkin Elmer). The data are expressed in the form of a percentage of survival by determining the ratio between the Count obtained with the cells treated with the cytotoxic agents and that obtained with the cells of the control wells (treated with the culture medium alone).

TABLE II

| Inhibition of proliferation ($^{14}$C-thymidine pulse at 96 h) | IC50 [pM] | | |
|---|---|---|---|
| Structure of the compound of formula (IA) | HCT116 | MDA-MB231 | MDA-A1 |
| | 61 | 128 | 16270 |
| | 18 | 41 | 3465 |
| | 235 | 384 | 17849 |
| | 48 | 81 | 26474 |

TABLE II-continued

Inhibition of proliferation ($^{14}$C-thymidine pulse at 96 h)

| Structure of the compound of formula (IA) | IC50 [pM] | | |
|---|---|---|---|
| | HCT116 | MDA-MB231 | MDA-A1 |
| 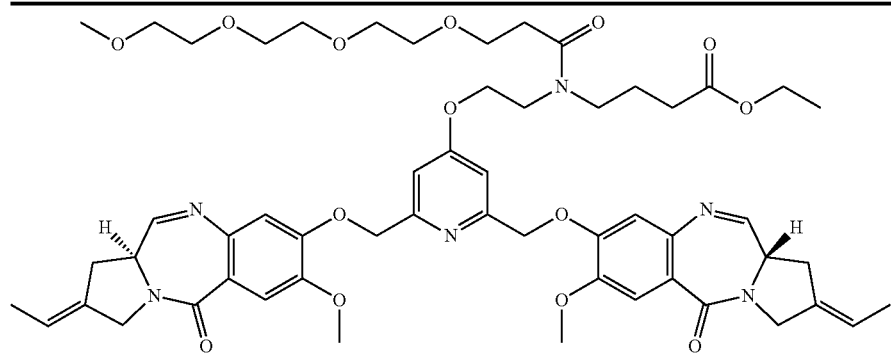 | 4984 | 5665 | >50000 |

It was found that the test compounds, for which RCG1=—SZ$_a$, with Z$_a$=SMe) or RCG1=—C(=O)Z$_b$R$_b$, with Z$_b$R$_b$=OMe, have powerful anticancer activity; this suggests that similar compounds characterized with another group Z$_b$R$_b$ are liable to have at least identical activity.

Chapter 2

Novel Tomaymycin Conjugates

Example 8

Preparation of a conjugate hu2H11 modified with SPDB with 4-{2-[{2-[2-(2-methoxy-ethoxy)-ethoxy]-ethyl}-(2-methyl-(2-methyl-2-mercapto-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine To 24 mg of hu2H11 (antibody described also by hu53 2H11 on page 15 of WO 2008010101; this is an antibody comprising a Vh having the amino acid sequence SED ID No. 24) in 2.37 ml of an aqueous buffer with a potassium phosphate concentration of 0.05 M, 0.05 M NaCl and 2 mM ethylenediaminetetraacetic acid (EDTA) of pH=6.5, was added 320 g of SPDB (described on page 7 of WO 2010/076474) dissolved in 62 μL of DMA with magnetic stirring. After 4 hours at room temperature, the modified antibody was purified by gel filtration on Sephadex G25 (PD-10 GE column) pre-equilibrated in an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8. An aliquot of the modified antibody was treated with dithiothreitol (DTT) to cleave the dithiopyridine groups. The modified antibody along with the pyridinethiol released were assayed by spectrophotometry using the extinction coefficients of pyridinethiol (e$_{343\,nm}$=8080 M$^{-1}$ cm$^{-1}$), of the dithiopyridine group (e$_{280\,nm}$=5100 M$^{-1}$ cm$^{-1}$) and hu2H11 (e$_{280\,nm}$=206941 M$^{-1}$ cm$^{-1}$): an average of 3.2 dithiopyridine groups per antibody molecule was determined at a concentration of 7.08 mg/mL.

To 12 mg of the above modified antibody in 3.2 ml of an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8 was added 713 μL of DMA and 1.22 mg of 4-{2-[{2-[2-(2-methoxy-ethoxy)-ethoxy]-ethyl}-(2-methyl-(2-methyl-2-mercapto-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine dissolved in 87 μL of dimethylacetamide (DMA) with magnetic stirring. After 12 hours at 30° C., the mixture was filtered on Millex®-SV 0.45 μM (PVDF Durapore Millipore) and purified on a Superdex™ 200 prep grade column (Hiload™ 26/60 GE column) pre-equilibrated in a saline phosphate buffer containing 20% N-methylpyrrolidone (NMP). The fractions of interest were combined and concentrated on Amicon Ultra-15 (Ultracel 50k Millipore) and then filtered on Sephadex G-25 (PD10, GE columns) pre-equilibrated in an aqueous buffer at pH=6.5, with a concentration of 10 mM histidine containing 10% sucrose and 5% NMP.

The conjugate obtained (3.5 mL) was assayed by spectrophotometry using the extinction coefficients e$_{320\,nm}$=7843M$^{-1}$ cm$^{-1}$ and e$_{280\,nm}$=4436 M$^{-1}$ cm$^{-1}$ for 4-{2-[{2-[2-(2-methoxy-ethoxy)-ethoxy]-ethyl}-(2-methyl-2-methyldisulfanyl-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine and e$_{280\,nm}$=206941 M$^{-1}$ cm$^{-1}$ for hu2H11: an average of 2.9 tomaymycin (4-{2-[{2-[2-(2-methoxy-ethoxy)-ethoxy]-ethyl}-(2-methyl-(2-methyl-2-mercapto-propy)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine) dimers per antibody molecule was determined at a concentration of 1.74 mg/mL.

Example 9

Preparation of a conjugate hu2H11R35R74 modified with SNPP with 4-{2-[{2-[2-(2-methoxy-ethoxy)-ethoxy]-ethyl}-(2-methyl-(2-methyl-2-mercapto-propyl)-amino]ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine To 100 mg of hu2H11R35R74 (Ref on page 20 of WO 2011039721) in 8.2 ml of an aqueous buffer with a concentration of 0.05 M a potassium phosphate, 0.05 M NaCl and 2 mM ethylenediaminetetraacetic acid (EDTA) of pH=6.5 was added 1.3 mg of SNPP (described on page 36 of WO 2004/

016801) dissolved in 186 µL of DMA with magnetic stirring. After 4 hours at room temperature, the solution of modified antibody was fractionated into four and purified by gel filtration on four Sephadex G25 columns (PD-10 GE column) pre-equilibrated in an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8. After mixing and homogenizing the four filtrates thus obtained, the modified antibody was assayed by spectrophotometry using the extinction coefficients of nitropyridinethiol ($e_{280\ nm}$=3344 M$^{-1}$ cm$^{-1}$ and $e_{325\ nm}$=10964 M$^{-1}$ cm$^{-1}$), and hu2H11R35R74 ($e_{280\ nm}$=219528 M$^{-1}$ cm$^{-1}$): an average of 4.47 dithio-nitropyridine groups per antibody molecule was determined at a concentration of 6.27 mg/mL.

To 87 mg of modified antibody above in 23.24 ml of an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8 was added 4.38 mL of DMA and 17.73 mg of 4-{2-[{2-(2-methoxy-ethoxy)-ethoxy]-ethyl}-(2-methyl-(2-methyl-2-mercapto-propyl-amino]-ethoxy}-2,6-bis-[(S)-2-eth-(E)-ylidene-7-dimethoxy-1,2,3,11a-tetrahydro pyrrolo[2,1c][1.4]benzodiazepin-5-one-8-yloxymethyl]-pyridine dissolved in 1.43 mL of dimethylacetamide (DMA) with magnetic stirring. After 17 hours at 30° C., the mixture was filtered on Steriflip® 0.45 µM (PVDF Durapore Millipore) and purified by 3 injections on a Superdex™ 200 prep grade column (Hiload™ 26/60 GE column) pre-equilibrated in a saline phosphate buffer containing 20% N-methylpyrrolidone (NMP). The fractions of interest were combined and concentrated on Amicon Ultra-15 (Ultracel 50k Millipore) and then filtered on Sephadex G-25 (HiPrep 26/10 desalting, GE column) pre-equilibrated in an aqueous buffer of pH=6.5 with a concentration of 10 mM histidine, containing 10% sucrose and 5% NMP.

The conjugate obtained (28 mL) was assayed by spectrophotometry using the extinction coefficient $e_{280\ nm}$=219528 M$^{-1}$ cm$^{-1}$ for hu2H11R35R74: an average of 3.13 tomaymycin (4-{2-[{2-[2-(2-methoxy-ethoxy)-ethoxy]-ethyl}-(2-methyl-(2-methyl-2-mercapto-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine) dimers per antibody molecule was determined at a concentration of 1.99 mg/mL.

Example 10

Preparation of a conjugate hu2H11R35R74 modified with SPDB with 4-{2-[{2-[2-(2-methoxy-ethoxy)-ethoxy]-ethyl}-(2-methyl-(2-methyl-2-mercapto-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine Prepared as for Ex. 8, starting with hu2H11R35R74: an average of 2.92 tomaymycin (4-{2-[{2-[2-(2-methoxy-ethoxy)-ethoxy]-ethyl}-(2-methyl-(2-methyl-2-mercapto-propyl)-amino]-ethoxy}-2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridine) dimers per antibody molecule was determined.

Example 11

Preparation of a conjugate hu2H11R35R74 with N-hydroxysuccinimidyl 4-([2-(2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy}-propionyl)-amino]-butanoate To a solution of 1.59 mg of hu2H11R35R74 in 150 µL an aqueous buffer with a concentration of 0.043 M of potassium phosphate of pH=6.6 were successively added 6 µL of an aqueous 1 M solution of HEPES, followed by 267 µL of an aqueous buffer with a concentration of 0.05 M N-(2-hydroxyethyl)-piperazine-N'-2-ethanesulfonic acid (HEPES), 0.05 M NaCl and 2 mM ethylenediaminetetraacetic acid (EDTA) of pH=8, 100 µL of DMA and then 83 µg of N-hydroxysuccinimidyl 4-([2-(2,6-bis-[(S)-2-eth-(E)-ylidene-7-dimethoxy-1,2,3,11a-tetrahydropyrrolo[2,1c][1.4]benzodiazepin-5-one-8-yloxymethyl]-pyridin-4-yloxy)-ethyl]-(3-{2-[2-(2-methoxy-ethoxy)-ethoxy]-ethoxy-propionyl)-amino]-butanoate dissolved in 5 µl of DMA. After 4 hours at 30° C., the mixture was filtered on Sephadex G-25 (NAP-5 GE columns) pre-equilibrated in an aqueous buffer of pH=6.5 with a concentration of 10 mM histidine, containing 10% sucrose and 5% NMP.

The conjugate obtained (1 mL) was assayed by spectrophotometry using the extinction coefficients of ethyl 4-[[2-(2,6-bis-hydroxymethyl-pyridin-4-yloxy)-ethyl]-(3-{2-[2-(2-methoxy-ethoxy)-ethoxy]-ethoxy}-propionyl)-amino]-butanoate ($e_{322\ nm}$=7971 M$^{-1}$ cm$^{-1}$ and $e_{280\ nm}$=5219 M$^{-1}$ cm$^{-1}$): an average of 4.18 tomaymycin dimers per antibody molecule was determined at a concentration of 1.14 mg/mL. Evaluation of the Inhibition of Proliferation of the Cell Lines MDA-MB-231 with the Cytotoxic Conjugate hu2H11 (or hu2H11R35R74, Respectively)

MDA-MB-231 cells in their exponential growth phase were trypsinized and resuspended in their culture medium (DMEM/F12 Gibco #21331, 10% FCS Gibco #10500-056, 2 nM Glutamine Gibco #25030). The cell suspension was seeded in Cytostar 96-well plates (GE Healthcare Europe, #RPNQ0163) in whole culture medium containing serum to a density of 5000 cells/well. After incubation for 4 hours, successive dilutions of the antibody-cytotoxic agent immunoconjugates were added to the wells at decreasing concentrations from $10^{-7}$ to $10^{-12}$ M (in triplicate for each concentration). The cells were cultured at 37° C. under an atmosphere containing 5% $CO_2$ in the presence of the antibody-cytotoxic agent immunoconjugates for 3 days. On the fourth day, 10 µl of a solution $^{14}$C-thymidine (0.1 µCi/well, Perkin Elmer #NEC56825000) were added to each well. The incorporation of $^{14}$C-thymidine was measured 96 hours after the start of the experiment with a Microbeta radioactivity counter (Perkin Elmer). The data are expressed in the form of a percentage of survival by determining the ratio between accounts obtained with the cells treated with the immunoconjugate and that obtained with the cells of the control wells (treated with the culture medium alone). In certain experiments indicated with an asterisk (*), the naked antibody hu2H11 (or hu2H11R35R74, respectively) was added to the wells to a concentration of 1 µM at the start of the experiment and the inhibition of proliferation was measured as described previously.

TABLE III
| Inhibition of proliferation ($^{14}$C-thymidine pulse at 96 h) Structure | IC50 [pM] | | |
|---|---|---|---|
| | Mean IC50 | Mean IC50 (+naked Ab*) | IC50 ratio |
| 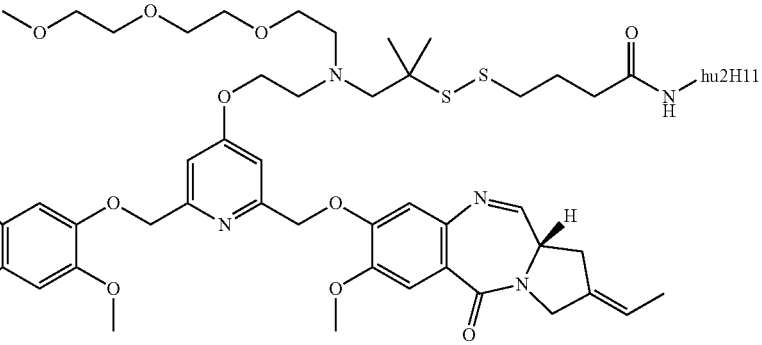 | 58 | 760 | 13 |
| 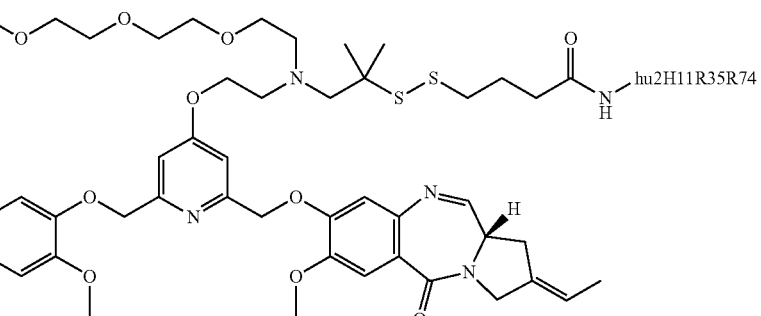 | 32 | 502 | 16 |
| 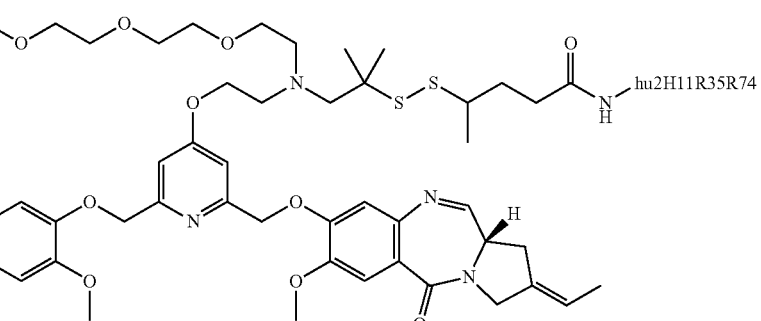 | 72 | 3550 | 49 |
The invention claimed is:
1. Compound of formula (I):
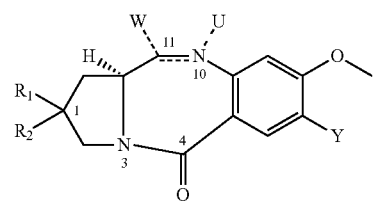
-continued
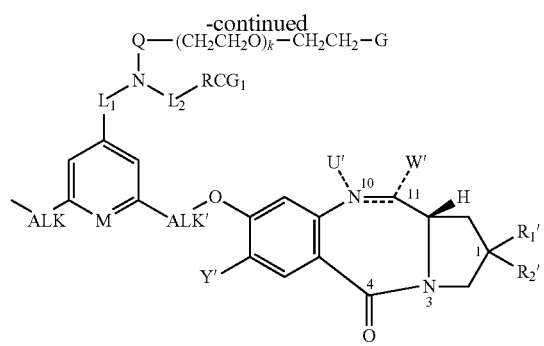

in which:
==== represents a single bond or a double bond, with the condition that if ==== represents a single bond, then:
U and/or U', which may be identical or different, represent, independently of each other, H;
W and/or W', which may be identical or different, represent, independently of each other: OH, —OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —SO$_3^-$, —NRSOOR', —NRR', a cyclic amine such that N10 and C11 are included in a ring, —NROR', —NRCOR', —N$_3$, —CN, Hal, a trialkylphosphonium or triarylphosphonium group;
if represents a double bond, then:
U and U' are absent;
W and/or W', which may be identical or different, represent, independently of each other, H;
$R_1$, $R_2$, $R_1'$, $R_2'$, which may be identical or different, represent, independently of each other: H, Hal or a group $(C_1-C_6)$alkyl optionally substituted with one or more substituents chosen from: Hal, CN, NRR', CF$_3$, OR, an aryl or heteroaryl group, S(O)$_q$R with q=0, 1 or 2;
or alternatively
$R_1$ and $R_2$ and/or $R_1'$ and $R_2'$ together form, respectively, a double bond =CH$_2$ or =CH—CH$_3$;
Y and Y', which may be identical or different, represent, independently of each other, H or —OR;
M represents CH or N;
ALK and ALK' denote a group $(C_1-C_6)$alkylene;
R and R' represent, independently of each other, H or a group $(C_1-C_6)$alkyl or aryl optionally substituted with one or more substituents chosen from: Hal, CN, NRR', CF$_3$, OR, an aryl or heteroaryl group;
$L_1$ represents:
a single bond;
or
the group —(OCH$_2$CH$_2$)$_i$—, attached to the phenyl or pyridyl ring via the oxygen atom, i representing an integer ranging from 2 to 40;
or
the group -D-(C$_1$-C$_6$)ALK- attached to the phenyl or pyridyl ring via D, in which D represents —O—, —NH— or —N(C$_1$-C$_4$)alkyl-;
$L_2$ represents:
a group —(C$_1$-C$_6$)ALK-;
or
the group —(CH$_2$CH$_2$O)$_j$—CH$_2$CH$_2$—, j representing an integer ranging from 1 to 40;
or
a group —(CH$_2$CH$_2$O)$_j$—CH$_2$CH$_2$NR''—(C$_1$-C$_6$)ALK-, attached to the nitrogen atom via the unit —(CH$_2$CH$_2$O)—, j representing an integer ranging from 1 to 40 and R'' representing H or a group $(C_1-C_4)$alkyl;
Q represents a single bond or the group C(=O);
k represents an integer ranging from 0 to 40;
G represents a group —OR or —NRR', R and R' being as defined previously or being such that they form, with the nitrogen atom to which they are attached, a group (C$_4$-C$_{10}$)heterocycloalkyl which may comprise in the ring another heteroatom chosen from N, O and S and which may be optionally substituted with at least one substituent chosen from a group $(C_1-C_4)$alkyl, a halogen atom and a hydroxyl group;
RCG1 represents the group —SZ$_a$ or —C(=O)—Z$_b$R$_b$;
Z$_a$ represents Ac, R$_a$ or SR$_a$;
R$_a$ represents H, or a group $(C_1-C_6)$alkyl, $(C_3-C_8)$cycloalkyl, aryl, heteroaryl or (C$_4$-C$_{10}$)heterocycloalkyl optionally substituted with one or more substituents chosen from: Hal, CN, NRR', CF$_3$, OR, NO$_2$, an aryl or heteroaryl group;
Z$_b$ represents a single bond, —O— or —NH— and R$_b$ representing H or a group $(C_1-C_6)$alkyl, $(C_3-C_8)$cycloalkyl, aryl, heteroaryl or (C$_4$-C$_{10}$)heterocycloalkyl or alternatively Z$_b$ represents a single bond and R$_b$ represents Hal;
with the condition that if $L_1$ represents a single bond, then RCG1 represents —SZ$_a$.

2. The compound according to claim 1 in which U=U' and/or W=W' and/or $R_1=R_1'$ and/or $R_2=R_2'$ and/or Y=Y' and/or the two groups ALK and ALK' attached to the phenyl or pyridyl nucleus are identical.

3. The compound according to claim 1 of formula (IA) or (IB):

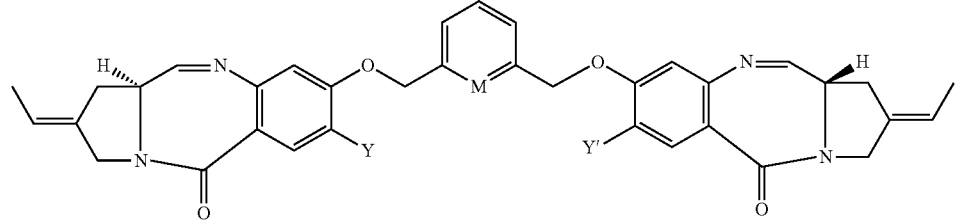

(IA)

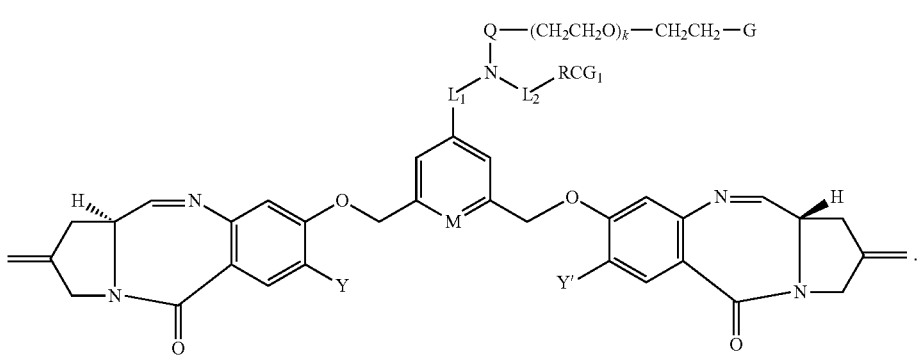

4. The compound according to claim 3 of formula (IA):

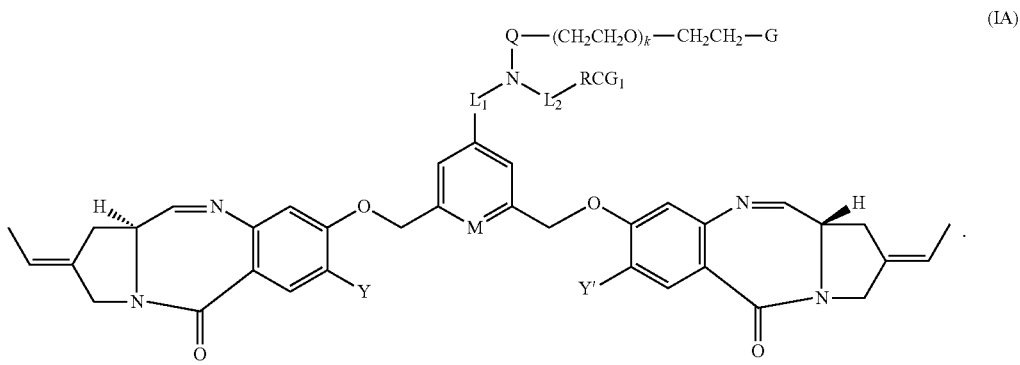

5. The compound according to claim 1 in which Y and Y' represent a group $(C_1-C_4)$alkoxy.

6. The compound according to claim 1 in which M represents N.

7. The compound according to claim 1 in which if $L_1$ represents a single bond, $L_2$ represents $—(CH_2CH_2O)_j—CH_2CH_2—$ or $—(CH_2CH_2O)_j—CH_2CH_2NR''—(C_1-C_6)ALK-$.

8. The compound according to claim 1 in which G represents a group $—OH$, $—O(C_1-C_6)$alkyl, $—NH_2$, $—NH(C_1-C_6)$alkyl or $—N(C_1-C_6)$alkyl$_2$ or G represents a group $—NRR'$ in which R and R' form, together with the nitrogen atom to which they are attached, a group $(C_4-C_{10})$heterocycloalkyl which may comprise in the ring another heteroatom chosen from N, O and S and which may be optionally substituted with at least one substituent chosen from a group $(C_1-C_4)$alkyl, a halogen atom and a hydroxyl group.

9. The compound according to claim 1 in which:
$L_1$=-D-$(C_1-C_6)$ALK- and $L_2$=—$(C_1-C_6)$ALK-; or
$L_1$=—$(OCH_2CH_2)_i$— and $L_2$=—$(C_1-C_6)$ALK-; or
$L_1$=single bond and $L_2$=—$(CH_2CH_2O)_j$—$CH_2CH_2NR''$—$(C_1-C_6)$ALK-; or
$L_1$=-D-$(C_1-C_6)$ALK-, and $L_2$=—$(CH_2CH_2O)_j$—$CH_2CH_2NR''$—$(C_1-C_6)$ALK-; or
$L_1$=-D-$(C_1-C_6)$ALK- and $L_2$=—$(CH_2CH_2O)_j$—$CH_2CH_2$—.

10. The compound according to claim 1 in which:
$L_1$=-D-$(C_1-C_6)$ALK-, $L_2$=—$(C_1-C_6)$ALK-, Q=single bond, k=1-10, G=OR, RCG1=—$SZ_a$;
$L_1$=-D-$(C_1-C_6)$ALK-, $L_2$=—$(C_1-C_6)$ALK-, Q=CO, k=1-10, G=OR, RCG1=—$SZ_a$;
$L_1$=—$(OCH_2CH_2)_i$—, $L_2$=—$(C_1-C_6)$ALK-, Q=single bond, k=1-10, G=OR, RCG1=—$SZ_a$;
$L_1$=—$(OCH_2CH_2)_i$—, $L_2$=—$(C_1-C_6)$ALK-, Q=CO, k=1-10, G=OR, RCG1=—$SZ_a$;
$L_1$=-D-$(C_1-C_6)$ALK-, $L_2$=—$(C_1-C_6)$ALK-, Q=single bond, k=1-10, G=NRR', RCG1=—$SZ_a$;
$L_1$=-D-$(C_1-C_6)$ALK-, $L_2$=—$(C_1-C_6)$ALK-, Q=CO, k=1-10, G=NRR', RCG1=—$SZ_a$;
$L_1$=single bond, $L_2$=—$(CH_2CH_2O)_j$—$CH_2CH_2NR''$—$(C_1-C_6)$ALK-, Q=single bond, k=1-10, G=OR, RCG1=—$SZ_a$;
$L_1$=single bond, $L_2$=—$(CH_2CH_2O)_j$—$CH_2CH_2NR''$—$(C_1-C_6)$ALK-, Q=CO, k=1-10, G=OR, RCG1=—$SZ_a$;
$L_1$=single bond, $L_2$=—$(CH_2CH_2O)_j$—$CH_2CH_2NR''$—$(C_1-C_6)$ALK-, Q=single bond, k=0-10, G=NRR', RCG1=—$SZ_a$;
$L_1$=single bond, $L_2$=—$(CH_2CH_2O)_j$—$CH_2CH_2NR''$—$(C_1-C_6)$ALK-, Q=CO, k=0-10, G=NRR', RCG1=—$SZ_a$;
$L_1$=-D-$(C_1-C_6)$ALK-, $L_2$=—$(CH_2CH_2O)_j$—$CH_2CH_2NR''$—$(C_1-C_6)$ALK-, Q=single bond, k=0-10, G=NRR', RCG1=—$SZ_a$;
$L_1$=-D-$(C_1-C_6)$ALK-, $L_2$=—$(CH_2CH_2O)_j$—$CH_2CH_2NR''$—$(C_1-C_6)$ALK-, Q=CO, k=0-10, G=NRR', RCG1=—$SZ_a$;
$L_1$=-D-$(C_1-C_6)$ALK-, $L_2$=—$(CH_2CH_2O)_j$—$CH_2CH_2NR''$—$(C_1-C_6)$ALK-, Q=single bond, k=1-10, G=OR, RCG1=—$SZ_a$;
$L_1$=-D-$(C_1-C_6)$ALK-, $L_2$=—$(CH_2CH_2O)_j$—$CH_2CH_2NR''$—$(C_1-C_6)$ALK-, Q=CO, k=1-10, G=OR, RCG1=—$SZ_a$;

$L_1=$-D-$(C_1$-$C_6)$ALK-, $L_2=$—$(C_1$-$C_6)$ALK-, Q=single bond, k=1-10, G=OR, RCG1=—C(=O)$Z_bR_b$;

$L_1=$-D-$(C_1$-$C_6)$ALK-, $L_2=$—$(C_1$-$C_6)$ALK-, Q=CO, k=1-10, G=OR, RCG1=—C(=O)$Z_bR_b$;

$L_1=$-D-$(C_1$-$C_6)$ALK-, $L_2=$—$(C_1$-$C_6)$ALK-, Q=single bond, k=1-10, G=NRR', RCG1=—C(=O)$Z_bR_b$;

$L_1=$-D-$(C_1$-$C_6)$ALK-, $L_2=$—$(C_1$-$C_6)$ALK-, Q=CO, k=1-10, G=NRR', RCG1=—C(=O)$Z_bR_b$;

$L_1=$—$(OCH_2CH_2)_i$—, $L_2=$—$(C_1$-$C_6)$ALK-, Q=single bond, k=1-10, G=OR, RCG1=—C(=O)$Z_bR_b$;

$L_1=$—$(OCH_2CH_2)_i$—, $L_2=$—$(C_1$-$C_6)$ALK-, Q=CO, k=1-10, G=OR, RCG1=—C(=O)$Z_bR_b$;

$L_1=$—$(OCH_2CH_2)_i$—, $L_2=$—$(C_1$-$C_6)$ALK-, Q=single bond, k=1-10, G=NRR', RCG1=—C(=O)$Z_bR_b$;

$L_1=$—$(OCH_2CH_2)_i$—, $L_2=$—$(C_1$-$C_6)$ALK-, Q=CO, k=1-10, G=NRR', RCG1=—C(=O)$Z_bR_b$;

$L_1=$-D-$(C_1$-$C_6)$ALK-, $L_2=$—$(CH_2CH_2O)_j$—$CH_2CH_2$—, Q=single bond, k=1-10, G=OR, RCG1=—C(=O)$Z_bR_b$;

$L_1=$-D-$(C_1$-$C_6)$ALK-, $L_2=$—$(CH_2CH_2O)_j$—$CH_2CH_2$—, Q=CO, k=1-10, G=OR, RCG1=—C(=O)$Z_bR_b$;

$L_1=$-D-$(C_1$-$C_6)$ALK-, $L_2=$—$(CH_2CH_2O)_j$—$CH_2CH_2$—, Q=single bond, k=0-10, G=NRR', RCG1=—C(=O)$Z_bR_b$;

$L_1=$-D-$(C_1$-$C_6)$ALK-, $L_2=$—$(CH_2CH_2O)_j$—$CH_2CH_2$—, Q=CO, k=0-10, G=NRR', RCG1=—C(=O)$Z_bR_b$.

11. The compound according to claim 1 in which —CO$Z_bR_b$ represents —COOH, —COO($C_1$-$C_6$)alkyl,

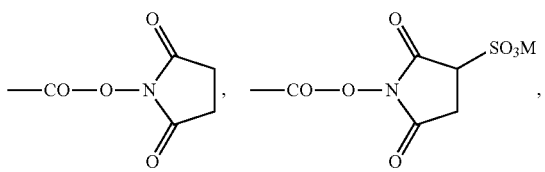

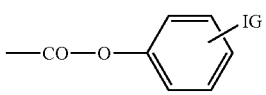

M = H or cation or the group

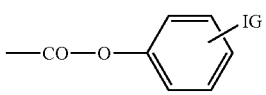

in which IG represents at least one inductive group, or

12. The compound according to claim 1 in which —S$Z_a$ represents —SH or —SS($C_1$-$C_6$)alkyl or —SS-heteroaryl.

13. The compound according to claim 1, where in the compound is selected from the group consisting of:

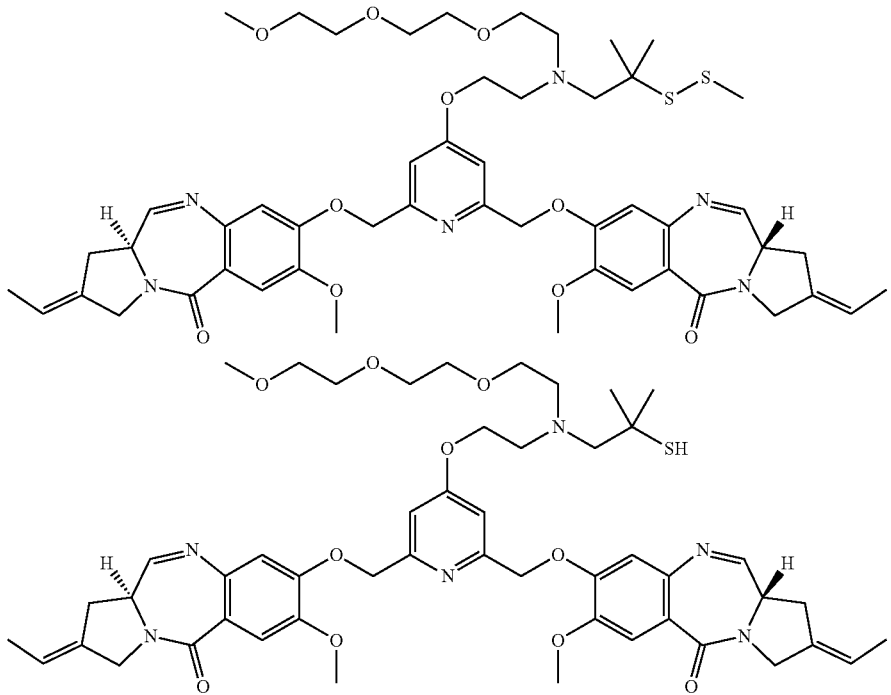

-continued
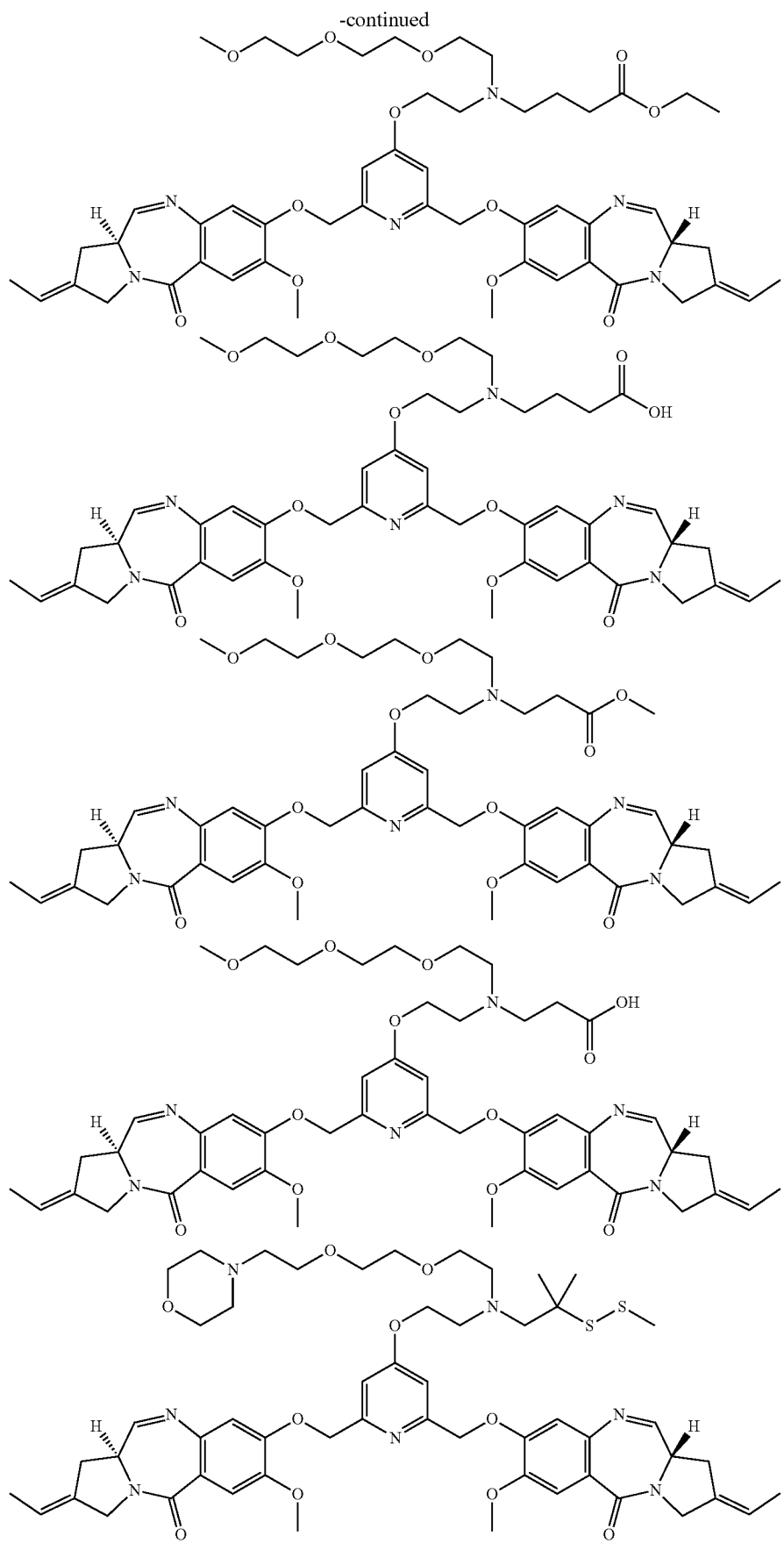

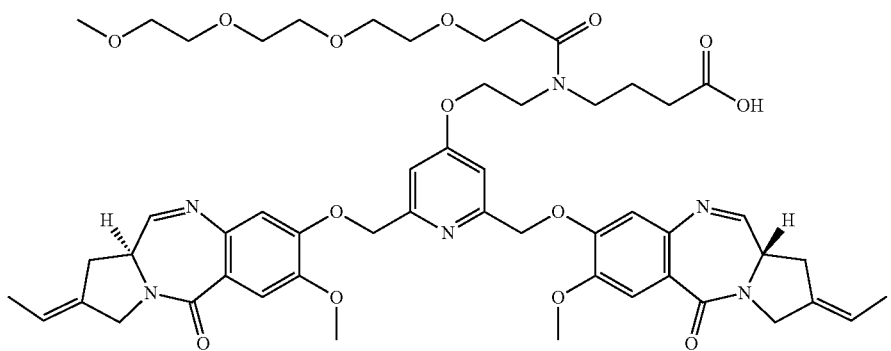
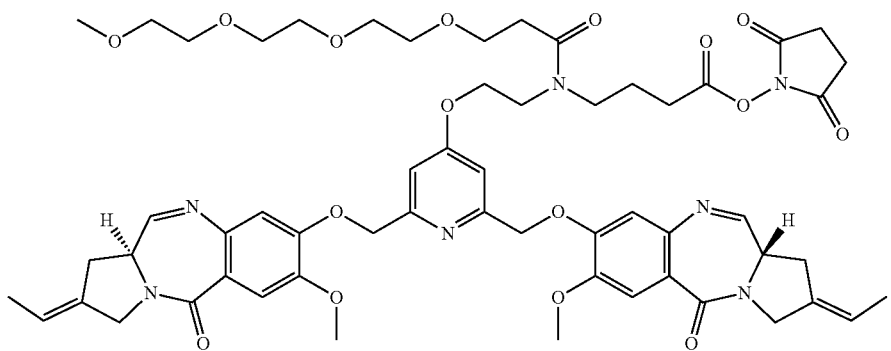
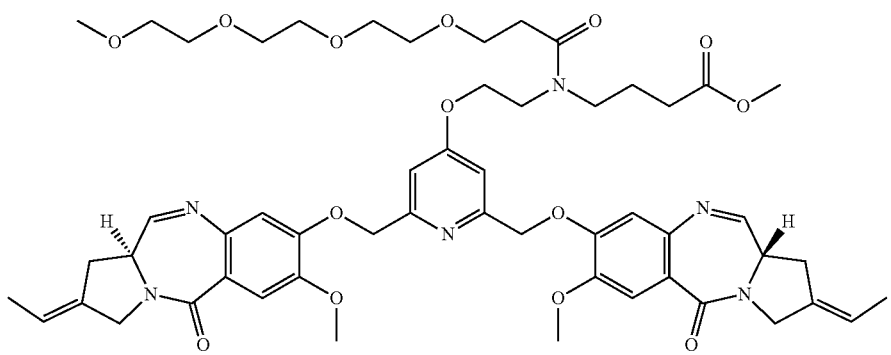
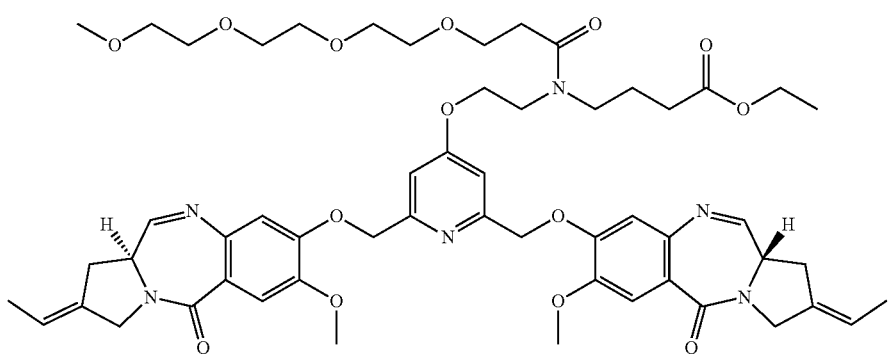

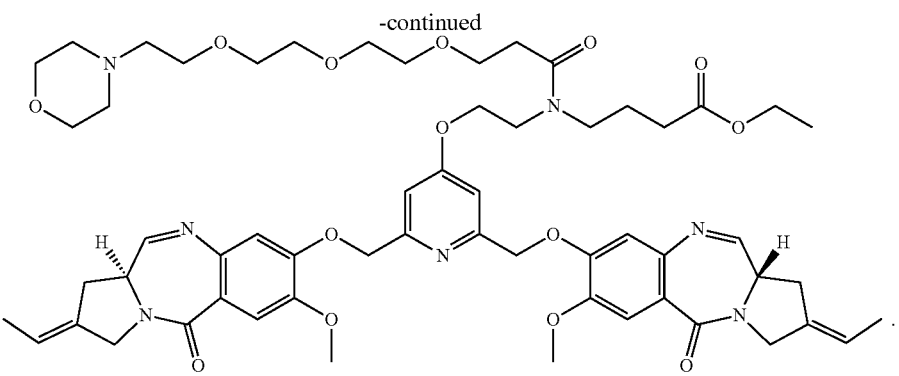

14. A process for preparing a conjugate comprising a compound of formula (I):

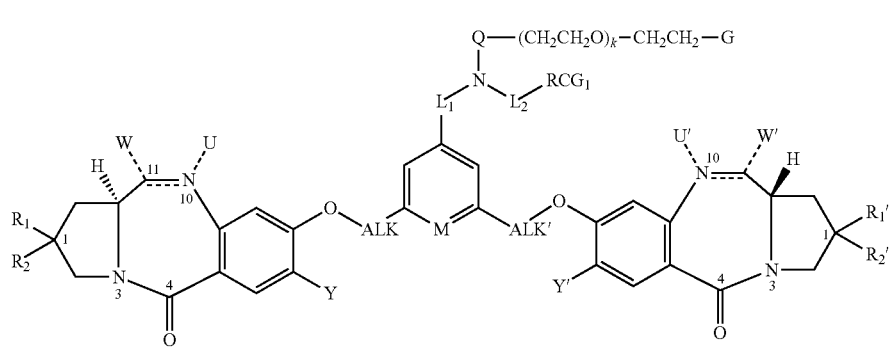

and a binding agent wherein:
- === represents a single bond or a double bond, with the condition that
- === if represents a single bond, then:
  - U and/or U', which may be identical or different, represent, independently of each other, H;
  - W and/or W', which may be identical or different, represent, independently of each other: OH, —OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —SO$_3^-$, —NRSOOR', —NRR', a cyclic amine such that N10 and C11 are included in a ring, —NROR', —NRCOR', —N$_3$, —CN, Hal, a trialkylphosphonium or triarylphosphonium group;
- if === represents a double bond, then:
  - U and U' are absent;
  - W and/or W', which may be identical or different, represent, independently of each other, H;
- $R_1$, $R_2$, $R_1'$, $R_2'$, which may be identical or different, represent, independently of each other: H, Hal or a group (C$_1$-C$_6$)alkyl optionally substituted with one or more substituents chosen from: Hal, CN, NRR', CF$_3$, OR, an aryl or heteroaryl group, S(O)$_q$R with q=0, 1 or 2;
- or alternatively
- $R_1$ and $R_2$ and/or $R_1'$ and $R_2'$ together form, respectively, a double bond =CH$_2$ or =CH—CH$_3$;
- Y and Y', which may be identical or different, represent, independently of each other, H or —OR;
- M represents CH or N;
- ALK and ALK' denote a group (C$_1$-C$_6$)alkylene;
- R and R' represent, independently of each other, H or a group (C$_1$-C$_6$)alkyl or aryl optionally substituted with one or more substituents chosen from: Hal, CN, NRR', CF$_3$, OR, an aryl or heteroaryl group;
- $L_1$ represents:
  - a single bond;
  - or
  - the group —(OCH$_2$CH$_2$)$_i$—, attached to the phenyl or pyridyl ring via the oxygen atom, i representing an integer ranging from 2 to 40;
  - or
  - the group -D-(C$_1$-C$_6$)ALK- attached to the phenyl or pyridyl ring via D, in which D represents —O—, —NH— or —N(C$_1$-C$_4$)alkyl-;
- $L_2$ represents:
  - a group —(C$_1$-C$_6$)ALK-;
  - or
  - the group —(CH$_2$CH$_2$O)$_j$—CH$_2$CH$_2$—, j representing an integer ranging from 1 to 40;
  - or
  - a group —(CH$_2$CH$_2$O)$_j$—CH$_2$CH$_2$NR''—(C$_1$-C$_6$)ALK-, attached to the nitrogen atom via the unit —(CH$_2$CH$_2$O)—, j representing an integer ranging from 1 to 40 and R'' representing H or a group (C$_1$-C$_4$)alkyl;
- Q represents a single bond or the group C(=O);
- k represents an integer ranging from 0 to 40;
- G represents a group —OR or —NRR', R and R' being as defined previously or being such that they form, with the nitrogen atom to which they are attached, a group (C$_4$-C$_{10}$)heterocycloalkyl which may comprise in the ring another heteroatom chosen from N, O and S and which may be optionally substituted with at least one substituent chosen from a group $(C_1-C_4)$alkyl, a halogen atom and a hydroxyl group;

RCG1 represents the group $-SZ_a$ or $-C(=O)-Z_bR_b$;

$Z_a$ represents Ac, $R_a$ or $SR_a$;

$R_a$ represents H, or a group $(C_1-C_6)$alkyl, $(C_3-C_8)$cycloalkyl, aryl, heteroaryl or $(C_4-C_{10})$heterocycloalkyl optionally substituted with one or more substituents chosen from: Hal, CN, NRR', $CF_3$, OR, $NO_2$, an aryl or heteroaryl group;

$Z_b$ represents a single bond, $-O-$ or $-NH-$ and $R_b$ representing H or a group $(C_1-C_6)$alkyl, $(C_3-C_8)$cycloalkyl, aryl, heteroaryl or $(C_4-C_{10})$heterocycloalkyl or alternatively $Z_b$ represents a single bond and $R_b$ represents Hal;

with the condition that if $L_1$ represents a single bond, then RCG1 represents $-SZ_a$, which consists in:

(i) placing in contact and leaving to react:

an optionally buffered aqueous solution of the binding agent, optionally modified by means of a modifying agent, and a solution of a compound of formula (I), the chemical group RCG1 of the compound of formula (I) being reactive towards the chemical groups RCG2 present on the binding agent especially towards the amino groups present on antibodies, the said chemical groups RCG2 having been introduced, where appropriate, by the modifying agent, so as to attach the compound of formula (I) to the binding agent with formation of a covalent bond;

(ii) and then optionally to separate the conjugate formed in step (i) from the compound of formula (I) and/or from the unreacted binding agent and/or from any aggregates that may have formed.

15. The process according to claim 14 in which:

in the presence of a derivative of formula (I) comprising a reactive chemical group RCG1 of the type $-SZ_a$, the binding agent comprises:

disulfide chemical groups in the case where RCG1 represents $-SH$;

thiol chemical groups in the case where RCG1 represents $-SZ_a$ with $Z_a \neq H$;

maleimido or haloacetamido chemical groups in the case where RCG1 represents $-SH$;

in the presence of a derivative of formula (I) comprising a reactive chemical group RCG1 of the type $-C(=O)-Z_bR_b$, the derivative of formula (I) is reacted with the amino functional groups of the binding agent, especially the ε-amino groups borne by the side chains of the lysine (Lys) residues of an antibody.

16. The process according to claim 14 in which:

when the reactive chemical group RCG1 is of the type $-SH$, and when the binding agent bears amino functional groups, especially ε-amino groups borne by the side chains of the lysine residues of an antibody, the latter is modified by means of a modifying agent chosen from a compound of formula:

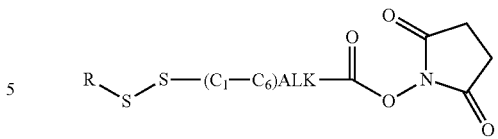

in which R represents a group $(C_1-C_6)$alkyl, aryl, heteroaryl, $(C_3-C_7)$cycloalkyl, $(C_4-C_{10})$heterocycloalkyl;

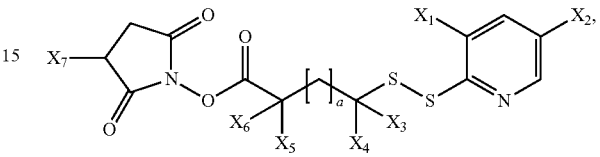

a pegylated analogue of formula:

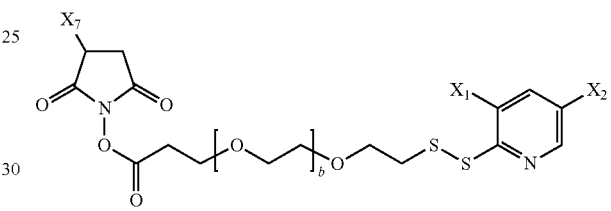

or a sulfonic analogue of formula

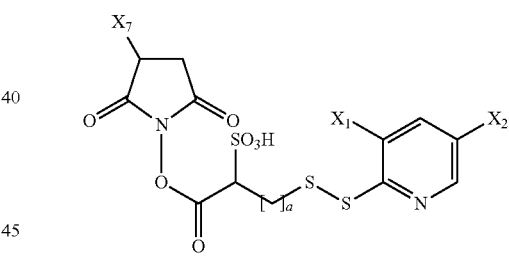

in which $X_3$, $X_4$, $X_5$, $X_6$ represent H or a group $(C_1-C_6)$alkyl, $X_1$ and $X_2$ represent $-H$, $-CONX_8X_9$, $-NO_2$, $X_8$ and $X_9$ representing H or a group $(C_1-C_6)$alkyl, $X_7$ represents $-SO_3^-M^+$ or H or alternatively a quaternary ammonium group and a denotes an integer ranging from 0 to 4 and b denotes an integer ranging from 0 to 2000; or chosen from succinimidyl-4-(N-maleimidomethyl)cyclohexane-1-carboxylate; sulfosuccinimidyl 4-(N-maleimidomethyl)cyclohexane-1-carboxylate;

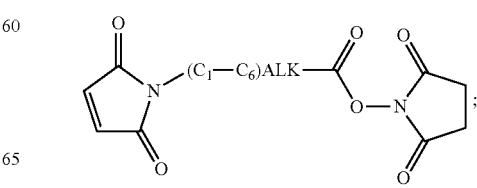

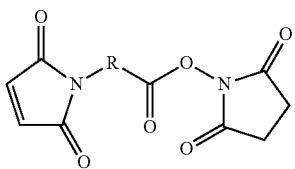

in which R represents a group —(CH$_2$)$_n$—, —(CH$_2$)$_n$-cyclohexyl-, -cyclohexyl-(CH$_2$)$_n$— and n represents an integer ranging from 1 to 10;

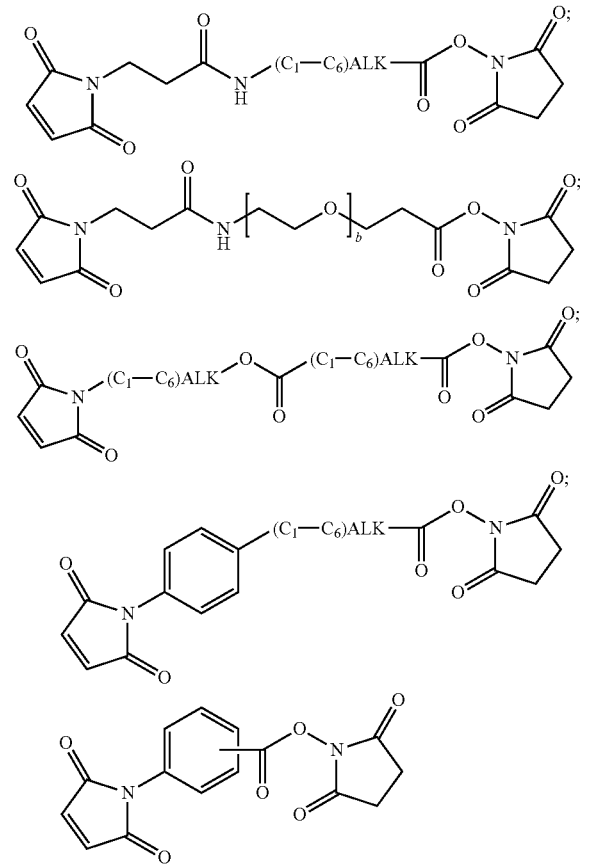

b being an integer between 0 and 2000;

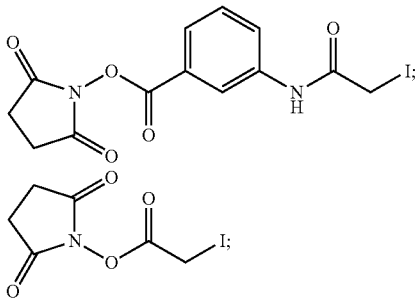

succinimidyl-N-bromoacetate; succinimidyl-3-(N-bromoacetamido)propionate;

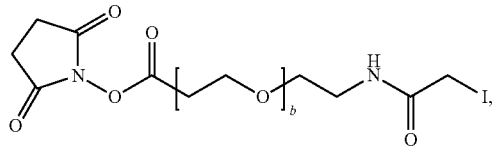

b being an integer between 0 and 2000 when the reactive chemical group RCG1 is of the type —SZ$_a$ with Z$_a$≠H, and when the binding agent bears amino functional groups, especially ε-amino groups borne by the side chains of the lysine residues of an antibody, the latter is modified by means of a modifying agent chosen from a compound of formula

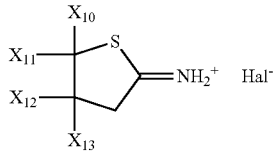

in which:

Hal represents a halogen atom;

X$_{10}$ represents a halogen atom or the group —COOX$_{14}$, nitro, unsubstituted or halogenated (C$_1$-C$_8$)alkyl, unsubstituted or halogenated (C$_1$-C$_8$)alkoxy, unsubstituted or halogenated (C$_2$-C$_8$)alkenyl, unsubstituted or halogenated (C$_2$-C$_8$) alkynyl, unsubstituted (C$_3$-C$_8$)cycloalkyl, aryl which is unsubstituted or substituted with one to three substituents selected from amino, a halogen atom, unsubstituted or halogenated group (C$_1$-C$_8$)alkyl, unsubstituted or halogenated (C$_1$-C$_8$)alkoxy;

each of the X$_{11}$, X$_{12}$, X$_{13}$ independently represents a hydrogen atom or alternatively may represent X$_{10}$;

or X$_{10}$ and X$_{11}$ together form a (C$_2$-C$_5$)alkylene ring, which is unsubstituted or substituted with one to five groups (C$_1$-C$_4$)alkyl;

or X$_{10}$ or X$_{11}$ form, together with X$_{12}$, a (C$_1$-C$_5$)alkylene ring, which is unsubstituted or substituted with one to five groups (C$_1$-C$_4$) alkyl and X$_{14}$ is —H or a group (C$_1$-C$_8$)alkyl or X$_{10}$=X$_{11}$=X$_{12}$=X$_{13}$=H when the reactive chemical group RCG1 is of the type —SH, and when the binding agent bears thiol functional groups, especially following the introduction of cysteines by mutation or by chemical modification of a binding agent bearing amino functional groups, the binding agent is modified such that its thiol functional groups are converted into disulfide functional groups, more particularly by means of a modifying agent chosen from a compound of formula

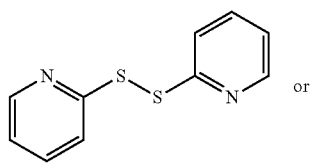 or

-continued

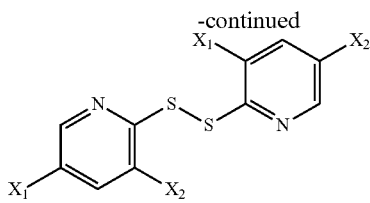

in which $X_1$ and $X_2$ represent —H, —$CONX_8X_9$ or —$NO_2$, $X_8$ and $X_9$ representing H or a group ($C_1$-$C_6$)alkyl.

17. A conjugate obtained via the process according to claim 14.

18. A conjugate obtained via the process according to claim 14, wherein the conjugate is in solution.

19. A process for preparing a conjugate comprising a binding agent to which is covalently attached in the para position of M a dimer of formula

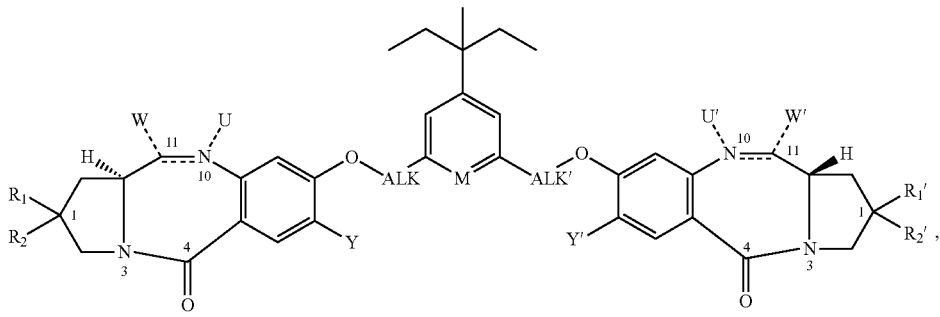

comprising placing in contact and leaving to react:
an optionally buffered aqueous solution of the binding agent, optionally modified by means of a modifying agent,
and
a solution of a compound of formula (I) so as to attach the compound of formula (I) to the binding agent with formation of a covalent bond, wherein
=== represents a single bond or a double bond, with the condition that
if === represents a single bond, then:
U and/or U', which may be identical or different, represent, independently of each other, H;
W and/or W', which may be identical or different, represent, independently of each other: OH, —OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —$SO_3^-$, —NRSOOR', —NRR', a cyclic amine such that N10 and C11 are included in a ring, —NROR', —NRCOR', —$N_3$, —CN, Hal, a trialkylphosphonium or triarylphosphonium group;
if === represents a double bond, then:
U and U' are absent;
W and/or W', which may be identical or different, represent, independently of each other, H;
$R_1$, $R_2$, $R_1'$, $R_2'$, which may be identical or different, represent, independently of each other: H, Hal or a group ($C_1$-$C_6$)alkyl optionally substituted with one or more substituents chosen from: Hal, CN, NRR', $CF_3$, OR, an aryl or heteroaryl group, $S(O)_qR$ with q=0, 1 or 2;
or alternatively
$R_1$ and $R_2$ and/or $R_1'$ and $R_2'$ together form, respectively, a double bond =$CH_2$ or =CH—$CH_3$;
Y and Y', which may be identical or different, represent, independently of each other, H or —OR;
M represents CH or N;
ALK and ALK' denote a group ($C_1$-$C_6$)alkylene;
R and R' represent, independently of each other, H or a group ($C_1$-$C_6$)alkyl or aryl optionally substituted with one or more substituents chosen from: Hal, CN, NRR', $CF_3$, OR, an aryl or heteroaryl group; and
Q represents a single bond or the group C(=O).

20. The process according to claim 19 in which the binding agent is an antibody.

21. The process according to claim 19 in which the dimer has the formula:

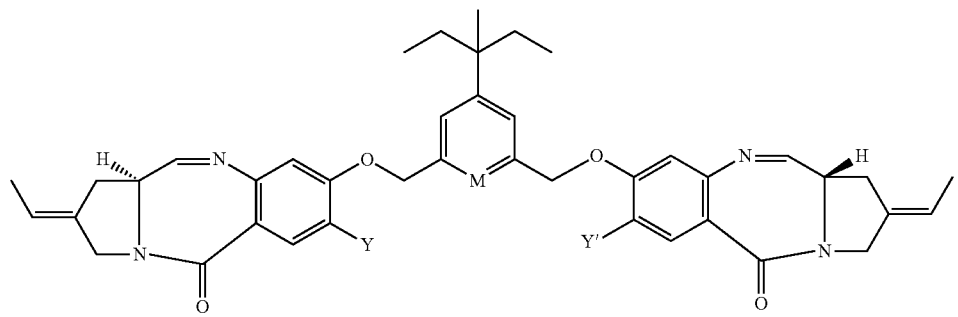

-continued
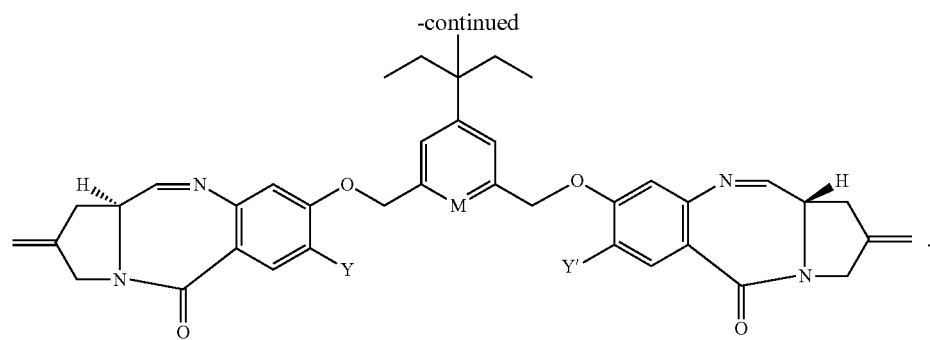
* * * * *